United States Patent
Perriman et al.

(10) Patent No.: US 11,723,985 B2
(45) Date of Patent: Aug. 15, 2023

(54) PROTEIN DELIVERY TO MEMBRANES

(71) Applicant: CYTOSEEK LIMITED, Bristol (GB)

(72) Inventors: Adam Willis Perriman, Bristol (GB); Robert Christopher Deller, Bristol (GB); Wenjin Xiao, Bristol (GB); Thomas Iain Phillip Green, Bristol (GB); Benjamin Michael Carter, Bristol (GB); Graham John Day, Bristol (GB); Rosalia Cuahtecontzi Delint, Bristol (GB)

(73) Assignee: CYTOSEEK LIMITED, Bristol (GB)

( * ) Notice: Subject to any disclaimer, the term of this patent is extended or adjusted under 35 U.S.C. 154(b) by 524 days.

(21) Appl. No.: 16/644,354

(22) PCT Filed: Sep. 7, 2018

(86) PCT No.: PCT/GB2018/052534
§ 371 (c)(1),
(2) Date: Mar. 4, 2020

(87) PCT Pub. No.: WO2019/048871
PCT Pub. Date: Mar. 14, 2019

(65) Prior Publication Data
US 2021/0060174 A1  Mar. 4, 2021

(30) Foreign Application Priority Data

Sep. 8, 2017 (GB) ...................... 1714485
Sep. 11, 2017 (GB) ...................... 1714566

(51) Int. Cl.
*A61K 47/60* (2017.01)
*A61K 47/69* (2017.01)
*A61L 27/18* (2006.01)
*A61L 27/22* (2006.01)
*C12N 9/16* (2006.01)

(52) U.S. Cl.
CPC .......... *A61K 47/6909* (2017.08); *A61K 47/60* (2017.08); *A61L 27/18* (2013.01); *A61L 27/227* (2013.01); *C12N 9/16* (2013.01); *C07K 2319/00* (2013.01); *C12Y 301/08001* (2013.01)

(58) Field of Classification Search
CPC ...... C07K 14/00; C07K 14/705; A61K 38/00; A61K 47/50
See application file for complete search history.

(56) References Cited

U.S. PATENT DOCUMENTS 8,293,244 B2 * 10/2012 Horne ................. C12N 9/16
424/190.1
9,259,398 B1  2/2016 Klein et al.
2007/0287681 A1 12/2007 Jeong et al.

FOREIGN PATENT DOCUMENTS

| DE | 10 2005 032 055 A1 | 1/2007 | |
| WO | 2007/143574 A1 | 12/2007 | |
| WO | 2009/134808 A2 | 11/2009 | |
| WO | 2010/129023 A2 | 11/2010 | |
| WO | 2010/129023 A3 | 11/2010 | |
| WO | 2010/129023 A9 | 11/2010 | |
| WO | WO-2010129023 A2 * | 11/2010 | ........... C07K 14/001 |
| WO | 2014/176311 A1 | 10/2014 | |
| WO | 2016/069910 A1 | 5/2016 | |
| WO | 2017/187114 A1 | 11/2017 | |

OTHER PUBLICATIONS

Database UniProt XP-002786300, 2007.
Database XP-002786299, 2015.
Database XP-002786298, 2014.
Hajduczki, A., et al. "Solubilization of a Membrane Protein by Combinatorial Supercharging," ACS Chem. Biol. 2011, 6, 301-307.
Matsuura, J., et al. "Structure and Stability of Insulin Dissolved in 1-Octanol," J. Am. Chem. Soc. 1993, 115, 1261-1264.
Perriman, A.W., et al. "Reversible dioxygen binding in solvent-free liquid myoglobin," Nature Chemistry 2010, vol. 2, 622-626.
Brogan, A.P.S., et al. "Isolation of a Highly Reactive ß-Sheet-Rich Intermediate of Lysozyme in a Solvent-Free Liquid Phase," J. Phys. Chem. B 2013, 117, 8400-8407.
Futami, J., et al. "Intracellular Delivery of Proteins into Mammalian Living Cells by Polyethylenimine-Cationization," Journal of Bioscience and Bioengineering, vol. 99, No. 2, 95-103, 2005.
Lawrence, M.S., et al. "Supercharging Proteins Can Impart Unusual Resilience," J. Am. Chem. Soc. 2007, 129, 10110-10112.
McNaughton, B.R., et al. "Mammalian cell penetration, siRNA transfection, and DNA transfection by supercharged proteins," PNAS 2009, vol. 106, No. 15, 6111-6116.
Armstrong, J.P.K., et al. "3D Bioprinting Using a Templated Porous Bioink," Adv. Healthcare Mater. 2016, 5, 1724-1730.
Chen, X., et al. "Fusion Protein Linkers: Property, Design and Functionality," Adv Drug Deliv Rev. 2013; 65(10): 1357-1369.
Liguo, A., et al. "Design of a Phosphinate-Based Fluorescent Probe for Superoxide Detection in Mouse Peritoneal Macrophages," Chem. Eur. J. 2007, 13, 1411-1416.
UK Intellectual Property Office, Corrected Search Report issued in corresponding Application No. GB1714485.8, dated Aug. 29, 2018.

* cited by examiner

*Primary Examiner* — Karen Cochrane Carlson
(74) *Attorney, Agent, or Firm* — Stites & Harbison, PLLC; Terry L. Wright

(57) ABSTRACT

There is provided a phospholipid composition which is a bilayer or micelle comprising at least one embedded protein-polymer surfactant conjugate comprising an anchor protein, wherein the anchor protein is a cationised protein or an anionised protein, the composition characterised in that the anchor protein is: a) an active enzyme; or b) is a protein which does not comprise a —$CH_2C(O)NCH_3(CH_2)_3NCH_3)_2H^+$ linker covalently bonded to an amino acid side chain.

26 Claims, 12 Drawing Sheets

Specification includes a Sequence Listing.

SEQUENCE LISTING

<160> NUMBER OF SEQ ID NOS: 40

<210> SEQ ID NO 1
<211> LENGTH: 1147
<212> TYPE: DNA
<213> ORGANISM: Agrobacterium radiobacter

<400> SEQUENCE: 1

```
cggtttccct ctagaaataa ttttgtttaa ctttaagaag gagatataca tatgcaccat      60
caccatcacc atagcatggc acgtccgatt ggcaccggtg atctgattaa taccgttcgt     120
ggtccgattc cggttagcga agcaggtttt accctgacac atgaacatat ttgtggtagc     180
agcgcaggtt ttctgcgtgc atggcctgaa tttttggta gccgtaaagc actggttgaa      240
aaagcagtgc gtggtctgcg tcatgcccgt gcagccggtg ttcagaccat tgttaaagtt     300
agcacctttg atattggtcg tgatgttcgt ctgctggccg aagttagccg tgcagcaaaa     360
gttcatattg ttgcagcaac cggtctgtgg ttcaaaccgc ctctgagcat gcgtatgcgt     420
agcgttaaaa aactgaccca gttttttctg cgcgaaattc agcatggtat caaaaaaacc     480
ggtattcgtg ccggtattat caaagttgca accaccggta agcaacccc gtttcaagaa     540
ctggtgctgc gtgcagcagc ccgtgcaagc ctggcaaccg gtgttccggt taccacacat     600
accagcgcaa gccagcgtaa aggtgaacag caggcagcaa ttttttgaaag cgaaggtctg     660
agcccgagcc gtgtttgtat tggtcatagt gatgatacca aaaagctgag ctatctgacc     720
ggtctggcag cacgtggtta tctggttggt ctggatcgta tgccgtatag cgcaattggt     780
ctgaaaggta atgcaagcgc actggcactg tttggcaccc gtagctggca gacccgtgca     840
ctgctgatta aagccctgat tgatcgtggt tataaagatc gtattctggt gagccatgat     900
tggctgtttg gttttagcag ctatgtgacc aatattatgg atgtgatgga tcgcattaat     960
ccggatggta tggcatttgt tccgctgcgt gttattccgt tcctgcgtga aaaaggtgtt    1020
ccgcctgaaa cactggcagg cgttaccgtt gcaaatccgg cacgttttct gagtccgacc    1080
gtgcgtgcaa gctaagaatt cgagctcccg ggtaccatgg catgcatcga tagatccggc    1140
tgctaac                                                              1147
```

<210> SEQ ID NO 2
<211> LENGTH: 1147

```
<212> TYPE: DNA
<213> ORGANISM: Artificial Sequence
<220> FEATURE:
<223> OTHER INFORMATION: Synthetic gene sequence

<400> SEQUENCE: 2
cggtttccct ctagaaataa ttttgtttaa ctttaagaag gagatataca tatgcaccat    60
caccatcacc atagcatggc acgtccgatt ggcaccggtg atctgattaa taccgttcgt   120
ggtccgattc cggttagcga agcaggtttt accctgacac atgaacatat tgtgggtagc   180
agcgcaggtt ttctgcgtgc atggcctgaa ttttttggta gccgtaaagc actggttgaa   240
aaagcagtgc gtggtctgcg tcatgcccgt gcagccggtg ttcagaccat tgttaaagtt   300
agcacctttg atattggtcg tgatgttcgt ctgctggccg aagttagccg tgcagcaaaa   360
gttcatattg ttgcagcaac cggtctgtgg ttcaaaccgc tctgagcat gcgtatgcgt    420 agcgttaaaa aactgaccca gttttttctg cgcgaaattc agcatggtat caaaaaaacc   480
ggtattcgtg ccggtattat caaagttgca accaccggta agcaaccccc gtttcaagaa   540
ctggtgctgc gtgcagcagc ccgtgcaagc ctggcaaccg tgttccggt taccacacat    600 accagcgcaa gccagcgtaa aggtgaacag caggcagcaa tttttgaaag cgaaggtctg   660
agcccgagcc gtgtttgtat tggtcatagt gatgatacca aaaagctgag ctatctgacc   720
ggtctggcag cacgtggtta tctggttggt ctggatcgta tgccgtatag cgcaattggt   780
ctgaaaggta atgcaagcgc actggcactg tttggcaccc gtagctggca gacccgtgca   840
ctgctgatta aagcccctgat tgatcgtggt tataaagatc gtattctggt gagccatgat   900
tggctgtttg gttttagcag ctatgtgacc aatattatgg atgtgatgga tcgcattaat   960
ccggatggta tggcatttgt tccgctgcgt gttattccgt tcctgcgtga aaaaggtgtt  1020
ccgcctgaaa cactgcaggc gttaccgtt gcaaatccgg cacgttttct gagtccgacc  1080
gtgcgtgcaa gctaagaatt cgagctcccg ggtaccatgg catgcatcga tagatccggc  1140
tgctaac                                                            1147

<210> SEQ ID NO 3
<211> LENGTH: 714
<212> TYPE: DNA
<213> ORGANISM: Artificial Sequence
<220> FEATURE:
<223> OTHER INFORMATION: Synthetic gene sequence

<400> SEQUENCE: 3
gcttcgaaag gtgaacgcct gtttcgcggt aaagttccga ttcttgtgga actgaaaggc    60
gatgtgaacg gacacaaatt tcggtacgt gggaaaggta aaggcgatgc aacccgcgga   120
aaactgaccc tcaaattcat ttgcaccact ggcaagctgc cgttccatg gccaacctta   180 gtgacaacct tgacctatgg cgttcagtgc ttctctcgtt atccgaaaca catgaaacgt   240
catgacttct ttaaatccgc gatgccgaaa ggctatgtgc aggaacgcac gatcagcttt   300
aagaaagacg gcaaatacaa gactcgcgcg gaagtcaagt tgaaggacg tacgcttgtg   360 aatcgcatca aactgaaagg gcgcgatttc aaagagaaag gcaacattct gggccacaaa   420
ttacggtaca actttaacag tcacaaggtc tacattacgg ccgataaacg gaagaatggc   480
atcaaagcga aattcaaaat tcgtcacaat gtgaaggatg gtagcgttca actggccgat   540
cattaccagc agaatacgcc cattggtcgt ggtccggtat tgttaccgcg gaaccattat   600
```

```
ctgagtacac gctcaaaact gagcaaagac ccgaaagaaa agcgcgatca tatggtactg    660
ctggaatttg tcactgcagc tgggatcaag catggtcgcg atgagcgcta taaa          714
```

<210> SEQ ID NO 4
<211> LENGTH: 1794
<212> TYPE: DNA
<213> ORGANISM: Artificial Sequence
<220> FEATURE:
<223> OTHER INFORMATION: Synthetic gene sequence

<400> SEQUENCE: 4

```
gcttcgaaag gtgaacgcct gtttcgcggt aaagttccga ttcttgtgga actgaaaggc     60
gatgtgaacg gacacaaatt ttcggtacgt gggaaaggta aaggcgatgc aacccgcgga    120
aaactgaccc tcaaattcat ttgcaccact ggcaagctgc ccgttccatg gccaaccttg    180
gtgacaacct tgacctatgg cgttcagtgc ttctctcgtt atccgaaaca catgaaacgt    240
catgacttct ttaaatccgc gatgccgaaa ggctatgtgc aggaacgcac gatcagcttt    300
aagaaagacg gcaaatacaa gactcgcgcg gaagtcaagt ttgaaggacg tacgcttgtg    360
aatcgcatca aactgaaagg cgcgattttc aaagagaaag caacattctg gggccacaaa    420
ttacggtaca actttaacag tcacaaggtc tacattacgg ccgataaacg gaagaatggc    480
atcaaagcga aattcaaaat tcgtcacaat gtgaaggatg gtagcgttca actggccgat    540
cattaccagc agaatacgcc cattggtcgt ggtccggtat tgttaccgcg gaaccattat    600
ctgagtacac gctcaaaact gagcaaagac ccgaaagaaa agcgcgatca tatggtactg    660
ctggaatttg tcactgcagc tgggatcaag catggtcgcg atgagcgcta taaaggcagc    720
gaggcagcag caaaggaagc ggcggcgaaa gaggctgctg ctaagggatc tatgagcatg    780
gcgcgcccga ttggcaccgg cgatctgatt aacaccgtgc gcggcccgat tccggtgagc    840
gaagcgggct ttaccctgac ccatgaacat atttgcggca gcagcgcggg ctttctgcgc    900
gcgtggccgg aattttttgg cagccgcaaa gcgctggtgg aaaaagcggt gcgcggcctg    960
cgccatgcgc gcgcggcggg cgtgcagacc attgtggatg tgagcacctt tgatattggc   1020
cgcgatgtgc gcctgctggc ggaagtgagc cgcgcggcgg atgtgcatat tgtggcggcg   1080
accggcctgt ggtttgatcc gccgctgagc atgcgcatgc gcagcgtgga agaactgacc   1140
cagttttttc tgcgcgaaat tcagcatggc attgaagata ccggcattcg cgcgggcatt   1200
attaaagtgg cgaccaccgg caaagcgacc ccgtttcagg aactggtgct gcgcgcggcg   1260
gcgcgcgcga gcctggcgac cggcgtgccg gtgaccaccc ataccagcgc gagccagcgc   1320
gatggcgaac agcaggcggc gattttttgaa agcgaaggcc tgagcccgag ccgcgtgtgc   1380
attggccata gcgatgatac cgatgatctg agctatctga ccggcctggc ggcgcgcggc   1440
tatctggtgg gcctggatcg catgccgtat agcgcgattg gcctggaagg caacgcgagc   1500
gcgctggcgc tgtttggcac ccgcagctgg cagacccgcg cgctgctgat taaagcgctg   1560
attgatcgcg gctataaaga tcgcattctg gtgagccatg attggctgtt ggctttagc    1620 agctatgtga ccaacattat ggatgtgatg gatcgcatta cccggatggg catggcgttt   1680
gtgccgctgc gcgtgattcc gtttctgcgc gaaaaaggcg tgccgccgga aaccctggcg   1740
ggcgtgaccg tggcgaaccc ggcgcgcttt ctgagcccga ccgtgcgcgc gagc         1794
```

<210> SEQ ID NO 5
<211> LENGTH: 3054
<212> TYPE: DNA

<213> ORGANISM: Artificial Sequence
<220> FEATURE:
<223> OTHER INFORMATION: Synthetic gene sequence

<400> SEQUENCE: 5

```
atggatgaaa caagtgcgag tggggtacag aacgaagttg ctcgtgccga tttggcggaa      60
tccccggcta ccgccaccgc gcccgtcgcg tctgaagcct cccagaatgc ggaaaccaca     120
gtggctgcga ccgctactga agcccgcag accgcggaaa acactgctcc taccaacagt     180
gccagtgaat caaccgaaaa accgatggac gaacagcctg tggcttctga accccacaa     240
ccaagcgtcg agaaaccggt attaccgacc gaggtgaaac cggcagagaa tacaactccg     300
gcaagtacgg aggccagtcc ggagacagtt tctccatcgc gcgcgacaga ccagcctgta     360
gccacccgtg attccgtgca gtctagccgt tcgcgccggt tgcgccgtga cctggaagct     420
accgctgtga cgccaggtac aggtccggct ggtgcggatg atgcaacacc gattcctcgt     480
gtcagcaaac cgaccctgtc agagtcagaa aaaaagaat ccacccaact ggcgaagcag     540
attaactggg tagacttctc cgacacgcg tcaatgaaga atttagatcc gcaaggagga     600
ttcaaagtag gtaccgtttt caaaaaggaa atctcgccgg ttatgtggt gacgctgacc     660
gttactgaac tgaaaccctt caacagcacc gaaatttaca agaaacgcgt tgaagggact     720
cccacggcaa atacctacga cccgaacgcg atcaatagct atctgaaagg ctataaagat     780
tacggtaaaa ccccgccgtc tgttacgggc cgcccgcaga caaattttc aaccattggc     840
ggtcaggggt tcgataccca aggtcgtaaa acgcagatca ttttgccgga cgacgcggtt     900
aattgggca tcaaatttaa ggtggaagca acctatcgcg gaaatcctgt gaaaccttcg     960
gtcgttatgg ccgatgggga agatgccaat ccggctgaat atgggatttt cacgactaac    1020
ggtgaagggt gggagtatgt gggcgaatgg atgaaaggac cccgcgcgaa aggcccgtac    1080
actgtgatga ctgaagatat ggtgaaggca ttcgataaaa cccgcaaaga cggtctgctg    1140
atcctgaaag ataaaagcgt tgactggagc aaatacttgt ctccagacac agttactggt    1200
ggattaggta gccaggtgtt cggcccgatc atctcagcct caaaagcggt accggtggtt    1260
atgactcgcg gtgcgagcga agtcgggttt tatgtcgcca cgggtgggca acaagccctc    1320
atgatgggtt ttctcgttgt cgattcgagc gacgcaccag ccagctatgg cgaagcgtat    1380
catactattg gcacgcggga ttccattgcg aataccccga tcaatcagcc ttacttaggt    1440
agcaccgcag cagacattga tgcggactct gaaagtgact ggactgccga tgaccgcgaa    1500
gatgtagcag atgaaggccc cgcccagttg ctgacggctg accagcttag caaaaccaac    1560
gatttactgg acctgaacaa agccaagaac gggacctaca ccctcaaaat caaagcgaac    1620
ccaaacggta acgcaaaagc gtacgtcaag gcatgggtgg atttcaacaa caatggcaaa    1680
tttgatgaca atgaaggctc ggtggtgaag gagattaccg ccaacgggga tcatacgctg    1740
tcctttaacg ccattcctgg ccttaccggc ggcctggtgg accagattgg catgcgggta    1800
cgcattgcga cgaatgcagg ggatattgag aaaccgacag taccgcgtt cagtggggaa    1860
gtagaggata tgctggttcg ccgtgtctat ccgccacaag gcgaaaagca ggaatctact    1920
ggcttccaag gagaaaccca gaatgcttcg gtgcacttta ccgcaaaagg accggatcgc    1980
tccgattttg taaccaacgc gagcatgagc aatcaagcgc acaggttct ggataatcag    2040
ggcaacgttc tgacgccgac caatggtaat acctatgtac gtcccgaggg aacgtacgtg    2100
gtgacagcca atgcgatga tgtcaacgtt acgttcactc cgaacgagga tttcagcggt    2160
gttgcggagg gtattaacat tcgtcgcact gactcaaatg gttccagcac gggttggcag    2220
```

```
tcgacggatg cagcagatcc gaataagaac gatcgcttga acaacatgga cggccgtttt    2280
gtgccaaccg tccgcaaagt gcctaaatac gacagtacgg gcattcaggg ccaggatatg    2340
gcctcgaaag gcgaacgcct gtttcgcggc aaagtgccga ttctggtaga acttaaaggt    2400
gatgtgaatg gccacaaatt tagcgtgcgt ggcaaaggta aggcgatgc aacgcgtggc     2460 aaattaacgc tcaaatttat ctgtacgact ggcaaattac ccgtgccgtg gcccacccttt   2520 gttacgacgc tgacctatgg tgtccaatgc ttttcccgtt atccgaaaca catgaaacgt    2580
cacgacttct ttaaaagcgc catgcctaaa ggctatgtcc aagagcgcac gatctcgttt    2640
aagaaagacg ggaaatataa gacccgggcg aagtcaaat ttgagggccg tacgctggtg    2700
aatcgcatta aactgaaggg acgcgacttt aaagagaaag gcaatatcct gggtcataag    2760
ctccgctaca actttaactc tcataaagtc tacatcaccg ctgataaacg caaaaatggc    2820
atcaaagcaa aattcaagat tcgccataac gttaaggatg gttctgtcca gctggcggat    2880
cattatcagc aaaacacccc aattggccgt ggtccggttc ttctgccacg taaccactat   2940
ctgtcaacgc gttcgaaatt gagtaaggat ccgaaagaga acgtgatca catggtgctg     3000 ctggaatttg tcacagccgc gggtatcaaa catggccggg atgaacgcta caag          3054
```

<210> SEQ ID NO 6
<211> LENGTH: 777
<212> TYPE: DNA
<213> ORGANISM: Artificial Sequence
<220> FEATURE:
<223> OTHER INFORMATION: Synthetic gene sequence

<400> SEQUENCE: 6

```
gcttcgaaag gtgaacgcct gtttcgcggt aaagttccga ttcttgtgga actgaaaggc      60
gatgtgaacg gacacaaatt ttcggtacgt gggaaaggta aggcgatgc aacccgcgga     120 aaactgaccc tcaaattcat ttgcaccact ggcaagctgc ccgttccatg gccaaccttt    180 gtgacaaccct tgacctatgg cgttcagtgc ttctctcgtt atccgaaaca catgaaacgt    240
catgacttct ttaaatccgc gatgccgaaa ggctatgtgc aggaacgcac gatcagcttt    300
aagaaagacg gcaaatacaa gactcgcgcg gaagtcaagt ttgaaggacg tacgcttgtg    360
aatcgcatca aactgaaagg gcgcgatttc aaagagaaag gcaacattct gggccacaaa    420
ttacggtaca actttaacag tcacaaggtc tacattacgg ccgataaacg gaagaatggc    480
atcaaagcga aattcaaaat tcgtcacaat gtgaaggatg gtagcgttca actggccgat    540
cattaccagc agaatacgcc cattggtcgt ggtccggtat tgttaccgcg gaaccattat    600
ctgagtacac gctcaaaact gagcaaagac ccgaaagaaa agcgcgatca tatggtactg    660 ctggaattttg tcactgcagc tgggatcaag catggtcgcg atgagcgcta taaacgccgc    720
cctaaaggcc gtggtaaacg tcgtcgtgag aaacaacgcc ctaccgactg tcatctc        777
```

<210> SEQ ID NO 7
<211> LENGTH: 1119
<212> TYPE: DNA
<213> ORGANISM: Artificial Sequence
<220> FEATURE:
<223> OTHER INFORMATION: Synthetic gene sequence

<400> SEQUENCE: 7

```
gcttcgaaag gtgaacgcct gtttcgcggt aaagttccga ttcttgtgga actgaaaggc      60
gatgtgaacg gacacaaatt ttcggtacgt gggaaaggta aggcgatgc aacccgcgga     120
```

| | |
|---|---|
| aaactgaccc tcaaattcat tgcaccact ggcaagctgc ccgttccatg gccaaccta | 180 |
| gtgacaacct tgacctatgg cgttcagtgc ttctctcgtt atccgaaaca catgaaacgt | 240 |
| catgacttct ttaaatccgc gatgccgaaa ggctatgtgc aggaacgcac gatcagcttt | 300 |
| aagaaagacg gcaaatacaa gactcgcgcg gaagtcaagt ttgaaggacg tacgcttgtg | 360 |
| aatcgcatca aactgaaagg gcgcgatttc aaagagaaag gcaacattct gggccacaaa | 420 |
| ttacggtaca actttaacag tcacaaggtc tacattacgg ccgataaacg gaagaatggc | 480 |
| atcaaagcga aattcaaaat tcgtcacaat gtgaaggatg gtagcgttca actggccgat | 540 |
| cattaccagc agaatacgcc cattggtcgt ggtccggtat tgttaccgcg gaaccattat | 600 |
| ctgagtacac gctcaaaact gagcaaagac ccgaaagaaa agcgcgatca tatggtactg | 660 |
| ctggaatttg tcactgcagc tgggatcaag catggtcgcg atgagcgcta taaggtggc | 720 |
| tctggaggca ctggtggcag cggaggcacc ggtggaagtg gtggcacagg cggcgcgatg | 780 |
| gtggataccc tgagcggcct gagcagcgaa cagggccaga gcggcgatat gaccattgaa | 840 |
| gaagatagcg cgacccatat taaatttagc aaacgcgatg aagatggcaa agaactggcg | 900 |
| ggcgcgacca tggaactgcg cgatagcagc ggcaaaacca ttagcacctg gattagcgat | 960 |
| ggccaggtga aagattttta tctgtatccg ggcaaatata cctttgtgga aaccgcggcg | 1020 |
| ccggatggct atgaagtggc gaccgcgatt acctttaccg tgaacgaaca gggccaggtg | 1080 |
| accgtgaacg gcaaagcgac caaaggcgat gcgcatatt | 1119 |

<210> SEQ ID NO 8
<211> LENGTH: 765
<212> TYPE: DNA
<213> ORGANISM: Artificial Sequence
<220> FEATURE:
<223> OTHER INFORMATION: Synthetic gene sequence

<400> SEQUENCE: 8

| | |
|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |
| cgcccctacg agggcaccca gaccgccaag ctgaaggtga ccaagggtgg ccccctgccc | 180 |
| ttcgcctggg acatcctgtc ccctcagttc atgtacggct ccaaggccta cgtgaagcac | 240 |
| cccgccgaca tccccgacta cttgaagctg tccttcccg agggcttcaa gtgggagcgc | 300 |
| gtgatgaact tcgaggacgg cggcgtggtg accgtgaccc aggactcctc cctgcaggac | 360 |
| ggcgagttca tctacaaggt gaagctgcgc ggcaccaact cccctccga cggccccgta | 420 |
| atgcagaaga gaccatggg ctgggaggcc tcctccgagc ggatgtaccc cgaggacggc | 480 |
| gccctgaagg gcgagatcaa gcagaggctg aagctgaagg acggcggcca ctacgacgct | 540 |
| gaggtcaaga ccacctacaa ggccaagaag cccgtgcagc tgcccggcgc ctacaacgtc | 600 |
| aacatcaagt tggacatcac ctcccacaac gaggactaca ccatcgtgga acagtacgaa | 660 |
| cgcgccgagg gccgccactc caccggcggc atggacgagc tgtacaaggg tggtagcggt | 720 |
| ggcaccgcac atattgttat ggttgatgca tataaaccga ccaaa | 765 |

<210> SEQ ID NO 9
<211> LENGTH: 2394
<212> TYPE: DNA
<213> ORGANISM: Artificial Sequence
<220> FEATURE:
<223> OTHER INFORMATION: Synthetic gene sequence -continued

<400> SEQUENCE: 9

```
atggatgaaa caagtgcgag tggggtacag aacgaagttg ctcgtgccga tttggcggaa      60
tccccggcta ccgccaccgc gcccgtcgcg tctgaagcct cccagaatgc ggaaaccaca     120
gtggctgcga ccgctactga agccccgcag accgcggaaa acactgctcc taccaacagt     180
gccagtgaat caaccgaaaa accgatggac gaacagcctg tggcttctga accccacaa     240
ccaagcgtcg agaaaccggt attaccgacc gaggtgaaac cggcagagaa tacaactccg     300
gcaagtacgg aggccagtcc ggagacagtt tctccatcgc gcgcgacaga ccagcctgta     360
gccacccgtg attccgtgca gtctagccgt tcgcgccggt tgcgccgtga cctggaagct     420
accgctgtga cgccaggtac aggtccggct ggtgcggatg atgcaacacc gattcctcgt     480
gtcagcaaac cgaccctgtc agagtcagaa aaaaagaat ccacccaact ggcgaagcag     540
attaactggg tagacttctc cgacacagcg tcaatgaaga atttagatcc gcaaggagga     600
ttcaaagtag gtaccgtttt caaaaaggaa atctcgccgg ttatgtggt gacgctgacc      660
gttactgaac tgaaacccct caacagcacc gaaatttaca agaaacgcgt gaagggact      720
cccacggcaa atacctacga cccgaacgcg atcaatagct atctgaaagg ctataaagat     780
tacggtaaaa ccccgccgtc tgttacgggc cgcccgcaga acaaattttc aaccattggc     840
ggtcagggg tcgatacca aggtcgtaaa acgcagatca ttttgccgga cgacgcggtt      900
aattggggca tcaaatttaa ggtggaagca acctatcgcg aaatcctgt gaaaccttcg      960
gtcgttatgg ccgatgggga agatgccaat ccggctgaat atgggatttt cacgactaac    1020
ggtgaagggt gggagtatgt gggcgaatgg atgaaaggac cccgcgcgaa aggcccgtac    1080
actgtgatga ctgaagatat ggtgaaggca ttcgataaaa cccgcaaaga cggtctgctg    1140
atcctgaaag ataaaagcgt tgactggagc aaatacttgt ctccagacac agttactggt    1200
ggattaggta gccaggtgtt cggcccgatc atctcagcct caaaagcggt accggtggtt    1260
atgactcgcg gtgcgagcga agtcgggttt tatgtcgcca cgggtgggca acaagccctc    1320
atgatggggtt ttctcgttgt cgattcgagc gacgcaccag ccagctatgg cgaagcgtat    1380
catactattg gcacgcggga ttccattgcg aatacccga tcaatcagcc ttacttaggt     1440
agcaccgcag cagacattga tgcggactct gaaagtgact ggactgccga tgaccgcgaa    1500
gatgtagcag atgaaggccc cgcccagttg ctgacggctg accagcttag caaaaccaac    1560
gatttactgg acctgaacaa agccaagaac gggacctaca ccctcaaaat caaagcgaac    1620
ccaaacggta acgcaaaagc gtacgtcaag gcatgggtgg atttcaacaa caatggcaaa    1680
tttgatgaca atgaaggctc ggtggtgaag gagattaccg ccaacgggga tcatacgctg    1740
tcctttaacg ccattcctgg ccttaccggc ggcctggtgg accagattgg catgcgggta    1800
cgcattgcga cgaatgcagg ggatattgag aaaccgacag taccgcgtt cagtggggaa     1860
gtagaggata tgctggttcg ccgtgtctat ccgccacaag gcgaaaagca ggaatctact    1920
ggcttccaag gagaaaccca gaatgcttcg gtgcacttta ccgcaaaagg accggatcgc    1980
tccgattttg taaccaacgc gagcatgagc aatcaagcgc cacaggttct ggataatcag    2040
ggcaacgttc tgacgccgac caatggtaat acctatgtac gtcccgaggg aacgtacgtg    2100
gtgacagcca atggcgatga tgtcaacgtt acgttcactc cgaacgagga tttcagcggt    2160
gttgcggagg gtattaacat tcgtcgcact gactcaaatg gttccagcac gggttggcag    2220
tcgacggatg cagcagatcc gaataagaac gatcgcttga caacatggga cggccgtttt    2280
```

-continued

```
gtgccaaccg tccgcaaagt gcctaaatac gacagtacgg gcattcaggg ccaggatggt      2340
ggtagcggtg gcaccgcaca tattgttatg gttgatgcat ataaaccgac caaa           2394
```

<210> SEQ ID NO 10
<211> LENGTH: 341
<212> TYPE: PRT
<213> ORGANISM: Agrobacterium radiobacter

<400> SEQUENCE: 10

```
Met Ser Met Ala Arg Pro Ile Gly Thr Gly Asp Leu Ile Asn Thr Val
 1               5                  10                  15

Arg Gly Pro Ile Pro Val Ser Glu Ala Gly Phe Thr Leu Thr His Glu
             20                  25                  30

His Ile Cys Gly Ser Ser Ala Gly Phe Leu Arg Ala Trp Pro Glu Phe
         35                  40                  45

Phe Gly Ser Arg Lys Ala Leu Val Glu Lys Ala Val Arg Gly Leu Arg
     50                  55                  60

His Ala Arg Ala Ala Gly Val Gln Thr Ile Val Asp Val Ser Thr Phe
 65                  70                  75                  80

Asp Ile Gly Arg Asp Val Arg Leu Leu Ala Glu Val Ser Arg Ala Ala
                 85                  90                  95

Asp Val His Ile Val Ala Ala Thr Gly Leu Trp Phe Asp Pro Pro Leu
            100                 105                 110

Ser Met Arg Met Arg Ser Val Glu Glu Leu Thr Gln Phe Phe Leu Arg
        115                 120                 125

Glu Ile Gln His Gly Ile Glu Asp Thr Gly Ile Arg Ala Gly Ile Ile
130                 135                 140

Lys Val Ala Thr Thr Gly Lys Ala Thr Pro Phe Gln Glu Leu Val Leu
145                 150                 155                 160

Arg Ala Ala Ala Arg Ala Ser Leu Ala Thr Gly Val Pro Val Thr Thr
                165                 170                 175

His Thr Ser Ala Ser Gln Arg Asp Gly Glu Gln Gln Ala Ala Ile Phe
            180                 185                 190

Glu Ser Glu Gly Leu Ser Pro Ser Arg Val Cys Ile Gly His Ser Asp
        195                 200                 205

Asp Thr Asp Asp Leu Ser Tyr Leu Thr Gly Leu Ala Ala Arg Gly Tyr
    210                 215                 220

Leu Val Gly Leu Asp Arg Met Pro Tyr Ser Ala Ile Gly Leu Glu Gly
225                 230                 235                 240

Asn Ala Ser Ala Leu Ala Leu Phe Gly Thr Arg Ser Trp Gln Thr Arg
                245                 250                 255

Ala Leu Leu Ile Lys Ala Leu Ile Asp Arg Gly Tyr Lys Asp Arg Ile
            260                 265                 270

Leu Val Ser His Asp Trp Leu Phe Gly Phe Ser Ser Tyr Val Thr Asn
        275                 280                 285

Ile Met Asp Val Met Asp Arg Ile Asn Pro Asp Gly Met Ala Phe Val
    290                 295                 300

Pro Leu Arg Val Ile Pro Phe Leu Arg Glu Lys Gly Val Pro Pro Glu
305                 310                 315                 320

Thr Leu Ala Gly Val Thr Val Ala Asn Pro Ala Arg Phe Leu Ser Pro
                325                 330                 335

Thr Val Arg Ala Ser
            340
```

-continued

```
<210> SEQ ID NO 11
<211> LENGTH: 347
<212> TYPE: PRT
<213> ORGANISM: Artificial Sequence
<220> FEATURE:
<223> OTHER INFORMATION: Supercharged protein

<400> SEQUENCE: 11

Met His His His His His Ser Met Ala Arg Pro Ile Gly Thr Gly
1               5                   10                  15

Asp Leu Ile Asn Thr Val Arg Gly Pro Ile Pro Val Ser Glu Ala Gly
            20                  25                  30

Phe Thr Leu Thr His Glu His Ile Cys Gly Ser Ser Ala Gly Phe Leu
        35                  40                  45

Arg Ala Trp Pro Glu Phe Phe Gly Ser Arg Lys Ala Leu Val Glu Lys
    50                  55                  60

Ala Val Arg Gly Leu Arg His Ala Arg Ala Ala Gly Val Gln Thr Ile
65                  70                  75                  80

Val Lys Val Ser Thr Phe Asp Ile Gly Arg Asp Val Arg Leu Leu Ala
                85                  90                  95

Glu Val Ser Arg Ala Ala Lys Val His Ile Val Ala Ala Thr Gly Leu
            100                 105                 110

Trp Phe Lys Pro Pro Leu Ser Met Arg Met Arg Ser Val Lys Lys Leu
        115                 120                 125

Thr Gln Phe Phe Leu Arg Glu Ile Gln His Gly Ile Lys Lys Thr Gly
    130                 135                 140

Ile Arg Ala Gly Ile Ile Lys Val Ala Thr Thr Gly Lys Ala Thr Pro
145                 150                 155                 160

Phe Gln Glu Leu Val Leu Arg Ala Ala Arg Ala Ser Leu Ala Thr
                165                 170                 175

Gly Val Pro Val Thr Thr His Thr Ser Ala Ser Gln Arg Lys Gly Glu
            180                 185                 190

Gln Gln Ala Ala Ile Phe Glu Ser Glu Gly Leu Ser Pro Ser Arg Val
        195                 200                 205

Cys Ile Gly His Ser Asp Asp Thr Lys Lys Leu Ser Tyr Leu Thr Gly
    210                 215                 220

Leu Ala Ala Arg Gly Tyr Leu Val Gly Leu Asp Arg Met Pro Tyr Ser
225                 230                 235                 240

Ala Ile Gly Leu Lys Gly Asn Ala Ser Ala Leu Ala Leu Phe Gly Thr
                245                 250                 255

Arg Ser Trp Gln Thr Arg Ala Leu Leu Ile Lys Ala Leu Ile Asp Arg
            260                 265                 270

Gly Tyr Lys Asp Arg Ile Leu Val Ser His Asp Trp Leu Phe Gly Phe
        275                 280                 285

Ser Ser Tyr Val Thr Asn Ile Met Asp Val Met Asp Arg Ile Asn Pro
    290                 295                 300

Asp Gly Met Ala Phe Val Pro Leu Arg Val Ile Pro Phe Leu Arg Glu
305                 310                 315                 320

Lys Gly Val Pro Pro Glu Thr Leu Ala Gly Val Thr Val Ala Asn Pro
                325                 330                 335

Ala Arg Phe Leu Ser Pro Thr Val Arg Ala Ser
            340                 345

<210> SEQ ID NO 12
<211> LENGTH: 238
<212> TYPE: PRT
```

<213> ORGANISM: Artificial Sequence
<220> FEATURE:
<223> OTHER INFORMATION: Supercharged protein

<400> SEQUENCE: 12

```
Ala Ser Lys Gly Glu Arg Leu Phe Arg Gly Lys Val Pro Ile Leu Val
1               5                   10                  15

Glu Leu Lys Gly Asp Val Asn Gly His Lys Phe Ser Val Arg Gly Lys
            20                  25                  30

Gly Lys Gly Asp Ala Thr Arg Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Lys His Met Lys Arg
65                  70                  75                  80

His Asp Phe Phe Lys Ser Ala Met Pro Lys Gly Tyr Val Gln Glu Arg
                85                  90                  95

Thr Ile Ser Phe Lys Lys Asp Gly Lys Tyr Lys Thr Arg Ala Glu Val
            100                 105                 110

Lys Phe Glu Gly Arg Thr Leu Val Asn Arg Ile Lys Leu Lys Gly Arg
        115                 120                 125

Asp Phe Lys Glu Lys Gly Asn Ile Leu Gly His Lys Leu Arg Tyr Asn
130                 135                 140

Phe Asn Ser His Lys Val Tyr Ile Thr Ala Asp Lys Arg Lys Asn Gly
145                 150                 155                 160

Ile Lys Ala Lys Phe Lys Ile Arg His Asn Val Lys Asp Gly Ser Val
                165                 170                 175

Gln Leu Ala Asp His Tyr Gln Gln Asn Thr Pro Ile Gly Arg Gly Pro
            180                 185                 190

Val Leu Leu Pro Arg Asn His Tyr Leu Ser Thr Arg Ser Lys Leu Ser
        195                 200                 205

Lys Asp Pro Lys Glu Lys Arg Asp His Met Val Leu Leu Glu Phe Val
    210                 215                 220

Thr Ala Ala Gly Ile Lys His Gly Arg Asp Glu Arg Tyr Lys
225                 230                 235
```

<210> SEQ ID NO 13
<211> LENGTH: 598
<212> TYPE: PRT
<213> ORGANISM: Artificial Sequence
<220> FEATURE:
<223> OTHER INFORMATION: Fusion protein

<400> SEQUENCE: 13

```
Ala Ser Lys Gly Glu Arg Leu Phe Arg Gly Lys Val Pro Ile Leu Val
1               5                   10                  15

Glu Leu Lys Gly Asp Val Asn Gly His Lys Phe Ser Val Arg Gly Lys
            20                  25                  30

Gly Lys Gly Asp Ala Thr Arg Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Lys His Met Lys Arg
65                  70                  75                  80

His Asp Phe Phe Lys Ser Ala Met Pro Lys Gly Tyr Val Gln Glu Arg
                85                  90                  95
```

```
Thr Ile Ser Phe Lys Lys Asp Gly Lys Tyr Lys Thr Arg Ala Glu Val
            100                 105                 110

Lys Phe Glu Gly Arg Thr Leu Val Asn Arg Ile Lys Leu Lys Gly Arg
        115                 120                 125

Asp Phe Lys Glu Lys Gly Asn Ile Leu Gly His Lys Leu Arg Tyr Asn
    130                 135                 140

Phe Asn Ser His Lys Val Tyr Ile Thr Ala Asp Lys Arg Lys Asn Gly
145                 150                 155                 160

Ile Lys Ala Lys Phe Lys Ile Arg His Asn Val Lys Asp Gly Ser Val
                165                 170                 175

Gln Leu Ala Asp His Tyr Gln Gln Asn Thr Pro Ile Gly Arg Gly Pro
            180                 185                 190

Val Leu Leu Pro Arg Asn His Tyr Leu Ser Thr Arg Ser Lys Leu Ser
        195                 200                 205

Lys Asp Pro Lys Glu Lys Arg Asp His Met Val Leu Leu Glu Phe Val
    210                 215                 220

Thr Ala Ala Gly Ile Lys His Gly Arg Asp Glu Arg Tyr Lys Gly Ser
225                 230                 235                 240

Glu Ala Ala Ala Lys Glu Ala Ala Lys Glu Ala Ala Lys Gly
                245                 250                 255

Ser Met Ser Met Ala Arg Pro Ile Gly Thr Gly Asp Leu Ile Asn Thr
            260                 265                 270

Val Arg Gly Pro Ile Pro Val Ser Glu Ala Gly Phe Thr Leu Thr His
        275                 280                 285

Glu His Ile Cys Gly Ser Ser Ala Gly Phe Leu Arg Ala Trp Pro Glu
    290                 295                 300

Phe Phe Gly Ser Arg Lys Ala Leu Val Glu Lys Ala Val Arg Gly Leu
305                 310                 315                 320

Arg His Ala Arg Ala Ala Gly Val Gln Thr Ile Val Asp Val Ser Thr
                325                 330                 335

Phe Asp Ile Gly Arg Asp Val Arg Leu Leu Ala Glu Val Ser Arg Ala
            340                 345                 350

Ala Asp Val His Ile Val Ala Ala Thr Gly Leu Trp Phe Asp Pro Pro
        355                 360                 365

Leu Ser Met Arg Met Arg Ser Val Glu Glu Leu Thr Gln Phe Phe Leu
    370                 375                 380

Arg Glu Ile Gln His Gly Ile Glu Asp Thr Gly Ile Arg Ala Gly Ile
385                 390                 395                 400

Ile Lys Val Ala Thr Thr Gly Lys Ala Thr Pro Phe Gln Glu Leu Val
                405                 410                 415

Leu Arg Ala Ala Ala Arg Ala Ser Leu Ala Thr Gly Val Pro Val Thr
            420                 425                 430

Thr His Thr Ser Ala Ser Gln Arg Asp Gly Glu Gln Gln Ala Ala Ile
        435                 440                 445

Phe Glu Ser Glu Gly Leu Ser Pro Ser Arg Val Cys Ile Gly His Ser
    450                 455                 460

Asp Asp Thr Asp Asp Leu Ser Tyr Leu Thr Gly Leu Ala Ala Arg Gly
465                 470                 475                 480

Tyr Leu Val Gly Leu Asp Arg Met Pro Tyr Ser Ala Ile Gly Leu Glu
                485                 490                 495

Gly Asn Ala Ser Ala Leu Ala Leu Phe Gly Thr Arg Ser Trp Gln Thr
            500                 505                 510
```

```
Arg Ala Leu Leu Ile Lys Ala Leu Ile Asp Arg Gly Tyr Lys Asp Arg
            515                 520                 525

Ile Leu Val Ser His Asp Trp Leu Phe Gly Phe Ser Ser Tyr Val Thr
            530                 535                 540

Asn Ile Met Asp Val Met Asp Arg Ile Asn Pro Asp Gly Met Ala Phe
545                 550                 555                 560

Val Pro Leu Arg Val Ile Pro Phe Leu Arg Glu Lys Gly Val Pro Pro
                565                 570                 575

Glu Thr Leu Ala Gly Val Thr Val Ala Asn Pro Ala Arg Phe Leu Ser
            580                 585                 590

Pro Thr Val Arg Ala Ser
            595

<210> SEQ ID NO 14
<211> LENGTH: 1018
<212> TYPE: PRT
<213> ORGANISM: Artificial Sequence
<220> FEATURE:
<223> OTHER INFORMATION: Fusion protein

<400> SEQUENCE: 14

Met Asp Glu Thr Ser Ala Ser Gly Val Gln Asn Glu Val Ala Arg Ala
1               5                   10                  15

Asp Leu Ala Glu Ser Pro Ala Thr Ala Thr Pro Val Ala Ser Glu
            20                  25                  30

Ala Ser Gln Asn Ala Glu Thr Thr Val Ala Ala Thr Ala Thr Glu Ala
            35                  40                  45

Pro Gln Thr Ala Glu Asn Thr Ala Pro Thr Asn Ser Ala Ser Glu Ser
    50                  55                  60

Thr Glu Lys Pro Met Asp Glu Gln Pro Val Ala Ser Glu Thr Pro Gln
65                  70                  75                  80

Pro Ser Val Glu Lys Pro Val Leu Pro Thr Glu Val Lys Pro Ala Glu
                85                  90                  95

Asn Thr Thr Pro Ala Ser Thr Glu Ala Ser Pro Glu Thr Val Ser Pro
            100                 105                 110

Ser Arg Ala Thr Asp Gln Pro Val Ala Thr Arg Asp Ser Val Gln Ser
            115                 120                 125

Ser Arg Ser Arg Arg Leu Arg Arg Asp Leu Glu Ala Thr Ala Val Thr
    130                 135                 140

Pro Gly Thr Gly Pro Ala Gly Ala Asp Asp Ala Thr Pro Ile Pro Arg
145                 150                 155                 160

Val Ser Lys Pro Thr Leu Ser Glu Ser Glu Lys Lys Glu Ser Thr Gln
                165                 170                 175

Leu Ala Lys Gln Ile Asn Trp Val Asp Phe Ser Asp Thr Ala Ser Met
            180                 185                 190

Lys Asn Leu Asp Pro Gln Gly Gly Phe Lys Val Gly Thr Val Phe Lys
            195                 200                 205

Lys Glu Ile Ser Pro Gly Tyr Val Val Thr Leu Thr Val Thr Glu Leu
    210                 215                 220

Lys Pro Phe Asn Ser Thr Glu Ile Tyr Lys Arg Val Glu Gly Thr
225                 230                 235                 240

Pro Thr Ala Asn Thr Tyr Asp Pro Asn Ala Ile Asn Ser Tyr Leu Lys
                245                 250                 255

Gly Tyr Lys Asp Tyr Gly Lys Thr Pro Pro Ser Val Thr Gly Arg Pro
            260                 265                 270
```

```
Gln Asn Lys Phe Ser Thr Ile Gly Gly Gln Gly Phe Asp Thr Gln Gly
            275                 280                 285

Arg Lys Thr Gln Ile Ile Leu Pro Asp Asp Ala Val Asn Trp Gly Ile
290                 295                 300

Lys Phe Lys Val Glu Ala Thr Tyr Arg Gly Asn Pro Val Lys Pro Ser
305                 310                 315                 320

Val Val Met Ala Asp Gly Glu Asp Ala Asn Pro Ala Glu Tyr Gly Ile
                325                 330                 335

Phe Thr Thr Asn Gly Glu Gly Trp Glu Tyr Val Gly Glu Trp Met Lys
            340                 345                 350

Gly Pro Arg Ala Lys Gly Pro Tyr Thr Val Met Thr Glu Asp Met Val
        355                 360                 365

Lys Ala Phe Asp Lys Thr Arg Lys Asp Gly Leu Leu Ile Leu Lys Asp
370                 375                 380

Lys Ser Val Asp Trp Ser Lys Tyr Leu Ser Pro Asp Thr Val Thr Gly
385                 390                 395                 400

Gly Leu Gly Ser Gln Val Phe Gly Pro Ile Ile Ser Ala Ser Lys Ala
                405                 410                 415

Val Pro Val Met Thr Arg Gly Ala Ser Glu Val Gly Phe Tyr Val
            420                 425                 430

Ala Thr Gly Gly Gln Gln Ala Leu Met Met Gly Phe Leu Val Val Asp
        435                 440                 445

Ser Ser Asp Ala Pro Ala Ser Tyr Gly Glu Ala Tyr His Thr Ile Gly
    450                 455                 460

Thr Arg Asp Ser Ile Ala Asn Thr Pro Ile Asn Gln Pro Tyr Leu Gly
465                 470                 475                 480

Ser Thr Ala Ala Asp Ile Asp Ala Asp Ser Glu Ser Asp Trp Thr Ala
                485                 490                 495

Asp Asp Arg Glu Asp Val Ala Asp Glu Gly Pro Ala Gln Leu Leu Thr
            500                 505                 510

Ala Asp Gln Leu Ser Lys Thr Asn Asp Leu Leu Asp Leu Asn Lys Ala
        515                 520                 525

Lys Asn Gly Thr Tyr Thr Leu Lys Ile Lys Ala Asn Pro Asn Gly Asn
    530                 535                 540

Ala Lys Ala Tyr Val Lys Ala Trp Val Asp Phe Asn Asn Gly Lys
545                 550                 555                 560

Phe Asp Asp Asn Glu Gly Ser Val Val Lys Glu Ile Thr Ala Asn Gly
                565                 570                 575

Asp His Thr Leu Ser Phe Asn Ala Ile Pro Gly Leu Thr Gly Gly Leu
            580                 585                 590

Val Asp Gln Ile Gly Met Arg Val Arg Ile Ala Thr Asn Ala Gly Asp
        595                 600                 605

Ile Glu Lys Pro Thr Gly Thr Ala Phe Ser Gly Glu Val Glu Asp Met
    610                 615                 620

Leu Val Arg Arg Val Tyr Pro Pro Gln Gly Lys Gln Glu Ser Thr
625                 630                 635                 640

Gly Phe Gln Gly Glu Thr Gln Asn Ala Ser Val His Phe Thr Ala Lys
                645                 650                 655

Gly Pro Asp Arg Ser Asp Phe Val Thr Asn Ala Ser Met Ser Asn Gln
            660                 665                 670

Ala Pro Gln Val Leu Asp Asn Gln Gly Asn Val Leu Thr Pro Thr Asn
        675                 680                 685
```

Gly Asn Thr Tyr Val Arg Pro Glu Gly Thr Tyr Val Val Thr Ala Asn
    690                 695                 700

Gly Asp Asp Val Asn Val Thr Phe Thr Pro Asn Glu Asp Phe Ser Gly
705                 710                 715                 720

Val Ala Glu Gly Ile Asn Ile Arg Arg Thr Asp Ser Asn Gly Ser Ser
                725                 730                 735

Thr Gly Trp Gln Ser Thr Asp Ala Ala Asp Pro Asn Lys Asn Asp Arg
            740                 745                 750

Leu Asn Asn Met Asp Gly Arg Phe Val Pro Thr Val Arg Lys Val Pro
        755                 760                 765

Lys Tyr Asp Ser Thr Gly Ile Gln Gly Gln Asp Met Ala Ser Lys Gly
    770                 775                 780

Glu Arg Leu Phe Arg Gly Lys Val Pro Ile Leu Val Glu Leu Lys Gly
785                 790                 795                 800

Asp Val Asn Gly His Lys Phe Ser Val Arg Gly Lys Gly Lys Gly Asp
                805                 810                 815

Ala Thr Arg Gly Lys Leu Thr Leu Lys Phe Ile Cys Thr Thr Gly Lys
            820                 825                 830

Leu Pro Val Pro Trp Pro Thr Leu Val Thr Thr Leu Thr Tyr Gly Val
        835                 840                 845

Gln Cys Phe Ser Arg Tyr Pro Lys His Met Lys Arg His Asp Phe Phe
    850                 855                 860

Lys Ser Ala Met Pro Lys Gly Tyr Val Gln Glu Arg Thr Ile Ser Phe
865                 870                 875                 880

Lys Lys Asp Gly Lys Tyr Lys Thr Arg Ala Glu Val Lys Phe Glu Gly
                885                 890                 895

Arg Thr Leu Val Asn Arg Ile Lys Leu Lys Gly Arg Asp Phe Lys Glu
            900                 905                 910

Lys Gly Asn Ile Leu Gly His Lys Leu Arg Tyr Asn Phe Asn Ser His
        915                 920                 925

Lys Val Tyr Ile Thr Ala Asp Lys Arg Lys Asn Gly Ile Lys Ala Lys
    930                 935                 940

Phe Lys Ile Arg His Asn Val Lys Asp Gly Ser Val Gln Leu Ala Asp
945                 950                 955                 960

His Tyr Gln Gln Asn Thr Pro Ile Gly Arg Gly Pro Val Leu Leu Pro
                965                 970                 975

Arg Asn His Tyr Leu Ser Thr Arg Ser Lys Leu Ser Lys Asp Pro Lys
            980                 985                 990

Glu Lys Arg Asp His Met Val Leu Leu Glu Phe Val Thr Ala Ala Gly
        995                 1000                1005

Ile Lys His Gly Arg Asp Glu Arg Tyr Lys
    1010                1015

<210> SEQ ID NO 15
<211> LENGTH: 259
<212> TYPE: PRT
<213> ORGANISM: Artificial Sequence
<220> FEATURE:
<223> OTHER INFORMATION: Fusion protein

<400> SEQUENCE: 15

Ala Ser Lys Gly Glu Arg Leu Phe Arg Gly Lys Val Pro Ile Leu Val
1               5                   10                  15

Glu Leu Lys Gly Asp Val Asn Gly His Lys Phe Ser Val Arg Gly Lys
                20                  25                  30

```
Gly Lys Gly Asp Ala Thr Arg Gly Lys Leu Thr Leu Lys Phe Ile Cys
            35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Lys His Met Lys Arg
 65                  70                  75                  80

His Asp Phe Phe Lys Ser Ala Met Pro Lys Gly Tyr Val Gln Glu Arg
                85                  90                  95

Thr Ile Ser Phe Lys Lys Asp Gly Lys Tyr Lys Thr Arg Ala Glu Val
            100                 105                 110

Lys Phe Glu Gly Arg Thr Leu Val Asn Arg Ile Lys Leu Lys Gly Arg
        115                 120                 125

Asp Phe Lys Glu Lys Gly Asn Ile Leu Gly His Lys Leu Arg Tyr Asn
    130                 135                 140

Phe Asn Ser His Lys Val Tyr Ile Thr Ala Asp Lys Arg Lys Asn Gly
145                 150                 155                 160

Ile Lys Ala Lys Phe Lys Ile Arg His Asn Val Lys Asp Gly Ser Val
                165                 170                 175

Gln Leu Ala Asp His Tyr Gln Gln Asn Thr Pro Ile Gly Arg Gly Pro
            180                 185                 190

Val Leu Leu Pro Arg Asn His Tyr Leu Ser Thr Arg Ser Lys Leu Ser
        195                 200                 205

Lys Asp Pro Lys Glu Lys Arg Asp His Met Val Leu Leu Glu Phe Val
    210                 215                 220

Thr Ala Ala Gly Ile Lys His Gly Arg Asp Glu Arg Tyr Lys Arg Arg
225                 230                 235                 240

Pro Lys Gly Arg Gly Lys Arg Arg Glu Lys Gln Arg Pro Thr Asp
                245                 250                 255

Cys His Leu

<210> SEQ ID NO 16
<211> LENGTH: 1018
<212> TYPE: PRT
<213> ORGANISM: Artificial Sequence
<220> FEATURE:
<223> OTHER INFORMATION: Fusion protein

<400> SEQUENCE: 16

Met Asp Glu Thr Ser Ala Ser Gly Val Gln Asn Glu Val Ala Arg Ala
 1               5                  10                  15

Asp Leu Ala Glu Ser Pro Ala Thr Ala Thr Pro Val Ala Ser Glu
             20                 25                  30

Ala Ser Gln Asn Ala Glu Thr Thr Val Ala Ala Thr Ala Thr Glu Ala
             35                  40                 45

Pro Gln Thr Ala Glu Asn Thr Ala Pro Thr Asn Ser Ala Ser Glu Ser
    50                  55                  60

Thr Glu Lys Pro Met Asp Glu Gln Pro Val Ala Ser Glu Thr Pro Gln
 65                  70                  75                  80

Pro Ser Val Glu Lys Pro Val Leu Pro Thr Glu Val Lys Pro Ala Glu
                 85                  90                  95

Asn Thr Thr Pro Ala Ser Thr Glu Ala Ser Pro Glu Thr Val Ser Pro
            100                 105                 110

Ser Arg Ala Thr Asp Gln Pro Val Ala Thr Arg Asp Ser Val Gln Ser
        115                 120                 125
```

-continued

```
Ser Arg Ser Arg Arg Leu Arg Arg Asp Leu Glu Ala Thr Ala Val Thr
    130                 135                 140

Pro Gly Thr Gly Pro Ala Gly Ala Asp Asp Ala Thr Pro Ile Pro Arg
145                 150                 155                 160

Val Ser Lys Pro Thr Leu Ser Glu Ser Glu Lys Lys Glu Ser Thr Gln
                165                 170                 175

Leu Ala Lys Gln Ile Asn Trp Val Asp Phe Ser Asp Thr Ala Ser Met
            180                 185                 190

Lys Asn Leu Asp Pro Gln Gly Gly Phe Lys Val Gly Thr Val Phe Lys
        195                 200                 205

Lys Glu Ile Ser Pro Gly Tyr Val Val Thr Leu Thr Val Thr Glu Leu
    210                 215                 220

Lys Pro Phe Asn Ser Thr Glu Ile Tyr Lys Lys Arg Val Glu Gly Thr
225                 230                 235                 240

Pro Thr Ala Asn Thr Tyr Asp Pro Asn Ala Ile Asn Ser Tyr Leu Lys
                245                 250                 255

Gly Tyr Lys Asp Tyr Gly Lys Thr Pro Pro Ser Val Thr Gly Arg Pro
            260                 265                 270

Gln Asn Lys Phe Ser Thr Ile Gly Gly Gln Gly Phe Asp Thr Gln Gly
        275                 280                 285

Arg Lys Thr Gln Ile Ile Leu Pro Asp Asp Ala Val Asn Trp Gly Ile
    290                 295                 300

Lys Phe Lys Val Glu Ala Thr Tyr Arg Gly Asn Pro Val Lys Pro Ser
305                 310                 315                 320

Val Val Met Ala Asp Gly Glu Asp Ala Asn Pro Ala Glu Tyr Gly Ile
                325                 330                 335

Phe Thr Thr Asn Gly Glu Gly Trp Glu Tyr Val Gly Glu Trp Met Lys
            340                 345                 350

Gly Pro Arg Ala Lys Gly Pro Tyr Thr Val Met Thr Glu Asp Met Val
        355                 360                 365

Lys Ala Phe Asp Lys Thr Arg Lys Asp Gly Leu Leu Ile Leu Lys Asp
    370                 375                 380

Lys Ser Val Asp Trp Ser Lys Tyr Leu Ser Pro Asp Thr Val Thr Gly
385                 390                 395                 400

Gly Leu Gly Ser Gln Val Phe Gly Pro Ile Ile Ser Ala Ser Lys Ala
                405                 410                 415

Val Pro Val Val Met Thr Arg Gly Ala Ser Glu Val Gly Phe Tyr Val
            420                 425                 430

Ala Thr Gly Gly Gln Gln Ala Leu Met Met Gly Phe Leu Val Val Asp
        435                 440                 445

Ser Ser Asp Ala Pro Ala Ser Tyr Gly Glu Ala Tyr His Thr Ile Gly
    450                 455                 460

Thr Arg Asp Ser Ile Ala Asn Thr Pro Ile Asn Gln Pro Tyr Leu Gly
465                 470                 475                 480

Ser Thr Ala Ala Asp Ile Asp Ala Asp Ser Glu Ser Asp Trp Thr Ala
                485                 490                 495

Asp Asp Arg Glu Asp Val Ala Asp Glu Gly Pro Ala Gln Leu Leu Thr
            500                 505                 510

Ala Asp Gln Leu Ser Lys Thr Asn Asp Leu Leu Asp Leu Asn Lys Ala
        515                 520                 525

Lys Asn Gly Thr Tyr Thr Leu Lys Ile Lys Ala Asn Pro Asn Gly Asn
    530                 535                 540
```

```
Ala Lys Ala Tyr Val Lys Ala Trp Val Asp Phe Asn Asn Asn Gly Lys
545                 550                 555                 560

Phe Asp Asp Asn Glu Gly Ser Val Val Lys Glu Ile Thr Ala Asn Gly
                565                 570                 575

Asp His Thr Leu Ser Phe Asn Ala Ile Pro Gly Leu Thr Gly Gly Leu
            580                 585                 590

Val Asp Gln Ile Gly Met Arg Val Arg Ile Ala Thr Asn Ala Gly Asp
        595                 600                 605

Ile Glu Lys Pro Thr Gly Thr Ala Phe Ser Gly Val Glu Asp Met
610                 615                 620

Leu Val Arg Arg Val Tyr Pro Pro Gln Gly Glu Lys Gln Glu Ser Thr
625                 630                 635                 640

Gly Phe Gln Gly Glu Thr Gln Asn Ala Ser Val His Phe Thr Ala Lys
                645                 650                 655

Gly Pro Asp Arg Ser Asp Phe Val Thr Asn Ala Ser Met Ser Asn Gln
                660                 665                 670

Ala Pro Gln Val Leu Asp Asn Gln Gly Asn Val Leu Thr Pro Thr Asn
            675                 680                 685

Gly Asn Thr Tyr Val Arg Pro Glu Gly Thr Tyr Val Val Thr Ala Asn
690                 695                 700

Gly Asp Asp Val Asn Val Thr Phe Thr Pro Asn Glu Asp Phe Ser Gly
705                 710                 715                 720

Val Ala Glu Gly Ile Asn Ile Arg Arg Thr Asp Ser Asn Gly Ser Ser
                725                 730                 735

Thr Gly Trp Gln Ser Thr Asp Ala Ala Asp Pro Asn Lys Asn Asp Arg
                740                 745                 750

Leu Asn Asn Met Asp Gly Arg Phe Val Pro Thr Val Arg Lys Val Pro
                755                 760                 765

Lys Tyr Asp Ser Thr Gly Ile Gln Gly Gln Asp Met Ala Ser Lys Gly
        770                 775                 780

Glu Arg Leu Phe Arg Gly Lys Val Pro Ile Leu Val Glu Leu Lys Gly
785                 790                 795                 800

Asp Val Asn Gly His Lys Phe Ser Val Arg Gly Lys Gly Lys Gly Asp
                805                 810                 815

Ala Thr Arg Gly Lys Leu Thr Leu Lys Phe Ile Cys Thr Thr Gly Lys
                820                 825                 830

Leu Pro Val Pro Trp Pro Thr Leu Val Thr Thr Leu Thr Tyr Gly Val
            835                 840                 845

Gln Cys Phe Ser Arg Tyr Pro Lys His Met Lys Arg His Asp Phe Phe
850                 855                 860

Lys Ser Ala Met Pro Lys Gly Tyr Val Gln Glu Arg Thr Ile Ser Phe
865                 870                 875                 880

Lys Lys Asp Gly Lys Tyr Lys Thr Arg Ala Glu Val Lys Phe Glu Gly
                885                 890                 895

Arg Thr Leu Val Asn Arg Ile Lys Leu Lys Gly Arg Asp Phe Lys Glu
            900                 905                 910

Lys Gly Asn Ile Leu Gly His Lys Leu Arg Tyr Asn Phe Asn Ser His
            915                 920                 925

Lys Val Tyr Ile Thr Ala Asp Lys Arg Lys Asn Gly Ile Lys Ala Lys
        930                 935                 940

Phe Lys Ile Arg His Asn Val Lys Asp Gly Ser Val Gln Leu Ala Asp
945                 950                 955                 960
```

-continued

```
His Tyr Gln Gln Asn Thr Pro Ile Gly Arg Gly Pro Val Leu Leu Pro
                965                 970                 975

Arg Asn His Tyr Leu Ser Thr Arg Ser Lys Leu Ser Lys Asp Pro Lys
            980                 985                 990

Glu Lys Arg Asp His Met Val Leu Leu Glu Phe Val Thr Ala Ala Gly
        995                1000                1005

Ile Lys His Gly Arg Asp Glu Arg Tyr Lys
    1010                1015
```

<210> SEQ ID NO 17
<211> LENGTH: 255
<212> TYPE: PRT
<213> ORGANISM: Artificial Sequence
<220> FEATURE:
<223> OTHER INFORMATION: Artificial construct

<400> SEQUENCE: 17

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Gly Gly Ser Gly
225                 230                 235                 240

Gly Thr Ala His Ile Val Met Val Asp Ala Tyr Lys Pro Thr Lys
                245                 250                 255
```

<210> SEQ ID NO 18
<211> LENGTH: 798
<212> TYPE: PRT
<213> ORGANISM: Artificial Sequence
<220> FEATURE:
<223> OTHER INFORMATION: Artificial construct

<400> SEQUENCE: 18

```
Met Asp Glu Thr Ser Ala Ser Gly Val Gln Asn Glu Val Ala Arg Ala
1               5                   10                  15

Asp Leu Ala Glu Ser Pro Ala Thr Ala Pro Val Ala Ser Glu
            20                  25                  30

Ala Ser Gln Asn Ala Glu Thr Thr Val Ala Ala Thr Ala Thr Glu Ala
                35                  40                  45

Pro Gln Thr Ala Glu Asn Thr Ala Pro Thr Asn Ser Ala Ser Glu Ser
            50                  55                  60

Thr Glu Lys Pro Met Asp Glu Gln Pro Val Ala Ser Glu Thr Pro Gln
65                  70                  75                  80

Pro Ser Val Glu Lys Pro Val Leu Pro Thr Glu Val Lys Pro Ala Glu
                85                  90                  95

Asn Thr Thr Pro Ala Ser Thr Glu Ala Ser Pro Glu Thr Val Ser Pro
                100                 105                 110

Ser Arg Ala Thr Asp Gln Pro Val Ala Thr Arg Asp Ser Val Gln Ser
            115                 120                 125

Ser Arg Ser Arg Arg Leu Arg Arg Asp Leu Glu Ala Thr Ala Val Thr
130                 135                 140

Pro Gly Thr Gly Pro Ala Gly Ala Asp Asp Ala Thr Pro Ile Pro Arg
145                 150                 155                 160

Val Ser Lys Pro Thr Leu Ser Glu Ser Glu Lys Lys Glu Ser Thr Gln
                165                 170                 175

Leu Ala Lys Gln Ile Asn Trp Val Asp Phe Ser Asp Thr Ala Ser Met
            180                 185                 190

Lys Asn Leu Asp Pro Gln Gly Gly Phe Lys Val Gly Thr Val Phe Lys
            195                 200                 205

Lys Glu Ile Ser Pro Gly Tyr Val Val Thr Leu Thr Val Thr Glu Leu
210                 215                 220

Lys Pro Phe Asn Ser Thr Glu Ile Tyr Lys Lys Arg Val Glu Gly Thr
225                 230                 235                 240

Pro Thr Ala Asn Thr Tyr Asp Pro Asn Ala Ile Asn Ser Tyr Leu Lys
                245                 250                 255

Gly Tyr Lys Asp Tyr Gly Lys Thr Pro Pro Ser Val Thr Gly Arg Pro
            260                 265                 270

Gln Asn Lys Phe Ser Thr Ile Gly Gly Gln Gly Phe Asp Thr Gln Gly
            275                 280                 285

Arg Lys Thr Gln Ile Ile Leu Pro Asp Asp Ala Val Asn Trp Gly Ile
290                 295                 300

Lys Phe Lys Val Glu Ala Thr Tyr Arg Gly Asn Pro Val Lys Pro Ser
305                 310                 315                 320

Val Val Met Ala Asp Gly Glu Asp Ala Asn Pro Ala Glu Tyr Gly Ile
                325                 330                 335

Phe Thr Thr Asn Gly Glu Gly Trp Glu Tyr Val Gly Glu Trp Met Lys
            340                 345                 350

Gly Pro Arg Ala Lys Gly Pro Tyr Thr Val Met Thr Glu Asp Met Val
            355                 360                 365

Lys Ala Phe Asp Lys Thr Arg Lys Asp Gly Leu Leu Ile Leu Lys Asp
370                 375                 380

Lys Ser Val Asp Trp Ser Lys Tyr Leu Ser Pro Asp Thr Val Thr Gly
385                 390                 395                 400

Gly Leu Gly Ser Gln Val Phe Gly Pro Ile Ile Ser Ala Ser Lys Ala
            405                 410                 415
```

```
Val Pro Val Val Met Thr Arg Gly Ala Ser Glu Val Gly Phe Tyr Val
            420                 425                 430
Ala Thr Gly Gly Gln Gln Ala Leu Met Met Gly Phe Leu Val Val Asp
        435                 440                 445
Ser Ser Asp Ala Pro Ala Ser Tyr Gly Glu Ala Tyr His Thr Ile Gly
450                 455                 460
Thr Arg Asp Ser Ile Ala Asn Thr Pro Ile Asn Gln Pro Tyr Leu Gly
465                 470                 475                 480
Ser Thr Ala Ala Asp Ile Asp Ala Asp Ser Glu Ser Asp Trp Thr Ala
                485                 490                 495
Asp Asp Arg Glu Asp Val Ala Asp Glu Gly Pro Ala Gln Leu Leu Thr
            500                 505                 510
Ala Asp Gln Leu Ser Lys Thr Asn Asp Leu Leu Asp Leu Asn Lys Ala
        515                 520                 525
Lys Asn Gly Thr Tyr Thr Leu Lys Ile Lys Ala Asn Pro Asn Gly Asn
530                 535                 540
Ala Lys Ala Tyr Val Lys Ala Trp Val Asp Phe Asn Asn Asn Gly Lys
545                 550                 555                 560
Phe Asp Asp Asn Glu Gly Ser Val Val Lys Glu Ile Thr Ala Asn Gly
                565                 570                 575
Asp His Thr Leu Ser Phe Asn Ala Ile Pro Gly Leu Thr Gly Gly Leu
            580                 585                 590
Val Asp Gln Ile Gly Met Arg Val Arg Ile Ala Thr Asn Ala Gly Asp
        595                 600                 605
Ile Glu Lys Pro Thr Gly Thr Ala Phe Ser Gly Glu Val Glu Asp Met
610                 615                 620
Leu Val Arg Arg Val Tyr Pro Pro Gln Gly Glu Lys Gln Glu Ser Thr
625                 630                 635                 640
Gly Phe Gln Gly Glu Thr Gln Asn Ala Ser Val His Phe Thr Ala Lys
                645                 650                 655
Gly Pro Asp Arg Ser Asp Phe Val Thr Asn Ala Ser Met Ser Asn Gln
            660                 665                 670
Ala Pro Gln Val Leu Asp Asn Gln Gly Asn Val Leu Thr Pro Thr Asn
        675                 680                 685
Gly Asn Thr Tyr Val Arg Pro Glu Gly Thr Tyr Val Val Thr Ala Asn
690                 695                 700
Gly Asp Asp Val Asn Val Thr Phe Thr Pro Asn Glu Asp Phe Ser Gly
705                 710                 715                 720
Val Ala Glu Gly Ile Asn Ile Arg Arg Thr Asp Ser Asn Gly Ser Ser
                725                 730                 735
Thr Gly Trp Gln Ser Thr Asp Ala Ala Asp Pro Asn Lys Asn Asp Arg
            740                 745                 750
Leu Asn Asn Met Asp Gly Arg Phe Val Pro Thr Val Arg Lys Val Pro
        755                 760                 765
Lys Tyr Asp Ser Thr Gly Ile Gln Gly Gln Asp Gly Gly Ser Gly Gly
770                 775                 780
Thr Ala His Ile Val Met Val Asp Ala Tyr Lys Pro Thr Lys
785                 790                 795
```

<210> SEQ ID NO 19
<211> LENGTH: 779
<212> TYPE: PRT
<213> ORGANISM: Streptococcus gordonii

<400> SEQUENCE: 19

```
Met Asp Glu Thr Ser Ala Ser Gly Val Gln Asn Glu Val Ala Arg Ala
1               5                   10                  15

Asp Leu Ala Glu Ser Pro Ala Thr Ala Pro Val Ala Ser Glu
            20                  25                  30

Ala Ser Gln Asn Ala Glu Thr Thr Val Ala Ala Thr Ala Thr Glu Ala
                35                  40                  45

Pro Gln Thr Ala Glu Asn Thr Ala Pro Thr Asn Ser Ala Ser Glu Ser
        50                  55                  60

Thr Glu Lys Pro Met Asp Glu Gln Pro Val Ala Ser Glu Thr Pro Gln
65                  70                  75                  80

Pro Ser Val Glu Lys Pro Val Leu Pro Thr Glu Val Lys Pro Ala Glu
                85                  90                  95

Asn Thr Thr Pro Ala Ser Thr Glu Ala Ser Pro Glu Thr Val Ser Pro
                100                 105                 110

Ser Arg Ala Thr Asp Gln Pro Val Ala Thr Arg Asp Ser Val Gln Ser
            115                 120                 125

Ser Arg Ser Arg Arg Leu Arg Arg Asp Leu Glu Ala Thr Ala Val Thr
130                 135                 140

Pro Gly Thr Gly Pro Ala Gly Ala Asp Asp Ala Thr Pro Ile Pro Arg
145                 150                 155                 160

Val Ser Lys Pro Thr Leu Ser Glu Ser Glu Lys Lys Glu Ser Thr Gln
                165                 170                 175

Leu Ala Lys Gln Ile Asn Trp Val Asp Phe Ser Asp Thr Ala Ser Met
            180                 185                 190

Lys Asn Leu Asp Pro Gln Gly Gly Phe Lys Val Gly Thr Val Phe Lys
            195                 200                 205

Lys Glu Ile Ser Pro Gly Tyr Val Val Thr Leu Thr Val Thr Glu Leu
            210                 215                 220

Lys Pro Phe Asn Ser Thr Glu Ile Tyr Lys Lys Arg Val Glu Gly Thr
225                 230                 235                 240

Pro Thr Ala Asn Thr Tyr Asp Pro Asn Ala Ile Asn Ser Tyr Leu Lys
                245                 250                 255

Gly Tyr Lys Asp Tyr Gly Lys Thr Pro Pro Ser Val Thr Gly Arg Pro
            260                 265                 270

Gln Asn Lys Phe Ser Thr Ile Gly Gly Gln Gly Phe Asp Thr Gln Gly
            275                 280                 285

Arg Lys Thr Gln Ile Ile Leu Pro Asp Asp Ala Val Asn Trp Gly Ile
290                 295                 300

Lys Phe Lys Val Glu Ala Thr Tyr Arg Gly Asn Pro Val Lys Pro Ser
305                 310                 315                 320

Val Val Met Ala Asp Gly Glu Asp Ala Asn Pro Ala Glu Tyr Gly Ile
                325                 330                 335

Phe Thr Thr Asn Gly Glu Gly Trp Glu Tyr Val Gly Glu Trp Met Lys
            340                 345                 350

Gly Pro Arg Ala Lys Gly Pro Tyr Thr Val Met Thr Glu Asp Met Val
            355                 360                 365

Lys Ala Phe Asp Lys Thr Arg Lys Asp Gly Leu Leu Ile Leu Lys Asp
370                 375                 380

Lys Ser Val Asp Trp Ser Lys Tyr Leu Ser Pro Asp Thr Val Thr Gly
385                 390                 395                 400

Gly Leu Gly Ser Gln Val Phe Gly Pro Ile Ile Ser Ala Ser Lys Ala
                405                 410                 415
```

-continued

Val Pro Val Val Met Thr Arg Gly Ala Ser Glu Val Gly Phe Tyr Val
        420                 425                 430

Ala Thr Gly Gly Gln Gln Ala Leu Met Met Gly Phe Leu Val Val Asp
    435                 440                 445

Ser Ser Asp Ala Pro Ala Ser Tyr Gly Glu Ala Tyr His Thr Ile Gly
450                 455                 460

Thr Arg Asp Ser Ile Ala Asn Thr Pro Ile Asn Gln Pro Tyr Leu Gly
465                 470                 475                 480

Ser Thr Ala Ala Asp Ile Asp Ala Asp Ser Glu Ser Asp Trp Thr Ala
            485                 490                 495

Asp Asp Arg Glu Asp Val Ala Asp Glu Gly Pro Ala Gln Leu Leu Thr
                500                 505                 510

Ala Asp Gln Leu Ser Lys Thr Asn Asp Leu Leu Asp Leu Asn Lys Ala
            515                 520                 525

Lys Asn Gly Thr Tyr Thr Leu Lys Ile Lys Ala Asn Pro Asn Gly Asn
530                 535                 540

Ala Lys Ala Tyr Val Lys Ala Trp Val Asp Phe Asn Asn Gly Lys
545                 550                 555                 560

Phe Asp Asp Asn Glu Gly Ser Val Val Lys Glu Ile Thr Ala Asn Gly
                565                 570                 575

Asp His Thr Leu Ser Phe Asn Ala Ile Pro Gly Leu Thr Gly Gly Leu
            580                 585                 590

Val Asp Gln Ile Gly Met Arg Val Arg Ile Ala Thr Asn Ala Gly Asp
        595                 600                 605

Ile Glu Lys Pro Thr Gly Thr Ala Phe Ser Gly Glu Val Glu Asp Met
610                 615                 620

Leu Val Arg Arg Val Tyr Pro Pro Gln Gly Glu Lys Gln Glu Ser Thr
625                 630                 635                 640

Gly Phe Gln Gly Glu Thr Gln Asn Ala Ser Val His Phe Thr Ala Lys
                645                 650                 655

Gly Pro Asp Arg Ser Asp Phe Val Thr Asn Ala Ser Met Ser Asn Gln
            660                 665                 670

Ala Pro Gln Val Leu Asp Asn Gln Gly Asn Val Leu Thr Pro Thr Asn
        675                 680                 685

Gly Asn Thr Tyr Val Arg Pro Glu Gly Thr Tyr Val Val Thr Ala Asn
    690                 695                 700

Gly Asp Asp Val Asn Val Thr Phe Thr Pro Asn Glu Asp Phe Ser Gly
705                 710                 715                 720

Val Ala Glu Gly Ile Asn Ile Arg Arg Thr Asp Ser Asn Gly Ser Ser
                725                 730                 735

Thr Gly Trp Gln Ser Thr Asp Ala Ala Asp Pro Asn Lys Asn Asp Arg
            740                 745                 750

Leu Asn Asn Met Asp Gly Arg Phe Val Pro Thr Val Arg Lys Val Pro
        755                 760                 765

Lys Tyr Asp Ser Thr Gly Ile Gln Gly Gln Asp
770                 775

<210> SEQ ID NO 20
<211> LENGTH: 2507
<212> TYPE: PRT
<213> ORGANISM: Streptococcus gordonii

<400> SEQUENCE: 20

```
Met Gly Lys Asp Leu Phe Asn Pro His Leu Arg Lys Phe Ser Ile Arg
1               5                   10                  15

Lys Leu Asn Val Gly Val Cys Ser Val Leu Leu Ser Thr Leu Ile Leu
            20                  25                  30

Leu Gly Ala Ala Thr Gln Val Ser Ala Asp Glu Thr Ser Ala Ser Gly
        35                  40                  45

Val Gln Asn Glu Val Ala Arg Ala Asp Leu Ala Glu Ser Pro Ala Thr
    50                  55                  60

Ala Thr Ala Pro Val Ala Ser Glu Ala Ser Gln Asn Ala Glu Thr Thr
65                  70                  75                  80

Val Ala Ala Thr Ala Thr Glu Ala Pro Gln Thr Ala Glu Asn Thr Ala
                85                  90                  95

Pro Thr Asn Ser Ala Ser Glu Ser Thr Glu Lys Pro Met Asp Glu Gln
            100                 105                 110

Pro Val Ala Ser Glu Thr Pro Gln Pro Ser Val Glu Lys Pro Val Leu
        115                 120                 125

Pro Thr Glu Val Lys Pro Ala Glu Asn Thr Thr Pro Ala Ser Thr Glu
130                 135                 140

Ala Ser Pro Glu Thr Val Ser Pro Ser Arg Ala Thr Asp Gln Pro Val
145                 150                 155                 160

Ala Thr Arg Asp Ser Val Gln Ser Arg Ser Arg Leu Arg Arg
                165                 170                 175

Asp Leu Glu Ala Thr Ala Val Thr Pro Gly Thr Gly Pro Ala Gly Ala
            180                 185                 190

Asp Asp Ala Thr Pro Ile Pro Arg Val Ser Lys Pro Thr Leu Ser Glu
        195                 200                 205

Ser Glu Lys Lys Glu Ser Thr Gln Leu Ala Lys Gln Ile Asn Trp Val
    210                 215                 220

Asp Phe Ser Asp Thr Ala Ser Met Lys Asn Leu Asp Pro Gln Gly Gly
225                 230                 235                 240

Phe Lys Val Gly Thr Val Phe Lys Lys Glu Ile Ser Pro Gly Tyr Val
                245                 250                 255

Val Thr Leu Thr Val Thr Glu Leu Lys Pro Phe Asn Ser Thr Glu Ile
            260                 265                 270

Tyr Lys Lys Arg Val Glu Gly Thr Pro Thr Ala Asn Thr Tyr Asp Pro
        275                 280                 285

Asn Ala Ile Asn Ser Tyr Leu Lys Gly Tyr Lys Asp Tyr Gly Lys Thr
    290                 295                 300

Pro Pro Ser Val Thr Gly Arg Pro Gln Asn Lys Phe Ser Thr Ile Gly
305                 310                 315                 320

Gly Gln Gly Phe Asp Thr Gln Gly Arg Lys Thr Gln Ile Ile Leu Pro
                325                 330                 335

Asp Asp Ala Val Asn Trp Gly Ile Lys Phe Lys Val Glu Ala Thr Tyr
            340                 345                 350

Arg Gly Asn Pro Val Lys Pro Ser Val Val Met Ala Asp Gly Glu Asp
        355                 360                 365

Ala Asn Pro Ala Glu Tyr Gly Ile Phe Thr Thr Asn Gly Glu Gly Trp
    370                 375                 380

Glu Tyr Val Gly Glu Trp Met Lys Gly Pro Arg Ala Lys Gly Pro Tyr
385                 390                 395                 400
```

-continued

Thr Val Met Thr Glu Asp Met Val Lys Ala Phe Asp Lys Thr Arg Lys
            405                 410                 415

Asp Gly Leu Leu Ile Leu Lys Asp Lys Ser Val Asp Trp Ser Lys Tyr
        420                 425                 430

Leu Ser Pro Asp Thr Val Thr Gly Gly Leu Gly Ser Gln Val Phe Gly
        435                 440                 445

Pro Ile Ile Ser Ala Ser Lys Ala Val Pro Val Met Thr Arg Gly
    450                 455                 460

Ala Ser Glu Val Gly Phe Tyr Val Ala Thr Gly Gln Gln Ala Leu
465                 470                 475                 480

Met Met Gly Phe Leu Val Val Asp Ser Ser Asp Ala Pro Ala Ser Tyr
                485                 490                 495

Gly Glu Ala Tyr His Thr Ile Gly Thr Arg Asp Ser Ile Ala Asn Thr
                500                 505                 510

Pro Ile Asn Gln Pro Tyr Leu Gly Ser Thr Ala Ala Asp Ile Asp Ala
                515                 520                 525

Asp Ser Glu Ser Asp Trp Thr Ala Asp Asp Arg Glu Asp Val Ala Asp
        530                 535                 540

Glu Gly Pro Ala Gln Leu Leu Thr Ala Asp Gln Leu Ser Lys Thr Asn
545                 550                 555                 560

Asp Leu Leu Asp Leu Asn Lys Ala Lys Asn Gly Thr Tyr Thr Leu Lys
                565                 570                 575

Ile Lys Ala Asn Pro Asn Gly Asn Ala Lys Ala Tyr Val Lys Ala Trp
                580                 585                 590

Val Asp Phe Asn Asn Gly Lys Phe Asp Asp Asn Glu Gly Ser Val
        595                 600                 605

Val Lys Glu Ile Thr Ala Asn Gly Asp His Thr Leu Ser Phe Asn Ala
        610                 615                 620

Ile Pro Gly Leu Thr Gly Gly Leu Val Asp Gln Ile Gly Met Arg Val
625                 630                 635                 640

Arg Ile Ala Thr Asn Ala Gly Asp Ile Glu Lys Pro Thr Gly Thr Ala
                645                 650                 655

Phe Ser Gly Glu Val Glu Asp Met Leu Val Arg Arg Val Tyr Pro Pro
                660                 665                 670

Gln Gly Glu Lys Gln Glu Ser Thr Gly Phe Gln Gly Glu Thr Gln Asn
            675                 680                 685

Ala Ser Val His Phe Thr Ala Lys Gly Pro Asp Arg Ser Asp Phe Val
        690                 695                 700

Thr Asn Ala Ser Met Ser Asn Gln Ala Pro Gln Val Leu Asp Asn Gln
705                 710                 715                 720

Gly Asn Val Leu Thr Pro Thr Asn Gly Asn Thr Tyr Val Arg Pro Glu
                725                 730                 735

Gly Thr Tyr Val Val Thr Ala Asn Gly Asp Asp Val Asn Val Thr Phe
                740                 745                 750

Thr Pro Asn Glu Asp Phe Ser Gly Val Ala Glu Gly Ile Asn Ile Arg
        755                 760                 765

Arg Thr Asp Ser Asn Gly Ser Ser Thr Gly Trp Gln Ser Thr Asp Ala
        770                 775                 780

Ala Asp Pro Asn Lys Asn Asp Arg Leu Asn Asn Met Asp Gly Arg Phe
785                 790                 795                 800

Val Pro Thr Val Arg Lys Val Pro Lys Tyr Asp Ser Thr Gly Ile Gln
                805                 810                 815

```
Gly Gln Asp Gln Ser Lys Glu Leu Val Phe Asn Asp Gly Asp Pro Ala
                820                 825                 830

Lys Thr Pro Val Thr Pro Asp Ala Ser Arg Pro Ala Thr Phe Val Asp
            835                 840                 845

Ala Asn Gly Gln Pro Val Thr Gly Asn Thr Val Pro Ala Met Ser Asn
850                 855                 860

Gly Gln Gln Val Gly Thr Tyr Glu Leu Asp Pro Asn Thr Gly Gln Val
865                 870                 875                 880

Thr Phe Lys Pro Asn Lys Thr Phe Val Gly Thr Pro Asp Pro Val Ala
                885                 890                 895

Val Gln Val Ser Asp Thr Asn Gly Val Pro His Arg Ala Arg Tyr Gln
            900                 905                 910

Pro Thr Val Thr Lys Val Thr Pro Thr Gly Thr Gly Ala Thr Ser Thr
            915                 920                 925

Gly Pro Gln Gly Val Pro Gln Thr Gly Thr Pro Thr Phe Gln Gly Gly
930                 935                 940

Asp Pro Leu Val Pro Ile Asp Glu Thr Val Glu Pro Thr Phe Glu Asp
945                 950                 955                 960

Gly Ser Lys Glu Lys Thr Ile Pro Gly Gln Gly Thr Tyr Thr Ile Ala
                965                 970                 975

Pro Asp Gly Thr Val Thr Phe Thr Pro Asp Lys Gln Phe Val Gly Asn
            980                 985                 990

Pro Asp Pro Val Thr Val Lys Arg Val Asp Lys Asn Gly Thr Pro Val
            995                 1000                1005

Thr Ala Thr Tyr Ser Pro Glu Phe Thr Lys Val Thr Pro Thr Ser
    1010                1015                1020

Thr Asp Ala Thr Ser Asn Gly Ile Gln Gly Gln Pro Gln Lys Gly
    1025                1030                1035

Thr Pro Thr Phe Thr Glu Gly Asn Pro Leu Val Pro Ile Asp Asp
    1040                1045                1050

Thr Lys Pro Met Thr Phe Glu Asp Gly Gln Ser Thr Lys Thr Val
    1055                1060                1065

Pro Gly Val Gly Glu Tyr Ser Ile Asn Pro Asp Gly Ser Ile Thr
    1070                1075                1080

Phe Thr Pro Asp Lys Lys Tyr Val Gly Thr Pro Asn Pro Val Thr
    1085                1090                1095

Val Lys Arg Val Asp Lys Asn Gly Thr Glu Val Thr Ala Thr Tyr
    1100                1105                1110

Thr Pro Thr Val Thr Lys Val Thr Pro Thr Ser Thr Asp Ala Thr
    1115                1120                1125

Ser Asn Gly Ile Gln Gly Gln Pro Gln Lys Gly Thr Pro Thr Phe
    1130                1135                1140

Thr Glu Gly Asn Pro Leu Val Pro Ile Asp Asp Thr Lys Pro Met
    1145                1150                1155

Thr Phe Glu Asp Gly Gln Ser Thr Lys Thr Val Pro Gly Val Gly
    1160                1165                1170

Glu Tyr Asn Ile Asn Pro Asp Gly Ser Ile Thr Phe Thr Pro Asp
    1175                1180                1185

Lys Gln Tyr Val Gly Thr Pro Asp Pro Val Thr Val Lys Arg Val
    1190                1195                1200

Asp Lys Asn Gly Thr Glu Val Thr Ala Thr Tyr Thr Pro Thr Val
    1205                1210                1215
```

-continued

```
Thr Lys Val Thr Pro Thr Ser Thr Asn Ala Thr Ser Thr Gly Pro
    1220                1225                1230

Gln Gly Val Pro Gln Thr Gly Thr Pro Thr Phe Gln Gly Gly Asp
    1235                1240                1245

Pro Leu Val Pro Ile Asp Glu Thr Val Glu Pro Thr Phe Glu Asp
    1250                1255                1260

Gly Ser Lys Glu Lys Val Ile Ser Gly Gln Gly Thr Tyr Thr Ile
    1265                1270                1275

Ala Pro Asp Gly Thr Val Thr Phe Thr Pro Asp Lys Arg Phe Val
    1280                1285                1290

Gly Lys Pro Asp Pro Val Thr Val Lys Arg Val Asp Lys Asn Gly
    1295                1300                1305

Thr Leu Ala Thr Ala Ile Tyr Ser Pro Glu Phe Thr Lys Val Thr
    1310                1315                1320

Pro Thr Gly Thr Gly Ala Thr Ser Thr Gly Pro Gln Gly Leu Pro
    1325                1330                1335

Gln Thr Gly Thr Pro Thr Phe Gln Gly Gly Asp Pro Leu Val Pro
    1340                1345                1350

Ile Asp Glu Thr Val Glu Pro Thr Phe Glu Asp Gly Ser Lys Glu
    1355                1360                1365

Lys Thr Ile Pro Gly Gln Gly Thr Tyr Thr Ile Ala Pro Asp Gly
    1370                1375                1380

Thr Val Thr Phe Thr Pro Asp Lys Gln Phe Val Gly Lys Pro Asp
    1385                1390                1395

Pro Val Thr Val Lys Arg Val Asp Lys Asn Gly Thr Pro Val Thr
    1400                1405                1410

Ala Thr Tyr Ser Pro Glu Phe Thr Lys Val Thr Pro Thr Gly Thr
    1415                1420                1425

Gly Asp Lys Thr Glu Gly Leu Gln Gly Gln Val Gln Glu Gly Lys
    1430                1435                1440

Val Asn Phe Thr Pro Gly His Asp Ser Val Pro Phe Pro Ala Asp
    1445                1450                1455

Ser Thr Pro Leu Phe Asp Asn Gly Thr Ala Val Lys Glu Val Pro
    1460                1465                1470

Asn Val Gly Lys Phe Glu Val Asp Ala Asp Gly Lys Val Thr Phe
    1475                1480                1485

Thr Pro Asp Lys Gln Phe Lys Gly Glu Thr Pro Glu Leu Glu Leu
    1490                1495                1500

Thr Arg Val Asp Ala Asn Gly Thr Pro Val Thr Val Lys Tyr Gln
    1505                1510                1515

Ala Val Val Lys Glu Val Thr Pro Thr Ser Thr Asp Ala Thr Ser
    1520                1525                1530

Asn Gly Ile Gln Gly Gln Pro Gln Lys Gly Thr Pro Ile Phe Thr
    1535                1540                1545

Glu Gly Asn Pro Leu Val Pro Ile Asp Asp Thr Lys Pro Met Thr
    1550                1555                1560

Phe Glu Asp Gly Gln Ser Thr Lys Thr Val Pro Gly Val Gly Glu
    1565                1570                1575

Tyr Ser Ile Asn Pro Asp Gly Ser Ile Thr Phe Thr Pro Asp Lys
    1580                1585                1590

Gln Tyr Val Gly Thr Pro Asp Pro Val Thr Val Lys Arg Val Asp
    1595                1600                1605
```

| | | | | | | | | | | |
|---|---|---|---|---|---|---|---|---|---|---|
| Lys | Asn | Gly | Thr | Glu | Val | Thr | Ala | Thr | Tyr | Thr | Pro | Thr | Val | Thr |
| | | 1610 | | | | 1615 | | | | 1620 | | | | |
| Lys | Val | Thr | Pro | Thr | Ser | Thr | Asn | Ala | Thr | Ser | Thr | Gly | Pro | Gln |
| | 1625 | | | | | 1630 | | | | | 1635 | | | |
| Gly | Val | Pro | Gln | Thr | Gly | Thr | Pro | Thr | Phe | Gln | Gly | Gly | Asp | Pro |
| | 1640 | | | | | 1645 | | | | | 1650 | | | |
| Leu | Val | Pro | Ile | Asp | Glu | Thr | Val | Glu | Pro | Thr | Phe | Asp | Asp | Gly |
| | 1655 | | | | | 1660 | | | | | 1665 | | | |
| Ser | Lys | Glu | Lys | Asn | Ile | Pro | Gly | Gln | Gly | Thr | Tyr | Thr | Ile | Ala |
| | 1670 | | | | | 1675 | | | | | 1680 | | | |
| Pro | Asp | Gly | Thr | Val | Thr | Phe | Thr | Pro | Asp | Lys | Gln | Phe | Val | Gly |
| | 1685 | | | | | 1690 | | | | | 1695 | | | |
| Lys | Pro | Asp | Pro | Val | Thr | Val | Lys | Arg | Val | Asp | Lys | Asn | Gly | Thr |
| | 1700 | | | | | 1705 | | | | | 1710 | | | |
| Glu | Val | Thr | Ser | Ile | Tyr | Thr | Pro | Thr | Val | Thr | Lys | Val | Thr | Pro |
| | 1715 | | | | | 1720 | | | | | 1725 | | | |
| Thr | Gly | Thr | Gly | Ala | Thr | Ser | Thr | Gly | Pro | Gln | Gly | Leu | Ser | Gln |
| | 1730 | | | | | 1735 | | | | | 1740 | | | |
| Thr | Gly | Ile | Pro | Ser | Phe | Gln | Gly | Gly | Asp | Pro | Leu | Val | Pro | Ile |
| | 1745 | | | | | 1750 | | | | | 1755 | | | |
| Asp | Glu | Thr | Val | Glu | Pro | Thr | Phe | Glu | Asp | Gly | Ser | Lys | Glu | Lys |
| | 1760 | | | | | 1765 | | | | | 1770 | | | |
| Ser | Ile | Pro | Gly | Gln | Gly | Thr | Tyr | Thr | Ile | Ala | Pro | Asp | Gly | Thr |
| | 1775 | | | | | 1780 | | | | | 1785 | | | |
| Val | Thr | Phe | Thr | Pro | Asp | Lys | Gln | Phe | Val | Gly | Lys | Pro | Asp | Pro |
| | 1790 | | | | | 1795 | | | | | 1800 | | | |
| Val | Thr | Val | Lys | Arg | Val | Asp | Lys | Asn | Gly | Thr | Pro | Val | Thr | Ala |
| | 1805 | | | | | 1810 | | | | | 1815 | | | |
| Thr | Tyr | Ser | Pro | Glu | Phe | Thr | Lys | Val | Thr | Pro | Thr | Gly | Thr | Gly |
| | 1820 | | | | | 1825 | | | | | 1830 | | | |
| Ala | Thr | Ser | Thr | Gly | Pro | Gln | Gly | Leu | Pro | Gln | Thr | Gly | Thr | Pro |
| | 1835 | | | | | 1840 | | | | | 1845 | | | |
| Thr | Phe | Gln | Gly | Gly | Asp | Pro | Leu | Val | Pro | Ile | Asp | Glu | Thr | Val |
| | 1850 | | | | | 1855 | | | | | 1860 | | | |
| Glu | Pro | Thr | Phe | Glu | Asp | Gly | Ser | Lys | Glu | Lys | Thr | Ile | Pro | Gly |
| | 1865 | | | | | 1870 | | | | | 1875 | | | |
| Gln | Gly | Thr | Tyr | Thr | Ile | Ala | Pro | Asp | Gly | Thr | Val | Thr | Phe | Thr |
| | 1880 | | | | | 1885 | | | | | 1890 | | | |
| Pro | Asp | Lys | Gln | Phe | Val | Gly | Lys | Pro | Asp | Pro | Val | Thr | Val | Lys |
| | 1895 | | | | | 1900 | | | | | 1905 | | | |
| Arg | Val | Asp | Lys | Asn | Gly | Thr | Pro | Val | Thr | Ala | Thr | Tyr | Ser | Pro |
| | 1910 | | | | | 1915 | | | | | 1920 | | | |
| Glu | Phe | Thr | Lys | Val | Thr | Pro | Thr | Gly | Thr | Gly | Ala | Thr | Ser | Thr |
| | 1925 | | | | | 1930 | | | | | 1935 | | | |
| Gly | Pro | Gln | Gly | Leu | Pro | Gln | Thr | Gly | Thr | Pro | Thr | Phe | Lys | Gly |
| | 1940 | | | | | 1945 | | | | | 1950 | | | |
| Gly | Asp | Pro | Leu | Val | Pro | Ile | Asp | Glu | Ala | Val | Glu | Pro | Thr | Phe |
| | 1955 | | | | | 1960 | | | | | 1965 | | | |
| Glu | Asp | Gly | Ser | Lys | Glu | Lys | Ser | Ile | Pro | Gly | Gln | Gly | Thr | Tyr |
| | 1970 | | | | | 1975 | | | | | 1980 | | | |
| Thr | Ile | Ala | Pro | Asp | Gly | Thr | Val | Thr | Phe | Thr | Pro | Asp | Lys | Gln |
| | 1985 | | | | | 1990 | | | | | 1995 | | | |

```
Phe Val Gly Lys Pro Asp Pro Val Thr Val Lys Arg Val Asp Lys
2000                2005                2010

Asn Gly Thr Pro Val Thr Ala Thr Tyr Arg Pro Glu Phe Thr Lys
2015                2020                2025

Val Thr Pro Thr Gly Thr Gly Ala Thr Ser Thr Gly Pro Gln Gly
2030                2035                2040

Leu Pro Gln Thr Gly Thr Pro Thr Phe Gln Gly Gly Asp Pro Leu
2045                2050                2055

Val Pro Ile Asp Glu Thr Val Glu Pro Thr Phe Glu Asp Gly Ser
2060                2065                2070

Lys Glu Lys Thr Ile Pro Gly Gln Gly Thr Tyr Thr Ile Val Pro
2075                2080                2085

Asp Gly Thr Val Thr Phe Thr Pro Asp Lys Gln Phe Val Gly Lys
2090                2095                2100

Pro Asp Pro Val Thr Val Lys Arg Val Asp Lys Asn Gly Thr Pro
2105                2110                2115

Val Thr Ala Thr Tyr Ser Pro Glu Phe Thr Lys Val Thr Pro Ile
2120                2125                2130

Gly Lys Asp Ala Ser Ser Glu Asn Ile Lys Gly Leu Val Gln Thr
2135                2140                2145

Gly Thr Pro Thr Phe Glu Gly Gly Asp Pro Leu Val Pro Ile Asp
2150                2155                2160

Glu Thr Val Ala Pro Thr Phe Glu Asp Gly Ser Thr Glu Lys Val
2165                2170                2175

Ile Pro Gly Glu Gly Ile Tyr Thr Ile Ser Pro Asp Gly Thr Val
2180                2185                2190

Thr Phe Thr Pro Glu Ala Asp Phe Val Gly Lys Gly Thr Gly Val
2195                2200                2205

Thr Ile Val Arg Lys Asp Lys Asn Gly Thr Pro Val Thr Ala Ser
2210                2215                2220

Tyr Arg Pro Thr Val Val Asp Pro Ser Thr Gly Gln Asp Thr Thr
2225                2230                2235

Ser Thr Gly Ala Lys Gly Gln Thr Gln Val Ala Thr Pro Ala Phe
2240                2245                2250

Glu Gly His Ile Asp Ser Thr Val Pro Pro Thr Phe Glu Asp Gly
2255                2260                2265

Ser Thr Thr Leu Val Val Pro Gly Glu Gly Ser Tyr Thr Ile Asp
2270                2275                2280

Lys Asp Gly His Ile Thr Phe Thr Pro Glu Ala Asp Phe Val Gly
2285                2290                2295

Thr Ala Lys Gly Val Val Val Lys Arg Leu Asp Ile Tyr Gly Asn
2300                2305                2310

Val Val Thr Ala Gln Tyr Thr Pro Thr Val Ile Gly Gln Thr Arg
2315                2320                2325

Val Glu Asp Ile Thr Ser Asp Gly Leu Lys Gly Gln Thr Gln Thr
2330                2335                2340

Gly Lys Pro Ile Phe Glu Gly Asp Val Asp Leu Thr Val Ala Pro
2345                2350                2355

Thr Phe Glu Asp Gly Ser Thr Glu Lys Val Val Pro Gly Glu Gly
2360                2365                2370

Thr Tyr Thr Ile Ser Pro Asp Gly Val Val Thr Phe Ile Pro Glu
2375                2380                2385
```

```
Pro Asn Phe Val Gly Thr Ala Lys Gly Val Val Val Ile Arg Lys
    2390                2395                2400

Asp Arg Asn Gly Gln Thr Ile Ser Ala Ser Tyr Thr Pro Arg Val
    2405                2410                2415

Thr Glu Ile Pro Val Val Pro Asn Arg Pro Ser Thr Pro Glu Gln
    2420                2425                2430

Pro Lys Ala Pro Val Ile Pro Val Asp Pro Thr Val Val Val Gln
    2435                2440                2445

Thr Pro Lys Ala Glu Glu Arg Val Glu Pro Ile Tyr Ile Asp Pro
    2450                2455                2460

Lys Asp Glu Lys Gly Val Leu Pro Arg Thr Gly Ser Gln Thr Ser
    2465                2470                2475

Asp Gln Thr Ala Ser Gly Leu Leu Ala Ala Ile Ala Ser Leu Thr
    2480                2485                2490

Phe Phe Gly Leu Ala Asn Arg Lys Lys Ser Lys Glu Asp
    2495                2500                2505

<210> SEQ ID NO 21
<211> LENGTH: 22
<212> TYPE: PRT
<213> ORGANISM: Homo sapiens

<400> SEQUENCE: 21

Lys Arg Arg Pro Lys Gly Arg Gly Lys Arg Arg Glu Lys Gln Arg
1               5                   10                  15

Pro Thr Asp Cys His Leu
                20

<210> SEQ ID NO 22
<211> LENGTH: 150
<212> TYPE: PRT
<213> ORGANISM: Homo sapiens

<400> SEQUENCE: 22

Leu Pro Ala Val Pro Pro Gln Gln Trp Ala Leu Ser Ala Gly Asn
1               5                   10                  15

Ser Ser Glu Val Glu Val Val Pro Phe Gln Glu Val Trp Gly Arg Ser
                20                  25                  30

Tyr Cys Arg Ala Leu Glu Arg Leu Val Asp Val Val Ser Glu Tyr Pro
                35                  40                  45

Ser Glu Val Glu His Met Phe Ser Pro Ser Cys Val Ser Leu Leu Arg
                50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
                100                 105                 110

Arg Pro Leu Arg Glu Lys Met Lys Pro Glu Arg Arg Arg Pro Lys Gly
                115                 120                 125

Arg Gly Lys Arg Arg Arg Glu Lys Gln Arg Pro Thr Asp Cys Cys Gly
                130                 135                 140

Asp Ala Val Pro Arg Arg
145                 150

<210> SEQ ID NO 23
<211> LENGTH: 116
```

```
<212> TYPE: PRT
<213> ORGANISM: Artificial Sequence
<220> FEATURE:
<223> OTHER INFORMATION: Recombinant sequence

<400> SEQUENCE: 23

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile
        115

<210> SEQ ID NO 24
<211> LENGTH: 13
<212> TYPE: PRT
<213> ORGANISM: Artificial Sequence
<220> FEATURE:
<223> OTHER INFORMATION: Recombinant sequence

<400> SEQUENCE: 24

Ala His Ile Val Met Val Asp Ala Tyr Lys Pro Thr Lys
1               5                   10

<210> SEQ ID NO 25
<211> LENGTH: 625
<212> TYPE: PRT
<213> ORGANISM: Bos taurus

<400> SEQUENCE: 25

Met Ala Arg Val Arg Gly Pro Arg Leu Pro Gly Cys Leu Ala Leu Ala
1               5                   10                  15

Ala Leu Phe Ser Leu Val His Ser Gln His Val Phe Leu Ala His Gln
            20                  25                  30

Gln Ala Ser Ser Leu Leu Gln Arg Ala Arg Arg Ala Asn Lys Gly Phe
        35                  40                  45

Leu Glu Glu Val Arg Lys Gly Asn Leu Glu Arg Glu Cys Leu Glu Glu
    50                  55                  60

Pro Cys Ser Arg Glu Glu Ala Phe Glu Ala Leu Glu Ser Leu Ser Ala
65                  70                  75                  80

Thr Asp Ala Phe Trp Ala Lys Tyr Thr Ala Cys Glu Ser Ala Arg Asn
                85                  90                  95

Pro Arg Glu Lys Leu Asn Glu Cys Leu Glu Gly Asn Cys Ala Glu Gly
            100                 105                 110

Val Gly Met Asn Tyr Arg Gly Asn Val Ser Val Thr Arg Ser Gly Ile
        115                 120                 125

Glu Cys Gln Leu Trp Arg Ser Arg Tyr Pro His Lys Pro Glu Ile Asn
    130                 135                 140
```

```
Ser Thr Thr His Pro Gly Ala Asp Leu Arg Glu Asn Phe Cys Arg Asn
145                 150                 155                 160

Pro Asp Gly Ser Ile Thr Gly Pro Trp Cys Tyr Thr Ser Pro Thr
            165                 170                 175

Leu Arg Arg Glu Glu Cys Ser Val Pro Val Cys Gly Gln Asp Arg Val
            180                 185                 190

Thr Val Glu Val Ile Pro Arg Ser Gly Ser Thr Thr Ser Gln Ser
        195                 200                 205

Pro Leu Leu Glu Thr Cys Val Pro Asp Arg Gly Arg Glu Tyr Arg Gly
    210                 215                 220

Arg Leu Ala Val Thr Thr Ser Gly Ser Arg Cys Leu Ala Trp Ser Ser
225                 230                 235                 240

Glu Gln Ala Lys Ala Leu Ser Lys Asp Gln Asp Phe Asn Pro Ala Val
                245                 250                 255

Pro Leu Ala Glu Asn Phe Cys Arg Asn Pro Asp Gly Asp Glu Glu Gly
            260                 265                 270

Ala Trp Cys Tyr Val Ala Asp Gln Pro Gly Asp Phe Glu Tyr Cys Asp
        275                 280                 285

Leu Asn Tyr Cys Glu Glu Pro Val Asp Gly Asp Leu Gly Asp Arg Leu
    290                 295                 300

Gly Glu Asp Pro Asp Pro Asp Ala Ala Ile Glu Gly Arg Thr Ser Glu
305                 310                 315                 320

Asp His Phe Gln Pro Phe Phe Asn Glu Lys Thr Phe Gly Ala Gly Glu
                325                 330                 335

Ala Asp Cys Gly Leu Arg Pro Leu Phe Glu Lys Lys Gln Val Gln Asp
            340                 345                 350

Gln Thr Glu Lys Glu Leu Phe Glu Ser Tyr Ile Glu Gly Arg Ile Val
        355                 360                 365

Glu Gly Gln Asp Ala Glu Val Gly Leu Ser Pro Trp Gln Val Met Leu
370                 375                 380

Phe Arg Lys Ser Pro Gln Glu Leu Leu Cys Gly Ala Ser Leu Ile Ser
385                 390                 395                 400

Asp Arg Trp Val Leu Thr Ala Ala His Cys Leu Leu Tyr Pro Pro Trp
                405                 410                 415

Asp Lys Asn Phe Thr Val Asp Asp Leu Leu Val Arg Ile Gly Lys His
            420                 425                 430

Ser Arg Thr Arg Tyr Glu Arg Lys Val Glu Lys Ile Ser Met Leu Asp
        435                 440                 445

Lys Ile Tyr Ile His Pro Arg Tyr Asn Trp Lys Glu Asn Leu Asp Arg
450                 455                 460

Asp Ile Ala Leu Leu Lys Leu Lys Arg Pro Ile Glu Leu Ser Asp Tyr
465                 470                 475                 480

Ile His Pro Val Cys Leu Pro Asp Lys Gln Thr Ala Ala Lys Leu Leu
                485                 490                 495

His Ala Gly Phe Lys Gly Arg Val Thr Gly Trp Gly Asn Arg Arg Glu
            500                 505                 510

Thr Trp Thr Thr Ser Val Ala Glu Val Gln Pro Ser Val Leu Gln Val
        515                 520                 525

Val Asn Leu Pro Leu Val Glu Arg Pro Val Cys Lys Ala Ser Thr Arg
530                 535                 540

Ile Arg Ile Thr Asp Asn Met Phe Cys Ala Gly Tyr Lys Pro Gly Glu
545                 550                 555                 560
```

-continued

Gly Lys Arg Gly Asp Ala Cys Glu Gly Asp Ser Gly Pro Phe Val
              565                 570                 575

Met Lys Ser Pro Tyr Asn Asn Arg Trp Tyr Gln Met Gly Ile Val Ser
              580                 585                 590

Trp Gly Glu Gly Cys Asp Arg Asp Gly Lys Tyr Gly Phe Tyr Thr His
          595                 600                 605

Val Phe Arg Leu Lys Lys Trp Ile Gln Lys Val Ile Asp Arg Leu Gly
    610                 615                 620

Ser
625

<210> SEQ ID NO 26
<211> LENGTH: 622
<212> TYPE: PRT
<213> ORGANISM: Homo sapiens

<400> SEQUENCE: 26

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Ala Asn Thr Phe Leu
            35                  40                  45

Glu Glu Val Arg Lys Gly Asn Leu Glu Arg Glu Cys Val Glu Glu Thr
        50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

```
Asn Tyr Cys Glu Glu Ala Val Glu Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
610                 615                 620

<210> SEQ ID NO 27
<211> LENGTH: 863
<212> TYPE: PRT
<213> ORGANISM: Streptococcus gordonii

<400> SEQUENCE: 27

Met Gly Lys Asp Leu Phe Asn Thr His Leu Ser Lys Phe Ser Ile Arg
1               5                   10                  15

Lys Leu Asn Ile Gly Val Cys Ser Val Leu Leu Ser Thr Leu Ile Leu
            20                  25                  30
```

```
Leu Gly Thr Ala Leu Gln Val Ser Ala Glu Thr Ser Ser Gly
        35                  40                  45
Phe Gln Asn Glu Ile Ser Lys Ala Asp Val Thr Glu Ser Pro Val Ile
 50                  55                  60
Ser Asp Glu Ser Thr Thr Tyr Gln Gln Val Gln Asn Thr Glu Lys Thr
 65                  70                  75                  80
Glu Ser Val Pro Asp Ser Glu Lys Ser Gln Ser Ala Asp Asn Pro Ile
                 85                  90                  95
Gln Arg Asn Ser Gly Leu Glu Gly Val Glu Lys Thr Thr Asp Ser Ile
                100                 105                 110
Gln Ala Lys Ser Thr Asp Asp Ile Lys Ser Thr Val Val Gln Gln Gly
                115                 120                 125
Ser Thr Glu Ser Gln Val Val Asp Glu Asn Ser Gly Val Lys Thr Asp
        130                 135                 140
Val Thr Gln Ala Ser Arg Ser Arg Arg Val Arg Arg Asp Ala Thr Pro
145                 150                 155                 160
Thr Gly Gln Gln Asn Gly Val Thr Thr Gly Val Pro Ile Gly Thr Gly
                165                 170                 175
Pro Ala Gly Ala Asp Asp Ala Thr Ser Lys Pro Arg Val Pro Lys Pro
                180                 185                 190
Ser Leu Asp Glu Ser Leu Lys Lys Asp Ser Val Gln Leu Ala Lys Gln
                195                 200                 205
Ile Ser Trp Leu Asp Phe Ser Asp Ser Ala Ser Trp Lys Asn Leu Asp
        210                 215                 220
Gln Arg Gly Gly Leu Lys Val Gly Thr Thr Phe Thr Lys Glu Ile Ser
225                 230                 235                 240
Pro Gly Tyr Val Val Thr Leu Thr Val Lys Glu Leu Lys Pro Phe Asn
                245                 250                 255
Ser Thr Glu Ile Tyr Lys Lys Arg Val Ala Gly Thr Ala Thr Glu Gly
                260                 265                 270
Thr Tyr Asn Pro Asp Ala Glu Asn Gly Phe Leu Thr Ser Ala Pro Tyr
        275                 280                 285
Tyr Gly Lys Thr Pro Pro Ser Val Thr Gly Ala Ala Gln Asn Glu
        290                 295                 300
Trp Thr Thr Ile Arg Asp Gln Gly Phe Asn Thr Gln Lys Arg Lys Thr
305                 310                 315                 320
Gln Leu Val Tyr Pro Met Asn Ser Thr Asn Trp Gly Val Lys Phe Asp
                325                 330                 335
Ile Glu Ala Thr Tyr Leu Gly Lys Arg Val Ala Pro Thr Val Val Met
                340                 345                 350
Ala Asp Gly Glu Asp Ala Asn Pro Gly Glu Phe Ala Ile Phe Thr Thr
        355                 360                 365
Asn Gly Thr Gly Trp Glu Tyr Met Gly Glu Trp Lys Met Lys Ser Pro
        370                 375                 380
Ala Lys Glu Ala Tyr Thr Val Ile Thr Lys Lys Met Leu Asp Asp Glu
385                 390                 395                 400
Asp Val Lys Arg Arg Gly Leu Leu Ile Leu Lys Asp Lys Ser Val Asp
                405                 410                 415
Trp Tyr Lys Tyr Leu Ser Pro Asp Thr Val Thr Gly Leu Gly Ser
                420                 425                 430
Gln Val Phe Gly Pro Asn Arg Ser Asn Glu Arg Thr Val Pro Val Val
        435                 440                 445
```

```
Met Thr Arg Gly Ala Ser Glu Val Gly Phe Tyr Val Ala Ser Ser Gly
    450                 455                 460
Gln Gln Ala Met Met Met Gly Phe Leu Val Val Asp Val Ser Asp Ala
465             470                 475                 480
Pro Glu Ser Tyr Gly Glu Ala Phe His Thr Ile Ser Thr Arg Asp Ser
                485                 490                 495
Val Thr Asn Asp Leu Pro Gln Pro Tyr Leu Gly Thr Thr Pro Ala Asp
            500                 505                 510
Ile Asp Val Glu Ser Ser Asn Asp Trp Val Leu Asp Lys Lys Glu
        515                 520                 525
His Lys Asp Glu Gly Ala Ser Gln Leu Leu Ala Asp Gln Leu Ser
530                 535                 540
Thr Ser Asn Asp Leu Leu Asp Leu Asp Lys Ala Lys Asn Gly Thr Tyr
545                 550                 555                 560
Thr Ile Lys Ile Lys Ala Asn Pro Asn Gly Asn Ala Lys Ser Tyr Val
                565                 570                 575
Lys Ala Trp Ile Asp Phe Asn Asn Asp Gly Val Phe Asn Glu Ser Glu
            580                 585                 590
Gly Ser Asn Leu Gln Glu Ile Thr Ala Ala Gly Asp Tyr Thr Leu Thr
        595                 600                 605
Phe Asn Ala Asn Pro Asn Ile Ser Gly Gly Gln Val Asp Lys Leu Gly
610                 615                 620
Met Arg Phe Arg Ile Ala Thr Asn Lys Gly Asp Ile Glu Gln Pro Thr
625                 630                 635                 640
Gly Ile Ala Phe Ser Gly Glu Val Glu Asp Met Leu Leu His Arg Ile
                645                 650                 655
Tyr Pro Pro Lys Gly Glu Lys Gln Thr Thr Asp Gly Phe Thr Gly Glu
            660                 665                 670
Thr Gln Thr Ala Val Leu His Phe Thr Pro Lys Gly Thr Asp Arg Ser
        675                 680                 685
Asp Asp Ser Val Asn Ala Val Met Ser Thr Gln Ala Pro Gln Ile Leu
690                 695                 700
Asp Lys Gln Gly Gln Val Leu Thr Ala Val Asp Gly Asn Tyr Ile Arg
705                 710                 715                 720
Pro Glu Gly Thr Tyr Gln Val Thr Val Asn Gly Asn Asp Val Gln Val
                725                 730                 735
Thr Phe Thr Pro Lys Ala Asp Phe Ser Gly Thr Ala Asp Gly Ile Asn
            740                 745                 750
Ile Arg Trp Thr Asp Gln Asn Gly Thr Ser Thr Gly Trp Ala Ser Thr
        755                 760                 765
Asp Ala Ser Asp Pro Asn Met Asn Asp Leu Leu Asn Thr Met Asp Gly
770                 775                 780
Ser Tyr Met Pro Thr Val Arg Lys Ile Pro Asn Tyr Glu Ser Ser Gly
785                 790                 795                 800
Leu Gln Gly Leu Glu Gln Asn Lys Thr Leu Val Phe Asn Asp Asp
                805                 810                 815
Ala Asn Thr Pro Pro Val Thr Pro Asp Thr Thr Arg Pro Ala Ser Phe
            820                 825                 830
Val Asp Ala Ser Gly Gln Pro Val Ala Gly Asn Thr Val Pro Ala Met
        835                 840                 845
Ser Asn Gly Gln Gln Val Gly Thr Tyr Glu Leu Asp Pro Asn Thr
850                 855                 860
```

-continued

```
<210> SEQ ID NO 28
<211> LENGTH: 863
<212> TYPE: PRT
<213> ORGANISM: Streptococcus gordonii

<400> SEQUENCE: 28
```

| | | | | | | | | | | | | | | | |
|---|---|---|---|---|---|---|---|---|---|---|---|---|---|---|---|
| Met | Gly | Lys | Asp | Leu | Phe | Asn | Thr | His | Leu | Ser | Lys | Phe | Ser | Ile | Arg |
| 1 | | | | 5 | | | | | 10 | | | | | 15 | |
| Lys | Leu | Asn | Ile | Gly | Val | Cys | Ser | Val | Leu | Leu | Ser | Thr | Leu | Ile | Leu |
| | | | 20 | | | | 25 | | | | | 30 | | | |
| Leu | Gly | Thr | Ala | Leu | Gln | Val | Ser | Ala | Glu | Glu | Thr | Ser | Thr | Ser | Gly |
| | | 35 | | | | | 40 | | | | | 45 | | | |
| Phe | Gln | Asn | Glu | Ile | Ser | Lys | Ala | Asp | Val | Thr | Glu | Ser | Pro | Val | Ile |
| 50 | | | | | 55 | | | | | 60 | | | | | |
| Ser | Asp | Glu | Ser | Thr | Thr | Tyr | Gln | Gln | Val | Gln | Asn | Thr | Glu | Lys | Thr |
| 65 | | | | | 70 | | | | | 75 | | | | | 80 |
| Glu | Ser | Val | Pro | Asp | Ser | Glu | Lys | Ser | Gln | Ser | Ala | Asp | Asn | Pro | Ile |
| | | | | 85 | | | | | 90 | | | | | 95 | |
| Gln | Arg | Asn | Ser | Gly | Leu | Glu | Gly | Val | Glu | Lys | Thr | Thr | Asp | Ser | Ile |
| | | | 100 | | | | | 105 | | | | | 110 | | |
| Gln | Ala | Lys | Ser | Thr | Asp | Asp | Ile | Lys | Ser | Thr | Val | Val | Gln | Gln | Gly |
| | | | 115 | | | | | 120 | | | | | 125 | | |
| Ser | Thr | Glu | Ser | Gln | Val | Val | Asp | Glu | Asn | Ser | Gly | Val | Lys | Thr | Asp |
| | 130 | | | | | 135 | | | | | 140 | | | | |
| Val | Thr | Gln | Ala | Ser | Arg | Ser | Arg | Arg | Val | Arg | Arg | Asp | Ala | Thr | Pro |
| 145 | | | | | 150 | | | | | 155 | | | | | 160 |
| Thr | Gly | Gln | Gln | Asn | Gly | Val | Thr | Thr | Gly | Val | Pro | Ile | Gly | Thr | Gly |
| | | | | 165 | | | | | 170 | | | | | 175 | |
| Pro | Ala | Gly | Ala | Asp | Asp | Ala | Thr | Ser | Lys | Pro | Arg | Val | Pro | Lys | Pro |
| | | | 180 | | | | | 185 | | | | | 190 | | |
| Ser | Leu | Asp | Glu | Ser | Leu | Lys | Lys | Asp | Ser | Val | Gln | Leu | Ala | Lys | Gln |
| | | | 195 | | | | | 200 | | | | | 205 | | |
| Ile | Ser | Trp | Leu | Asp | Phe | Ser | Asp | Ser | Ala | Ser | Trp | Lys | Asn | Leu | Asp |
| | 210 | | | | | 215 | | | | | 220 | | | | |
| Gln | Arg | Gly | Gly | Leu | Lys | Val | Gly | Thr | Thr | Phe | Thr | Lys | Glu | Ile | Ser |
| 225 | | | | | 230 | | | | | 235 | | | | | 240 |
| Pro | Gly | Tyr | Val | Val | Thr | Leu | Thr | Val | Lys | Glu | Leu | Lys | Pro | Phe | Asn |
| | | | | 245 | | | | | 250 | | | | | 255 | |
| Ser | Thr | Glu | Ile | Tyr | Lys | Lys | Arg | Val | Ala | Gly | Thr | Ala | Thr | Glu | Gly |
| | | | 260 | | | | | 265 | | | | | 270 | | |
| Thr | Tyr | Asn | Pro | Asp | Ala | Glu | Asn | Gly | Phe | Leu | Thr | Ser | Ala | Pro | Tyr |
| | | 275 | | | | | 280 | | | | | 285 | | | |
| Tyr | Gly | Lys | Thr | Pro | Pro | Ser | Val | Thr | Gly | Ala | Ala | Gln | Asn | Glu |
| | 290 | | | | | 295 | | | | | 300 | | | | |
| Trp | Thr | Thr | Ile | Arg | Asp | Gln | Gly | Phe | Asn | Thr | Gln | Lys | Arg | Lys | Thr |
| 305 | | | | | 310 | | | | | 315 | | | | | 320 |
| Gln | Leu | Val | Tyr | Pro | Met | Asn | Ser | Thr | Asn | Trp | Gly | Val | Lys | Phe | Asp |
| | | | | 325 | | | | | 330 | | | | | 335 | |
| Ile | Glu | Ala | Thr | Tyr | Leu | Gly | Lys | Arg | Val | Ala | Pro | Thr | Val | Val | Met |
| | | | 340 | | | | | 345 | | | | | 350 | | |
| Ala | Asp | Gly | Glu | Asp | Ala | Asn | Pro | Gly | Glu | Phe | Ala | Ile | Phe | Thr | Thr |
| | | 355 | | | | | 360 | | | | | 365 | | | |
| Asn | Gly | Thr | Gly | Trp | Glu | Tyr | Met | Gly | Glu | Trp | Lys | Met | Lys | Ser | Pro |
| | 370 | | | | | 375 | | | | | 380 | | | | |

-continued

```
Ala Lys Glu Ala Tyr Thr Val Ile Thr Lys Lys Met Leu Asp Asp Glu
385                 390                 395                 400

Asp Val Lys Arg Arg Gly Leu Leu Ile Leu Lys Asp Lys Ser Val Asp
            405                 410                 415

Trp Tyr Lys Tyr Leu Ser Pro Asp Thr Val Thr Gly Gly Leu Gly Ser
        420                 425                 430

Gln Val Phe Gly Pro Asn Arg Ser Asn Glu Arg Thr Val Pro Val Val
    435                 440                 445

Met Thr Arg Gly Ala Ser Glu Val Gly Phe Tyr Val Ala Ser Ser Gly
450                 455                 460

Gln Gln Ala Met Met Met Gly Phe Leu Val Val Asp Val Ser Asp Ala
465                 470                 475                 480

Pro Glu Ser Tyr Gly Glu Ala Phe His Thr Ile Ser Thr Arg Asp Ser
                485                 490                 495

Val Thr Asn Asp Leu Pro Gln Pro Tyr Leu Gly Thr Thr Pro Ala Asp
            500                 505                 510

Ile Asp Val Glu Ser Ser Asn Asp Trp Val Leu Asp Asp Lys Lys Glu
        515                 520                 525

His Lys Asp Glu Gly Ala Ser Gln Leu Leu Ala Asp Asp Gln Leu Ser
    530                 535                 540

Thr Ser Asn Asp Leu Leu Asp Leu Asp Lys Ala Lys Asn Gly Thr Tyr
545                 550                 555                 560

Thr Ile Lys Ile Lys Ala Asn Pro Asn Gly Asn Ala Lys Ser Tyr Val
                565                 570                 575

Lys Ala Trp Ile Asp Phe Asn Asn Asp Gly Val Phe Asn Glu Ser Glu
            580                 585                 590

Gly Ser Asn Leu Gln Glu Ile Thr Ala Ala Gly Asp Tyr Thr Leu Thr
        595                 600                 605

Phe Asn Ala Asn Pro Asn Ile Ser Gly Gly Gln Val Asp Lys Leu Gly
    610                 615                 620

Met Arg Phe Arg Ile Ala Thr Asn Lys Gly Asp Ile Glu Gln Pro Thr
625                 630                 635                 640

Gly Ile Ala Phe Ser Gly Glu Val Glu Asp Met Leu Leu His Arg Ile
                645                 650                 655

Tyr Pro Pro Lys Gly Glu Lys Gln Thr Thr Asp Gly Phe Thr Gly Glu
            660                 665                 670

Thr Gln Thr Ala Val Leu His Phe Thr Pro Lys Gly Thr Asp Arg Ser
        675                 680                 685

Asp Asp Ser Val Asn Ala Val Met Ser Thr Gln Ala Pro Gln Ile Leu
    690                 695                 700

Asp Lys Gln Gly Gln Val Leu Thr Ala Val Asp Gly Asn Tyr Ile Arg
705                 710                 715                 720

Pro Glu Gly Thr Tyr Gln Val Thr Val Asn Gly Asn Asp Val Gln Val
                725                 730                 735

Thr Phe Thr Pro Lys Ala Asp Phe Ser Gly Thr Ala Asp Gly Ile Asn
            740                 745                 750

Ile Arg Trp Thr Asp Gln Asn Gly Thr Ser Thr Gly Trp Ala Ser Thr
        755                 760                 765

Asp Ala Ser Asp Pro Asn Met Asn Asp Leu Leu Asn Thr Met Asp Gly
    770                 775                 780

Ser Tyr Met Pro Thr Val Arg Lys Ile Pro Asn Tyr Glu Ser Ser Gly
785                 790                 795                 800
```

-continued

```
Leu Gln Gly Leu Glu Gln Asn Lys Thr Leu Val Phe Asn Asp Asp Asp
                805                 810                 815

Ala Asn Thr Pro Pro Val Thr Pro Asp Thr Thr Arg Pro Ala Ser Phe
            820                 825                 830

Val Asp Ala Ser Gly Gln Pro Val Ala Gly Asn Thr Val Pro Ala Met
        835                 840                 845

Ser Asn Gly Gln Gln Val Gly Thr Tyr Glu Leu Asp Pro Asn Thr
    850                 855                 860

<210> SEQ ID NO 29
<211> LENGTH: 2178
<212> TYPE: PRT
<213> ORGANISM: Streptococcus gordonii

<400> SEQUENCE: 29

Met Phe Phe Lys Arg Gln Lys Gly Gln Tyr His Glu Val Glu Arg Val
1               5                   10                  15

Thr Arg Phe Lys Leu Ile Lys Ser Gly Lys His Trp Leu Arg Ala Ala
            20                  25                  30

Thr Ser Gln Phe Gly Leu Leu Arg Leu Met Lys Gly Ala Asp Ile Ser
        35                  40                  45

Ser Val Glu Val Lys Val Ala Glu Glu Gln Ser Val Glu Lys Gly Gly
    50                  55                  60

Leu Asn Tyr Leu Lys Gly Ile Ile Ala Thr Gly Ala Val Leu Gly Gly
65                  70                  75                  80

Ala Val Val Thr Ser Ser Val Tyr Ala Glu Glu Gln Ala Leu
                85                  90                  95

Glu Lys Val Ile Asp Thr Arg Asp Val Leu Ala Thr Arg Gly Glu Ala
            100                 105                 110

Val Leu Ser Glu Glu Ala Ala Thr Thr Leu Ser Ser Glu Gly Ala Asn
        115                 120                 125

Pro Val Glu Ser Leu Ser Asp Thr Leu Ser Ala Ser Glu Ser Ala Ser
    130                 135                 140

Ala Asn Ser Val Ser Thr Ser Ile Ser Ile Ser Glu Ser Phe Ser Val
145                 150                 155                 160

Ser Ala Ser Ala Ser Leu Ser Ser Ser Ser Leu Ser Gln Ser Ser
                165                 170                 175

Ser Glu Ser Ala Ser Ala Ser Glu Ser Leu Ser Val Ser Ala Ser Thr
            180                 185                 190

Ser Gln Ser Phe Ser Ser Thr Thr Ser Ser Thr Gln Ser Ser Asn Asn
        195                 200                 205

Glu Ser Leu Ile Ser Ser Asp Ser Ser Asn Ser Leu Asn Thr Asn Gln
    210                 215                 220

Ser Val Ser Ala Arg Asn Gln Asn Ala Arg Val Arg Thr Arg Arg Ala
225                 230                 235                 240

Val Ala Ala Asn Asp Thr Glu Ala Pro Gln Val Lys Ser Gly Asp Tyr
                245                 250                 255

Val Val Tyr Arg Gly Glu Ser Phe Glu Tyr Tyr Ala Glu Ile Thr Asp
            260                 265                 270

Asn Ser Gly Gln Val Asn Arg Val Val Ile Arg Asn Val Glu Gly Gly
        275                 280                 285

Ala Asn Ser Thr Tyr Leu Ser Pro Asn Trp Val Lys Tyr Ser Thr Glu
    290                 295                 300
```

```
Asn Leu Gly Arg Pro Gly Asn Ala Thr Val Gln Asn Pro Leu Arg Thr
305                 310                 315                 320
Arg Ile Phe Gly Glu Val Pro Leu Asn Glu Ile Val Asn Glu Lys Ser
                325                 330                 335
Tyr Tyr Thr Arg Tyr Ile Val Ala Trp Asp Pro Ser Gly Asn Ala Thr
            340                 345                 350
Gln Met Val Asp Asn Ala Asn Arg Asn Gly Leu Glu Arg Phe Val Leu
        355                 360                 365
Thr Val Lys Ser Gln Asn Glu Lys Tyr Asp Pro Ala Glu Ser Ser Val
370                 375                 380
Thr Tyr Val Asn Asn Leu Ser Asn Leu Ser Thr Ser Glu Arg Glu Ala
385                 390                 395                 400
Val Ala Ala Val Arg Ala Ala Asn Pro Asn Ile Pro Pro Thr Ala
                405                 410                 415
Lys Ile Thr Val Ser Gln Asn Gly Thr Val Thr Ile Thr Tyr Pro Asp
                420                 425                 430
Lys Ser Thr Asp Thr Ile Pro Ala Asn Arg Val Val Lys Asp Leu Gln
                435                 440                 445
Ile Ser Lys Ser Asn Ser Ala Ser Gln Ser Ser Val Ser Ala Ser
450                 455                 460
Gln Ser Ala Ser Thr Ser Val Ser Ala Ser Ile Ser Ala Ser Met Ser
465                 470                 475                 480
Ala Ser Val Ser Val Ser Thr Ser Ala Ser Thr Ser Ala Ser Val Ser
                485                 490                 495
Ala Ser Glu Ser Ala Ser Thr Ser Ala Ser Val Ser Ala Ser Glu Ser
                500                 505                 510
Ala Ser Thr Ser Ala Ser Val Ser Ala Ser Lys Ser Ser Ser Thr Ser
                515                 520                 525
Ala Ser Val Ser Ala Ser Glu Ser Ala Ser Thr Ser Ala Ser Val Ser
                530                 535                 540
Ala Ser Glu Ser Ala Ser Thr Ser Ala Ser Val Ser Ala Ser Glu Ser
545                 550                 555                 560
Ala Ser Thr Ser Ala Ser Val Ser Ala Ser Thr Ser Ala Ser Thr Ser
                565                 570                 575
Ala Ser Val Ser Ala Ser Glu Ser Ala Ser Thr Ser Ala Ser Val Ser
                580                 585                 590
Ala Ser Glu Ser Ala Ser Thr Ser Ala Ser Val Ser Ala Ser Glu Ser
                595                 600                 605
Ala Ser Thr Ser Ala Ser Val Ser Ala Ser Glu Ser Ala Ser Thr Ser
                610                 615                 620
Ala Ser Val Ser Ala Ser Glu Ser Ser Ser Thr Ser Ala Ser Val Ser
625                 630                 635                 640
Ala Ser Glu Ser Ala Ser Thr Ser Ala Ser Val Ser Ala Ser Glu Ser
                645                 650                 655
Ala Ser Thr Ser Ala Ser Val Ser Ala Ser Thr Ser Ala Ser Thr Ser
                660                 665                 670
Ala Ser Val Ser Ala Ser Thr Ser Ala Ser Thr Ser Ala Ser Val Ser
                675                 680                 685
Ala Ser Thr Ser Ala Ser Thr Ser Ala Ser Val Ser Ala Ser Glu Ser
                690                 695                 700
Ala Ser Thr Ser Ala Ser Val Ser Ala Ser Glu Ser Ala Ser Thr Ser
705                 710                 715                 720
```

Ala Ser Val Ser Ala Ser Thr Ser Ala Ser Thr Ser Ala Ser Val Ser
                725                 730                 735

Ala Ser Thr Ser Ala Ser Thr Ser Ala Ser Val Ser Ala Ser Glu Ser
                740                 745                 750

Ala Ser Thr Ser Ala Ser Val Ser Ala Ser Thr Ser Ala Ser Thr Ser
                755                 760                 765

Ala Ser Val Ser Ala Ser Glu Ser Ala Ser Thr Ser Ala Ser Val Ser
                770                 775                 780

Ala Ser Thr Tyr Ala Ser Thr Ser Ala Ser Val Ser Ala Ser Glu Ser
785                 790                 795                 800

Ala Ser Thr Ser Ala Ser Val Ser Ala Ser Glu Ser Ala Ser Thr Ser
                805                 810                 815

Ala Ser Val Ser Ala Ser Thr Ser Ala Ser Thr Ser Ala Ser Val Ser
                820                 825                 830

Ala Ser Glu Ser Ala Ser Thr Ser Ala Ser Val Ser Ala Ser Glu Ser
                835                 840                 845

Ala Ser Thr Ser Ala Ser Val Ser Ala Ser Glu Ser Ala Ser Thr Ser
                850                 855                 860

Ala Ser Val Ser Ala Ser Thr Ser Ala Ser Thr Ser Ala Ser Val Ser
865                 870                 875                 880

Ala Ser Glu Ser Ala Ser Thr Ser Ala Ser Val Ser Ala Ser Glu Ser
                885                 890                 895

Ala Ser Thr Ser Ala Ser Val Ser Ala Ser Glu Ser Ala Ser Thr Ser
                900                 905                 910

Ala Ser Val Ser Ala Ser Glu Ser Ala Ser Thr Ser Ala Ser Val Ser
                915                 920                 925

Ala Ser Thr Ser Ala Ser Thr Ser Ala Ser Val Ser Ala Ser Glu Ser
                930                 935                 940

Ala Ser Thr Ser Ala Ser Val Ser Ala Ser Glu Ser Ala Ser Thr Ser
945                 950                 955                 960

Ala Ser Val Ser Ala Ser Glu Ser Ala Ser Thr Ser Ala Ser Val Ser
                965                 970                 975

Ala Ser Glu Ser Ala Ser Thr Ser Ala Ser Ile Ser Ala Ser Glu Ser
                980                 985                 990

Ala Ser Thr Ser Ala Ser Val Ser Ala Ser Glu Ser Ala Ser Thr Ser
                995                1000                1005

Ala Ser Val Ser Ala Ser Thr Ser Ala Ser Thr Ser Ala Ser Val
               1010                1015                1020

Ser Ala Ser Glu Ser Ala Ser Thr Ser Ala Ser Val Ser Ala Ser
               1025                1030                1035

Glu Ser Ala Ser Thr Ser Ala Ser Val Ser Ala Ser Glu Ser Ala
               1040                1045                1050

Ser Thr Ser Ala Ser Val Ser Ala Ser Glu Ser Ala Ser Thr Ser
               1055                1060                1065

Ala Ser Val Ser Ala Ser Glu Ser Ala Ser Thr Ser Ala Ser Val
               1070                1075                1080

Ser Ala Ser Thr Ser Ala Ser Thr Ser Ala Ser Val Ser Ala Ser
               1085                1090                1095

Glu Ser Ser Thr Ser Ala Ser Val Ser Ala Ser Glu Ser Ala
               1100                1105                1110

Ser Thr Ser Ser Ser Val Ser Ala Ser Glu Ser Ala Ser Thr Ser
               1115                1120                1125

-continued

```
Ala Ser Val Ser Ala Ser Glu Ser Ala Ser Thr Ser Ala Ser Val
    1130                1135                1140

Ser Ala Ser Glu Ser Ala Ser Thr Ser Ala Ser Val Ser Ala Ser
    1145                1150                1155

Glu Ser Ala Ser Thr Ser Ala Ser Val Ser Ala Ser Glu Ser Ala
    1160                1165                1170

Ser Thr Ser Ala Ser Val Ser Ala Ser Glu Ser Ala Ser Thr Ser
    1175                1180                1185

Ala Ser Val Ser Ala Ser Glu Ser Ala Ser Thr Ser Ala Ser Val
    1190                1195                1200

Ser Ala Ser Thr Ser Ala Ser Thr Ser Ala Ser Val Ser Ala Ser
    1205                1210                1215

Glu Ser Ala Ser Thr Ser Ala Ser Val Ser Ala Ser Glu Ser Ala
    1220                1225                1230

Ser Thr Ser Ala Ser Val Ser Ala Ser Thr Ser Ala Ser Thr Ser
    1235                1240                1245

Ala Ser Val Ser Ala Ser Glu Ser Ala Ser Thr Ser Ala Ser Val
    1250                1255                1260

Ser Ala Ser Glu Ser Ala Ser Thr Ser Ala Ser Val Ser Ala Ser
    1265                1270                1275

Glu Ser Ala Ser Thr Ser Ala Ser Val Ser Ala Ser Thr Ser Ala
    1280                1285                1290

Ser Thr Ser Ala Ser Val Ser Ala Ser Glu Ser Ala Ser Thr Ser
    1295                1300                1305

Ala Ser Val Ser Ala Ser Glu Ser Ala Ser Met Ser Ala Ser Val
    1310                1315                1320

Ser Ala Ser Glu Ser Ala Ser Thr Ser Ala Ser Val Ser Ala Ser
    1325                1330                1335

Glu Ser Ala Ser Thr Ser Ala Ser Val Ser Ala Ser Glu Ser Ala
    1340                1345                1350

Ser Thr Ser Ala Ser Val Ser Ala Ser Glu Ser Ala Ser Thr Ser
    1355                1360                1365

Ala Ser Val Ser Ala Ser Glu Ser Ala Ser Thr Ser Ala Ser Val
    1370                1375                1380

Ser Ala Ser Glu Ser Ala Ser Thr Ser Ala Ser Val Cys Ala Ser
    1385                1390                1395

Glu Ser Ala Tyr Thr Ser Ala Ser Ala Ser Ala Ser Glu Ser Ala
    1400                1405                1410

Ser Thr Ser Ala Ser Val Ser Ala Ser Glu Ser Ala Ser Thr Ser
    1415                1420                1425

Ala Ser Val Ser Ala Ser Glu Ser Ala Tyr Thr Ser Ala Ser Val
    1430                1435                1440

Ser Ala Ser Glu Ser Gly Ser Thr Ser Ala Ser Val Ser Ala Ser
    1445                1450                1455

Glu Ser Ala Ser Thr Ser Ala Ser Val Ser Ala Ser Glu Ser Ala
    1460                1465                1470

Ser Thr Ser Ala Ser Val Ser Ala Ser Thr Ser Ala Ser Thr Ser
    1475                1480                1485

Ala Ser Val Cys Ala Ser Ala Ser Ser Ser Thr Ser Ala Ser Val
    1490                1495                1500

Ser Ala Ser Gly Ser Ala Ser Thr Ser Ala Ser Val Ser Ala Ser
    1505                1510                1515
```

```
Glu Ser Ala Ser Thr Ser Ala Ser Val Ser Ala Ser Thr Ser Ala
    1520                1525                1530

Ser Thr Ser Ala Ser Val Ser Ala Ser Glu Ser Ala Ser Thr Ser
    1535                1540                1545

Ala Ser Val Ser Ala Ser Glu Ser Ala Ser Thr Ser Ala Ser Val
    1550                1555                1560

Ser Ala Ser Glu Ser Ala Ser Thr Ser Ala Ser Val Ser Thr Ser
    1565                1570                1575

Glu Ser Ala Ser Thr Ser Ala Ser Val Ser Ala Ser Glu Ser Ala
    1580                1585                1590

Ser Thr Ser Ala Ser Val Ser Ala Ser Glu Ser Ala Ser Thr Ser
    1595                1600                1605

Ala Ser Val Ser Ala Ser Glu Ser Ser Ser Thr Ser Ala Ser Val
    1610                1615                1620

Ser Ala Ser Glu Ser Ala Ser Thr Ser Ala Ser Val Ser Ala Ser
    1625                1630                1635

Glu Ser Ala Ser Thr Ser Ala Ser Val Ser Ala Ser Glu Ser Ala
    1640                1645                1650

Ser Thr Ser Ala Ser Val Ser Ala Ser Glu Ser Ala Ser Thr Ser
    1655                1660                1665

Val Ser Val Ser Ala Ser Glu Ser Ala Ser Thr Ser Ala Ser Val
    1670                1675                1680

Ser Ala Ser Glu Ser Ala Ser Ser Ser Ala Ser Val Ser Ala Ser
    1685                1690                1695

Lys Ser Ala Ser Met Ser Ala Ser Val Leu Ala Ser Glu Ser Ala
    1700                1705                1710

Ser Thr Ser Ala Ser Val Ser Ala Ser Glu Ser Ala Ser Thr Ser
    1715                1720                1725

Ala Ser Val Ser Ala Ser Glu Ser Ala Ser Thr Ser Ala Ser Val
    1730                1735                1740

Ser Ala Ser Glu Ser Ala Ser Thr Ser Ala Ser Val Ser Ala Ser
    1745                1750                1755

Glu Ser Ala Ser Thr Ser Ala Ser Val Ser Ala Ser Glu Ser Ala
    1760                1765                1770

Ser Thr Ser Ala Ser Val Ser Ala Ser Glu Ser Ala Ser Thr Ser
    1775                1780                1785

Ala Ser Val Ser Ala Ser Thr Ser Ala Ser Thr Ser Ala Ser Val
    1790                1795                1800

Ser Ala Ser Glu Ser Ala Ser Thr Ser Ala Ser Val Ser Ala Ser
    1805                1810                1815

Glu Ser Ala Ser Thr Ser Ala Ser Val Ser Ala Ser Glu Ser Ala
    1820                1825                1830

Ser Thr Ser Ala Ser Val Ser Ala Ser Glu Ser Val Ser Ala Asn
    1835                1840                1845

Glu Ser Ala Ser Thr Ser Ala Ser Val Ser Ala Ser Thr Ser Ala
    1850                1855                1860

Ser Thr Ser Ala Ser Val Ser Ser Ser Glu Ser Ala Ser Thr Ser
    1865                1870                1875

Ala Ser Val Ser Ala Ser Glu Ser Ala Ser Thr Ser Ala Ser Val
    1880                1885                1890

Ser Ala Ser Glu Ser Ala Ser Thr Ser Ala Ser Val Ser Ala Ser
    1895                1900                1905
```

Glu Ser Ala Ser Ile Ser Ala Ser Ile Ser Ala Ser Glu Ser Ser
        1910                1915                1920

Ser Thr Ser Ala Ser Val Ser Ala Ser Glu Ser Ala Ser Thr Ser
        1925                1930                1935

Ala Ser Val Ser Ala Ser Thr Ser Thr Ser Thr Ser Ala Ser Val
        1940                1945                1950

Ser Ala Ser Glu Ser Ala Ser Thr Ser Ala Ser Val Phe Ala Ser
        1955                1960                1965

Glu Ser Ala Ser Thr Ser Ala Ser Val Ser Ala Ser Glu Ser Ala
        1970                1975                1980

Ser Thr Ser Ala Ser Val Ser Ala Ser Thr Ser Ala Ser Thr Ser
        1985                1990                1995

Ala Ser Val Ser Ala Ser Glu Ser Ala Ser Thr Ser Ala Ser Ile
        2000                2005                2010

Ser Ala Ser Glu Ser Ala Ser Thr Ser Ala Ser Ile Ser Ala Ser
        2015                2020                2025

Glu Ser Ser Thr Ser Ala Ser Val Ser Ala Ser Thr Ser Ala
        2030                2035                2040

Ser Thr Ser Ala Ser Val Ser Ala Ser Glu Ser Thr Ser Thr Ser
        2045                2050                2055

Val Ser Ile Ser Ala Ser Glu Ser Val Ser Ile Ser Thr Ser Val
        2060                2065                2070

Ser Gln Ser Met Ser Val Ser Glu Ser Leu Ser Leu Ser Val Ser
        2075                2080                2085

Thr Ser Thr Leu His Ser Gln Leu Asn Gly Ile Tyr Glu Ser Glu
        2090                2095                2100

Leu Asn Ser Leu Ser Leu Ser Glu Ser Leu Ser Met Ser Gln Ser
        2105                2110                2115

Leu Ser Gln Ser Leu Ser Asp Ser Gln Ser Thr Ser Ala Thr Gln
        2120                2125                2130

Ser Met His Asp Arg Ile Ser Lys Gly Gln Leu Pro Arg Thr Gly
        2135                2140                2145

Glu Ser Glu Ser Lys Ala Ser Ile Leu Ala Leu Gly Ile Gly Ala
        2150                2155                2160

Leu Gly Leu Ala Phe Lys Lys Arg Lys Lys Asn Glu Ser Glu Asp
        2165                2170                2175

<210> SEQ ID NO 30
<211> LENGTH: 1352
<212> TYPE: PRT
<213> ORGANISM: Streptococcus pyogenes

<400> SEQUENCE: 30

Met Lys Gln Met Glu Thr Lys Gly Tyr Gly Tyr Phe Arg Lys Thr Lys
1               5                   10                  15

Ala Tyr Gly Leu Val Cys Gly Ile Thr Leu Ala Gly Ala Leu Thr Leu
                20                  25                  30

Gly Thr Thr Ser Val Ser Ala Asp Asp Val Thr Leu Asn Pro Ala
        35                  40                  45

Thr Asn Leu Thr Thr Leu Gln Thr Pro Pro Thr Ala Asp Gln Thr Gln
    50                  55                  60

Leu Ala His Gln Ala Gly Gln Gln Ser Gly Glu Leu Val Ser Glu Val
65                  70                  75                  80

```
Ser Asn Thr Glu Trp Asp Asn Ala Val Thr Thr Ala Gln Lys Ala Gly
                85                  90                  95

Val Thr Val Lys Gln Ser Glu Lys Val Thr His Asp Ser Leu Ser Ser
            100                 105                 110

Ala Gln Ala Asp Leu Glu Lys Gln Thr Gln Ala Val Thr Glu Ala Thr
        115                 120                 125

Thr Lys Gln Glu Ala Asn Thr Thr Ala Ile Asn Gln Ala Val Ser Glu
130                 135                 140

Asn Lys Ala Ile Asp Gln Ala Asn Arg Asp Glu Lys Ala Arg Val Asp
145                 150                 155                 160

Ala Leu Asn Thr Lys Gly Glu Ala Asp Thr Lys Ala Lys Asn Glu Thr
                165                 170                 175

Gly Gln Ala Gln Val Asp Ala Gln Asn Lys Gln Ala Gln Ala Ala Ala
            180                 185                 190

Asp Ala Met Asn Ala Lys Leu Lys Ala Asp Tyr Glu Ala Lys Leu Thr
        195                 200                 205

Glu Ile Lys Gln Ile Glu Ser Glu Asn Glu Ala Ile Arg Gln Arg Asn
210                 215                 220

Gln Gln Ala Ser Gln Ala Thr His Gln Ala Asn Gln Ala Ala Gln Ala
225                 230                 235                 240

Ala Tyr Gln Glu Lys Leu Ala Glu Ile Glu Arg Ile Lys Ala Glu Asn
                245                 250                 255

Ala Ala Ile Arg Asp Arg Asn Ala Lys Ala Gln Gln Glu Ala Glu Arg
            260                 265                 270

Gln Asn Gln Ala Leu Gln Ala Ala Tyr Glu Ala Lys Leu Ala Glu Ile
        275                 280                 285

Lys Gln Ile Glu Ser Glu Asn Ala Ala Ile Arg Gln Arg Asn Glu Gln
290                 295                 300

Ala Gly Gln Ala Thr Asn Gln Thr Asn Gln Ala Ala Gln Ala Ala Tyr
305                 310                 315                 320

Gln Glu Lys Leu Ala Glu Ile Glu Arg Ile Lys Ala Gly Asn Ala Ala
                325                 330                 335

Ile Arg Asp Arg Asn Ala Lys Ala Gln Gln Glu Ala Glu Arg Gln Asn
            340                 345                 350

Gln Ala Leu Gln Ala Ala Tyr Glu Ala Lys Leu Ala Glu Ile Lys Gln
        355                 360                 365

Ile Glu Ser Glu Asn Ala Ala Ile Arg Lys Arg Asn Glu Gln Ala Gly
370                 375                 380

Gln Thr Thr Asn Gln Thr Asn Gln Ala Ala Gln Ala Ala Tyr Gln Glu
385                 390                 395                 400

Lys Leu Ala Glu Ile Glu Arg Ile Asn Ala Glu Asn Ala Ala Ile Arg
                405                 410                 415

Asp Arg Asn Thr Lys Ala Arg Gln Glu Ala Glu Arg Gln Asn Gln Gln
            420                 425                 430

Leu Lys Thr Thr Tyr Glu Ala Gln Leu Ser Ala Tyr Gln Gln Ala Leu
        435                 440                 445

Gln Ala Lys Lys Glu Ala Glu Asn Lys Ala Ile Asp Gln Val Val Phe
450                 455                 460

Gly Ile Asp Ala Lys Ala Asn Gly Val Asp Asn Ala Glu Tyr Gly Asn
465                 470                 475                 480

Ser Ile Met Thr Val Thr Thr Gln Pro Asp Gly Ser Phe Val Phe Lys
                485                 490                 495
```

```
His Asp Met Ile Asp Gly Val Lys Thr Ile Gly His Gly Thr Leu Thr
            500                 505                 510
Gly Lys Ile Asn His His Tyr Glu Ala Asn Lys Asp Gly Ser Ile Thr
            515                 520                 525
Ala Tyr Ile Asp Ser Val Thr Phe Asp Lys Tyr Glu Tyr Gln Asn Val
            530                 535                 540
Ala Lys Asn Asp Ala Val Asp Lys Asn Ile Ala Phe Arg Ile Leu Ser
545                 550                 555                 560
Ala Thr Gly Gln Glu Leu Phe Val Lys Ala His Asp Gly Asp Lys Thr
            565                 570                 575
Phe Ser Glu Thr Leu Asn Lys Thr Val Ser Leu Lys Leu Thr Tyr Gln
            580                 585                 590
Leu Lys Pro His Glu Ala Val Lys Asp Ile Lys Val Phe Gln Leu His
            595                 600                 605
Asp Asp Trp Val His Asp Thr His Gly Ser Ala Leu Val Ser Tyr Val
            610                 615                 620
Asn Asn Asn Asp Ala Val Pro His Ile Glu Val Pro Glu Lys Pro Val
625                 630                 635                 640
Glu Pro Asp Met Val Thr Pro Lys Val Glu Gln Glu Lys Pro Val Pro
            645                 650                 655
Glu Ala Pro Gln Lys Pro Thr Asp Gly Val Pro Asn Leu Glu Lys Glu
            660                 665                 670
Lys Pro Val Pro Pro Thr Pro Val Lys Pro Glu Ala Val Lys Pro Val
            675                 680                 685
Leu Glu Gln Glu Lys Pro Val Pro Glu Ala Pro Gln Lys Pro Thr Asp
            690                 695                 700
Asp Val Pro Asn Leu Glu Lys Glu Lys Pro Val Pro Pro Thr Pro Val
705                 710                 715                 720
Lys Pro Glu Ala Val Lys Pro Val Leu Glu Gln Glu Lys Pro Val Pro
            725                 730                 735
Glu Ala Pro Gln Lys Pro Thr Asp Asp Val Pro Asn Leu Glu Lys Glu
            740                 745                 750
Lys Pro Val Pro Pro Thr Pro Val Glu Pro Glu Ala Ile Lys Pro Asp
            755                 760                 765
Leu Gln Ser Phe Thr Pro Glu Val Tyr Asp Pro Ile Lys Pro Val Val
            770                 775                 780
Lys Pro His Val Thr Val Pro Glu Lys Val Val Tyr Glu Val Met Val
785                 790                 795                 800
His Pro Val Gln Val Lys Gln Thr Pro Thr Asn Val Lys Ser Val Thr
            805                 810                 815
Asn Ser Asp Gln Val Asn Ile Asp Gly Gln Leu Val Pro Lys Gly Ser
            820                 825                 830
Thr Val Thr Trp Glu Leu Val Asn Thr Ser Leu Lys Ala Gly Arg Gln
            835                 840                 845
Asp Ile Thr Ser Tyr Glu Leu Thr Asp Pro Leu Pro Asp Gly Phe Glu
            850                 855                 860
Leu Asp Val Thr Ala Thr Gln Thr Leu Ser Pro Glu Trp Val Ile Thr
865                 870                 875                 880
Thr Asp Glu Ala Gly Lys Val Ser Leu Lys Ala Ser Gln Ser Leu Leu
            885                 890                 895
Ala His Phe Asn Ala Lys Arg Asp Gln Asp Val Glu Val Pro Lys Val
            900                 905                 910
```

-continued

```
Ser Leu Val Gly Arg Leu Leu Asn Asp Ala Gly Thr Tyr His Asn Thr
        915                 920                 925

Phe Lys Thr Val Val Thr Thr Pro Thr Gly Ser Tyr Thr Val Ile Ser
        930                 935                 940

Asn Thr Pro Val Ile Tyr Thr Pro Gly Asn Asp Pro Lys Thr Pro Arg
945                 950                 955                 960

Asn Pro Gly Gly Asp Asn Pro Thr Pro His Asp Asn Leu Ile Gln Pro
                965                 970                 975

Thr Lys Thr Ile Val Asp Asp Lys Gly Gln Ser Ile Asp Gly Lys Ser
                980                 985                 990

Val Leu Pro Asn Ser Thr Leu Thr Tyr Val Ala Lys Gln Asp Phe Asp
        995                 1000                1005

Gln Tyr Lys Gly Met Thr Ala Ala Lys Glu Ser Val Met Lys Gly
        1010                1015                1020

Phe Ile Tyr Val Asp Asp Tyr Lys Asp Glu Ala Ile Asp Gly His
        1025                1030                1035

Ser Leu Val Val Asn Ser Ile Lys Ala Ala Asn Gly Asp Asp Val
        1040                1045                1050

Thr Asn Leu Leu Glu Met Arg His Val Leu Ser Gln Asp Thr Leu
        1055                1060                1065

Asp Asp Lys Leu Lys Ala Leu Ile Lys Ala Ser Gly Ile Ser Pro
        1070                1075                1080

Val Gly Glu Phe Tyr Met Trp Val Ala Lys Asp Pro Ala Ala Phe
        1085                1090                1095

Tyr Lys Ala Tyr Val Gln Lys Gly Leu Asp Ile Thr Tyr Asn Leu
        1100                1105                1110

Ser Phe Lys Leu Lys Gln Asp Phe Lys Lys Gly Asp Ile Thr Asn
        1115                1120                1125

Gln Thr Tyr Gln Ile Asp Phe Gly Asn Gly Tyr Tyr Gly Asn Ile
        1130                1135                1140

Val Val Asn His Leu Ser Glu Leu Thr Val His Lys Asp Val Phe
        1145                1150                1155

Asp Lys Glu Gly Gly Gln Ser Ile Asn Ala Gly Thr Val Lys Val
        1160                1165                1170

Gly Asp Glu Val Thr Tyr Arg Leu Glu Gly Trp Val Val Pro Thr
        1175                1180                1185

Asn Arg Gly Tyr Asp Leu Thr Glu Tyr Lys Phe Val Asp Gln Leu
        1190                1195                1200

Gln His Thr His Asp Leu Tyr Gln Lys Asp Lys Val Leu Ala Thr
        1205                1210                1215

Val Asp Ile Thr Leu Ser Asp Gly Ser Val Ile Thr Lys Gly Thr
        1220                1225                1230

Asp Leu Ala Lys Tyr Thr Glu Thr Val Tyr Asn Lys Glu Thr Gly
        1235                1240                1245

His Tyr Glu Leu Ala Phe Lys Gln Asp Phe Leu Ala Lys Val Val
        1250                1255                1260

Arg Ser Ser Glu Phe Gly Ala Asp Ala Phe Val Val Val Lys Arg
        1265                1270                1275

Ile Lys Ala Gly Asp Val Ala Asn Glu Tyr Thr Leu Tyr Val Asn
        1280                1285                1290

Gly Asn Pro Val Lys Ser Asn Lys Val Thr Thr His Thr Pro Glu
        1295                1300                1305
```

Gln Pro Gln Pro Val Thr Pro Lys Ala Pro Ala Leu Pro Ser Thr
    1310                1315                1320

Gly Glu Gln Gly Val Ser Ile Leu Thr Ala Leu Gly Ala Ala Leu
    1325                1330                1335

Leu Ser Leu Leu Gly Tyr Val Gly Leu Lys Lys Arg Gln Gln
    1340                1345                1350

<210> SEQ ID NO 31
<211> LENGTH: 932
<212> TYPE: PRT
<213> ORGANISM: Streptococcus agalactiae

<400> SEQUENCE: 31

Met Asn Ser Gln Glu Thr Lys Gly His Gly Phe Phe Arg Lys Ser Lys
1               5                   10                  15

Ala Tyr Gly Leu Val Cys Gly Ile Ala Leu Ala Gly Ala Phe Thr Leu
            20                  25                  30

Ala Thr Ser Gln Val Ser Ala Asp Gln Val Thr Thr Gln Ala Thr Thr
        35                  40                  45

Gln Thr Val Thr Gln Asn Gln Ala Glu Thr Val Thr Ser Thr Gln Leu
    50                  55                  60

Asp Lys Ala Val Asp Thr Ala Lys Ala Ala Val Ala Val Thr Thr
65                  70                  75                  80

Thr Thr Ala Val Asn His Ala Thr Thr Thr Asp Ala Gln Ala Asp Leu
            85                  90                  95

Ala Asn Gln Thr Gln Ala Val Lys Asp Val Thr Ala Lys Ala Gln Ala
        100                 105                 110

Asn Thr Gln Ala Ile Lys Asp Ala Thr Ala Glu Asn Ala Lys Ile Asp
    115                 120                 125

Ala Glu Asn Lys Ala Glu Ala Glu Arg Val Ala Lys Ala Asn Lys Ala
130                 135                 140

Gly Gln Ala Glu Val Asp Ala Arg Asn Lys Ala Gly Gln Ala Ala Val
145                 150                 155                 160

Asp Ala Arg Asn Lys Ala Lys Gln Gln Ala Gln Asp Asp Gln Lys Ala
            165                 170                 175

Lys Ile Asp Ala Glu Asn Lys Ala Glu Ser Gln Arg Val Ser Gln Leu
        180                 185                 190

Asn Ala Gln Asn Lys Ala Lys Ile Asp Ala Glu Asn Lys Asp Ala Gln
    195                 200                 205

Ala Lys Ala Asp Ala Thr Asn Ala Gln Leu Gln Lys Asp Tyr Gln Thr
210                 215                 220

Lys Leu Ala Asn Ile Lys Ser Val Glu Ala Tyr Asn Ala Gly Val Arg
225                 230                 235                 240

Gln Arg Asn Lys Asp Ala Gln Ala Lys Ala Asp Ala Thr Asn Ala Gln
            245                 250                 255

Leu Gln Lys Asp Tyr Gln Ala Lys Leu Ala Leu Tyr Asn Gln Ala Leu
        260                 265                 270

Lys Ala Lys Ala Glu Ala Asp Lys Gln Ser Ile Asn Asn Val Ala Phe
    275                 280                 285

Asp Ile Lys Ala Gln Ala Lys Gly Val Asp Asn Ala Glu Tyr Gly Asn
290                 295                 300

Ser Ile Met Thr Ala Lys Thr Lys Pro Asp Gly Ser Phe Glu Phe Asn
305                 310                 315                 320

His Asp Met Ile Asp Gly Val Lys Thr Ile Gly Tyr Gly Lys Leu Thr
            325                 330                 335

Gly Lys Val Asn His His Tyr Val Ala Asn Lys Asp Gly Ser Val Thr
                340                 345                 350

Ala Phe Val Asp Ser Val Thr Leu Tyr Lys Tyr Glu Tyr Arg Asn Val
        355                 360                 365

Ala Gln Asn Ala Ala Val Asn Gln Asn Ile Val Phe Arg Val Leu Thr
370                 375                 380

Lys Asp Gly Arg Pro Ile Phe Glu Lys Ala His Asn Gly Asn Lys Thr
385                 390                 395                 400

Phe Ala Glu Thr Leu Asn Lys Thr Leu Gln Leu Asn Leu Lys Tyr Glu
                405                 410                 415

Leu Lys Pro His Ala Ser Ser Gly Asn Val Glu Val Phe Lys Ile His
                420                 425                 430

Asp Asp Trp Val His Asp Thr His Gly Ser Ala Leu Val Ser Tyr Val
        435                 440                 445

Asn Asn Asn Asp Ala Val Pro Asn Val Val Ile Pro Glu Gln Pro Thr
450                 455                 460

Pro Pro Lys Pro Glu Lys Val Thr Pro Glu Ala Glu Lys Pro Val Pro
465                 470                 475                 480

Glu Lys Pro Val Glu Pro Lys Leu Val Thr Pro Val Leu Lys Thr Tyr
                485                 490                 495

Thr Pro Val Lys Phe Ile Pro Arg Glu Tyr Lys Pro Val Pro Ser Thr
                500                 505                 510

Pro Glu Thr Phe Thr Pro Glu Lys Phe Thr Pro Ala Gln Pro Lys Val
                515                 520                 525

Lys Pro His Val Ser Val Pro Glu Lys Ile Asn Tyr Lys Val Ala Val
                530                 535                 540

His Pro Val Gln Ile Pro Lys Ala Thr Pro Thr Lys Lys Val Leu Asp
545                 550                 555                 560

Glu Asn Gly Gln Ser Ile Asn Gly Lys Ser Val Leu Pro Asn Ala Thr
                565                 570                 575

Leu Asp Tyr Val Ala Lys Gln Asn Phe Ser Gln Tyr Lys Gly Ile Lys
                580                 585                 590

Ala Ser Ala Glu Ala Ile Ala Lys Gly Phe Ala Phe Val Asp Gln Pro
                595                 600                 605

Asn Glu Ala Leu Ala Glu Leu Thr Val Lys Ser Ile Lys Ala Ser Asn
                610                 615                 620

Gly Asp Asp Val Ser Ser Leu Leu Glu Met Arg His Val Leu Ser Lys
625                 630                 635                 640

Asp Thr Leu Asp Gln Lys Leu Gln Ser Leu Ile Lys Glu Ala Gly Ile
                645                 650                 655

Ser Pro Val Gly Glu Phe Tyr Met Trp Thr Ala Lys Asp Pro Gln Ala
                660                 665                 670

Phe Tyr Lys Ala Tyr Val Gln Lys Gly Leu Asp Ile Thr Tyr Asn Leu
                675                 680                 685

Ser Phe Lys Val Lys Lys Glu Phe Thr Lys Gly Gln Ile Lys Asn Gly
                690                 695                 700

Val Ala Gln Ile Asp Phe Gly Asn Gly Tyr Thr Gly Asn Ile Val Val
705                 710                 715                 720

Asn Asp Leu Thr Thr Pro Glu Val His Lys Asp Val Leu Asp Lys Glu
                725                 730                 735

Asp Gly Lys Ser Ile Asn Asn Gly Thr Val Lys Leu Gly Asp Glu Val
                740                 745                 750

```
Thr Tyr Lys Leu Glu Gly Trp Val Pro Ala Asn Arg Gly Tyr Asp
            755                 760                 765

Leu Phe Glu Tyr Lys Phe Val Asp His Leu Gln His Thr His Asp Leu
770                 775                 780

Tyr Leu Lys Asp Lys Val Val Ala Lys Val Ala Ile Thr Leu Lys Asp
785                 790                 795                 800

Gly Thr Val Ile Pro Lys Gly Thr Asn Leu Val Gln Tyr Thr Glu Thr
                805                 810                 815

Val Tyr Asn Lys Glu Thr Gly Arg Tyr Glu Leu Ala Phe Lys Ala Asp
            820                 825                 830

Phe Leu Ala Gln Val Ser Arg Ser Ser Ala Phe Gly Ala Asp Asp Phe
835                 840                 845

Ile Val Val Lys Arg Ile Lys Ala Gly Asp Val Tyr Asn Thr Ala Asp
850                 855                 860

Phe Phe Val Asn Gly Asn Lys Val Lys Thr Glu Thr Val Val Thr His
865                 870                 875                 880

Thr Pro Glu Lys Pro Lys Pro Val Met Pro Gln Lys Val Thr Pro Lys
                885                 890                 895

Ala Pro Ala Leu Pro Ser Thr Gly Glu Gln Gly Val Ser Val Leu Thr
            900                 905                 910

Val Leu Gly Ala Ala Leu Leu Ser Leu Leu Gly Leu Val Gly Phe Lys
915                 920                 925

Lys Arg Gln Gln
    930

<210> SEQ ID NO 32
<211> LENGTH: 719
<212> TYPE: PRT
<213> ORGANISM: Streptococcus pneumoniae

<400> SEQUENCE: 32

Met Leu Lys Ile Val Lys Lys Leu Glu Val Leu Met Lys Tyr Phe Val
1               5                   10                  15

Pro Asn Glu Val Phe Ser Ile Arg Lys Leu Lys Val Gly Thr Cys Ser
                20                  25                  30

Val Leu Leu Ala Ile Ser Ile Leu Gly Ser Gln Gly Ile Leu Ser Asp
            35                  40                  45

Glu Val Val Thr Ser Ser Pro Met Ala Thr Lys Glu Ser Ser Asn
        50                  55                  60

Ala Ile Thr Asn Asp Leu Asp Asn Ser Pro Thr Val Asn Gln Asn Arg
65                  70                  75                  80

Ser Ala Glu Met Ile Ala Ser Asn Ser Thr Thr Asn Gly Leu Asp Asn
                85                  90                  95

Ser Leu Ser Val Asn Ser Ile Ser Ser Asn Gly Thr Ile Arg Ser Asn
            100                 105                 110

Ser Gln Leu Asp Asn Arg Thr Val Glu Ser Thr Val Thr Ser Thr Asn
        115                 120                 125

Glu Asn Lys Ser Tyr Lys Glu Asp Val Ile Ser Asp Arg Ile Ile Lys
    130                 135                 140

Lys Glu Phe Glu Asp Thr Ala Leu Ser Val Lys Asp Tyr Gly Ala Val
145                 150                 155                 160

Gly Asp Gly Ile His Asp Asp Arg Gln Ala Ile Gln Asp Ala Ile Asp
                165                 170                 175

Ala Ala Ala Gln Gly Leu Gly Gly Gly Asn Val Tyr Phe Pro Glu Gly
            180                 185                 190
```

```
Thr Tyr Leu Val Lys Glu Ile Val Phe Leu Lys Ser His Thr His Leu
            195                 200                 205

Glu Leu Asn Glu Lys Ala Thr Ile Leu Asn Gly Ile Asn Ile Lys Asn
        210                 215                 220

His Pro Ser Ile Val Phe Met Thr Gly Leu Phe Thr Asp Asp Gly Ala
225                 230                 235                 240

Gln Val Glu Trp Gly Pro Thr Glu Asp Ile Ser Tyr Ser Gly Gly Thr
                245                 250                 255

Ile Asp Met Asn Gly Ala Leu Asn Glu Glu Gly Thr Lys Ala Lys Asn
                260                 265                 270

Leu Pro Leu Ile Asn Ser Ser Gly Ala Phe Ala Ile Gly Asn Ser Asn
            275                 280                 285

Asn Val Thr Ile Lys Asn Val Thr Phe Lys Asp Ser Tyr Gln Gly His
        290                 295                 300

Ala Ile Gln Ile Ala Gly Ser Lys Asn Val Leu Val Asp Asn Ser Arg
305                 310                 315                 320

Phe Leu Gly Gln Ala Leu Pro Lys Thr Met Lys Asp Gly Gln Ile Ile
                325                 330                 335

Ser Lys Glu Ser Ile Gln Ile Glu Pro Leu Thr Arg Lys Gly Phe Pro
            340                 345                 350

Tyr Ala Leu Asn Asp Asp Gly Lys Lys Ser Glu Asn Val Thr Ile Gln
        355                 360                 365

Asn Ser Tyr Phe Gly Lys Ser Asp Lys Ser Gly Glu Leu Val Thr Ala
        370                 375                 380

Ile Gly Thr His Tyr Gln Thr Leu Ser Thr Gln Asn Pro Ser Asn Ile
385                 390                 395                 400

Lys Ile Leu Asn Asn His Phe Asp Asn Met Met Tyr Ala Gly Val Arg
                405                 410                 415

Phe Thr Gly Phe Thr Asp Val Leu Ile Lys Gly Asn Arg Phe Asp Lys
                420                 425                 430

Lys Val Lys Gly Glu Ser Val His Tyr Arg Glu Ser Gly Ala Ala Leu
            435                 440                 445

Val Asn Ala Tyr Ser Tyr Lys Asn Thr Lys Asp Leu Leu Asp Leu Asn
        450                 455                 460

Lys Gln Val Val Ile Ala Glu Asn Ile Phe Asn Ile Ala Asp Pro Lys
465                 470                 475                 480

Thr Lys Ala Ile Arg Val Ala Lys Asp Ser Ala Glu Tyr Leu Gly Lys
                485                 490                 495

Val Ser Asp Ile Thr Val Thr Lys Asn Val Ile Asn Asn Ser Lys
                500                 505                 510

Glu Thr Glu Gln Pro Asn Ile Glu Leu Leu Arg Val Ser Asp Asn Leu
            515                 520                 525

Val Val Ser Glu Asn Ser Ile Phe Gly Gly Lys Glu Gly Ile Val Ile
        530                 535                 540

Glu Asp Ser Lys Gly Lys Ile Thr Val Leu Asn Asn Gln Phe Tyr Asn
545                 550                 555                 560

Leu Ser Gly Lys Tyr Ile Ser Phe Ile Lys Ser Asn Ala Asn Gly Lys
                565                 570                 575

Glu Pro Val Ile Arg Asp Ser Asp Gly Asn Phe Asn Ile Val Thr Glu
            580                 585                 590

Asn Gly Leu Tyr Lys Ile Val Thr Asn Asn Leu Ser Asp Lys Asn Glu
        595                 600                 605
```

```
Lys Glu Lys Asn Lys Glu Glu Lys Gln Ser Asn Ser Asn Asn Val Ile
            610                 615                 620

Asp Ser Asn Gln Lys Asn Gly Glu Phe Asn Ser Ser Lys Asp Asn Arg
625                 630                 635                 640

Gln Met Asn Asp Lys Ile Asp Asn Lys Gln Asp Asn Lys Thr Glu Glu
            645                 650                 655

Val Asn Tyr Lys Ile Val Gly Asp Gly Arg Glu Thr Glu Asn His Ile
            660                 665                 670

Asn Lys Ser Lys Glu Ile Val Asp Val Lys Gln Lys Leu Pro Lys Thr
            675                 680                 685

Gly Ser Asn Lys Ile Met Glu Leu Phe Leu Thr Val Thr Gly Ile Gly
            690                 695                 700

Leu Leu Leu Thr Leu Lys Gly Leu Lys Tyr Tyr Gly Lys Asp Lys
705                 710                 715

<210> SEQ ID NO 33
<211> LENGTH: 913
<212> TYPE: PRT
<213> ORGANISM: Moraxella catarrhalis

<400> SEQUENCE: 33

Met Asn Lys Ile Tyr Lys Val Lys Lys Asn Ala Ala Gly His Leu Val
1               5                   10                  15

Ala Cys Ser Glu Phe Ala Lys Gly His Thr Lys Lys Ala Val Leu Gly
            20                  25                  30

Ser Leu Leu Ile Val Gly Ile Leu Gly Met Ala Thr Thr Ala Ser Ala
            35                  40                  45

Gln Ala Ile Asn Thr Gly Gln Gly Thr Val Val Asp Gln Asn Gly Asn
50                  55                  60

Glu Ala Ile Gly Asn Tyr Ser Thr Ala Ser Gly Gly Asp Tyr Asn Gln
65                  70                  75                  80

Ala Lys Gly Asn Tyr Ser Thr Ala Ser Gly Gly Ser Gly Asn Thr Ala
            85                  90                  95

Glu Gly Asn Tyr Ser Thr Ala Ser Gly Gly Leu Gly Asn Thr Ala Glu
            100                 105                 110

Gly Asn Tyr Ser Thr Ala Ser Gly Gly Leu Gly Asn Thr Ala Lys Gly
            115                 120                 125

Lys Tyr Ser Thr Val Ala Gly Gly Ala Asn Asn Gln Ala Lys Gly Asp
            130                 135                 140

Tyr Ser Thr Ala Ser Gly Gly Ser Gly Asn Thr Ala Glu Gly Asn Tyr
145                 150                 155                 160

Ser Thr Val Ala Gly Gly Lys Asn Asn Gln Ala Thr Gly Leu Asn Ser
            165                 170                 175

Thr Val Ala Gly Gly Ser Asp Asn Gln Ala Thr Gly Thr Gly Ser Phe
            180                 185                 190

Ala Ala Gly Val Gly Asn Lys Ala Asn Ala Glu Asn Ala Val Ala Leu
            195                 200                 205

Gly Asn Lys Asn Thr Ile Glu Gly Glu Asn Ser Val Ala Ile Gly Ser
            210                 215                 220

Asn Asn Thr Val Glu Thr Gly Lys Glu Asn Val Phe Ile Leu Gly Ser
225                 230                 235                 240

Gly Thr Thr Gly Val Thr Ser Asn Ser Val Leu Leu Gly Asn Lys Thr
            245                 250                 255

Ala Gly Lys Glu Ala Thr Ala Val Asn Asp Ala Thr Val Asn Gly Leu
            260                 265                 270
```

```
Thr Leu Lys Asn Phe Ala Gly Val Ser Lys Thr Gly Asn Gly Thr Val
        275                 280                 285

Ser Val Gly Ser Glu Asn His Glu Arg Gln Ile Val Asn Val Gly Ala
290                 295                 300

Gly Lys Ile Ser Ala Asp Ser Thr Asp Ala Val Asn Gly Ser Gln Leu
305                 310                 315                 320

His Ala Leu Ala Thr Val Val Ala Lys Asn Lys Ser Asp Ile Thr Lys
                325                 330                 335

Asn Gln Ala Glu Thr Leu Val Asn Arg Val Asn Ile Lys Glu Leu Glu
            340                 345                 350

Arg Lys Gln Glu Asn Asp Ile Lys Glu Val Val Glu Met Gln Asn Ala
        355                 360                 365

Ile Ala Glu Gln Ala Asp Lys Asn Lys Asn His Ile Gln Asp Leu Ala
370                 375                 380

Lys Ala Gln Leu Ala Gly Val Thr Val Met Glu Glu Leu Asn Lys His
385                 390                 395                 400

Val Glu Asp Leu Tyr Glu Ala Thr Asn Asp Asn Leu Asp Lys Ile Ser
                405                 410                 415

Gln Leu Asp Gly Ala Val Phe Asn Asn Thr Gln Asn Ile Ala Lys Asn
            420                 425                 430

Ser Asn His Ile Lys Thr Leu Glu Asn Asn Val Glu Glu Glu Leu Leu
        435                 440                 445

Asn Leu Ser Gly Arg Leu Leu Asp Gln Lys Ala Asp Ile Asp Asn Asn
450                 455                 460

Ile Asn Asn Ile Tyr Glu Leu Ala Gln Gln Asp Gln His Ser Ser
465                 470                 475                 480

Asp Ile Lys Thr Leu Lys Asn Asn Val Glu Glu Gly Leu Leu Asp Leu
                485                 490                 495

Ser Gly Arg Leu Ile Asp Gln Lys Ala Asp Leu Thr Lys Asp Ile Lys
            500                 505                 510

Ala Leu Glu Asn Asn Val Glu Glu Gly Leu Leu Asp Leu Ser Gly Arg
        515                 520                 525

Leu Ile Asp Gln Lys Ala Asp Ile Ala Lys Asn Gln Ala Asp Ile Ala
530                 535                 540

Gln Asn Gln Thr Asp Ile Gln Asp Leu Ala Ala Tyr Asn Glu Leu Gln
545                 550                 555                 560

Asp Ala Tyr Ala Lys Gln Gln Thr Glu Ala Ile Asp Ala Leu Asn Lys
                565                 570                 575

Ala Ser Ser Ala Asn Thr Asp Arg Ile Ala Thr Ala Glu Leu Gly Ile
            580                 585                 590

Ala Glu Asn Lys Lys Asp Ala Gln Ile Ala Lys Ala Gln Ala Asn Glu
        595                 600                 605

Asn Lys Asp Gly Ile Ala Lys Asn Gln Ala Asp Ile Gln Leu His Asp
610                 615                 620

Lys Lys Ile Thr Asn Leu Gly Ile Leu His Ser Met Val Ala Arg Ala
625                 630                 635                 640

Val Gly Asn Asn Thr Gln Gly Val Ala Thr Asn Lys Ala Asp Ile Ala
                645                 650                 655

Lys Asn Gln Ala Asp Ile Ala Asn Asn Ile Lys Asn Ile Tyr Glu Leu
            660                 665                 670

Ala Gln Gln Gln Asp Gln His Ser Ser Asp Ile Lys Thr Leu Ala Lys
        675                 680                 685
```

Val Ser Ala Ala Asn Thr Asp Arg Ile Ala Lys Asn Lys Ala Glu Ala
690 695 700

Asp Ala Ser Phe Glu Thr Leu Thr Lys Asn Gln Asn Thr Leu Ile Glu
705 710 715 720

Gln Gly Glu Ala Leu Val Glu Gln Asn Lys Ala Ile Asn Gln Glu Leu
725 730 735

Glu Gly Phe Ala Ala His Ala Asp Val Gln Asp Lys Gln Ile Leu Gln
740 745 750

Asn Gln Ala Asp Ile Thr Thr Asn Lys Thr Ala Ile Glu Gln Asn Ile
755 760 765

Asn Arg Thr Val Ala Asn Gly Phe Glu Ile Glu Lys Asn Lys Ala Gly
770 775 780

Ile Ala Thr Asn Lys Gln Glu Leu Ile Leu Gln Asn Asp Arg Leu Asn
785 790 795 800

Arg Ile Asn Glu Thr Asn Asn Arg Gln Asp Gln Lys Ile Asp Gln Leu
805 810 815

Gly Tyr Ala Leu Lys Glu Gln Gly Gln His Phe Asn Asn Arg Ile Ser
820 825 830

Ala Val Glu Arg Gln Thr Ala Gly Gly Ile Ala Asn Ala Ile Ala Ile
835 840 845

Ala Thr Leu Pro Ser Pro Ser Arg Ala Gly Glu His His Val Leu Phe
850 855 860

Gly Ser Gly Tyr His Asn Gly Gln Ala Ala Val Ser Leu Gly Ala Ala
865 870 875 880

Gly Leu Ser Asp Thr Gly Lys Ser Thr Tyr Lys Ile Gly Leu Ser Trp
885 890 895

Ser Asp Ala Gly Gly Leu Ser Gly Gly Val Gly Gly Ser Tyr Arg Trp
900 905 910

Lys

<210> SEQ ID NO 34
<211> LENGTH: 272
<212> TYPE: PRT
<213> ORGANISM: Neisseria meningitidis

<400> SEQUENCE: 34

Met Lys Lys Thr Val Phe Thr Cys Ala Met Ile Ala Leu Thr Gly Thr
1 5 10 15

Ala Ala Ala Ala Gln Glu Leu Gln Thr Ala Asn Glu Phe Thr Val His
20 25 30

Thr Asp Leu Ser Ser Ile Ser Ser Thr Arg Ala Phe Leu Lys Glu Lys
35 40 45

His Lys Ala Ala Lys His Ile Gly Val Arg Ala Asp Ile Pro Phe Asp
50 55 60

Ala Asn Gln Gly Ile Arg Leu Glu Ala Gly Phe Gly Arg Ser Lys Lys
65 70 75 80

Asn Ile Ile Asn Leu Glu Thr Asp Glu Asn Lys Leu Gly Lys Thr Lys
85 90 95

Asn Val Lys Leu Pro Thr Gly Val Pro Glu Asn Arg Ile Asp Leu Tyr
100 105 110

Thr Gly Tyr Thr Tyr Thr Gln Thr Leu Ser Asp Ser Leu Asn Phe Arg
115 120 125

Val Gly Ala Gly Leu Gly Phe Glu Ser Ser Lys Asp Ser Ile Lys Thr
130 135 140

```
Thr Lys His Thr Leu His Ser Ser Arg Gln Ser Trp Leu Ala Lys Val
145                 150                 155                 160

His Ala Asp Leu Leu Ser Gln Leu Gly Asn Gly Trp Tyr Ile Asn Pro
                165                 170                 175

Trp Ser Glu Val Lys Phe Asp Leu Asn Ser Arg Tyr Lys Leu Asn Thr
            180                 185                 190

Gly Val Thr Asn Leu Lys Lys Asp Ile Asn Gln Lys Thr Asn Gly Trp
        195                 200                 205

Gly Phe Gly Leu Gly Ala Asn Ile Gly Lys Lys Leu Gly Glu Ser Ala
    210                 215                 220

Ser Ile Glu Ala Gly Pro Phe Tyr Lys Gln Arg Thr Tyr Lys Glu Ser
225                 230                 235                 240

Gly Glu Phe Ser Val Thr Thr Lys Ser Gly Asp Val Ser Leu Thr Ile
                245                 250                 255

Pro Lys Thr Ser Ile Arg Glu Tyr Gly Leu Arg Val Gly Ile Lys Phe
            260                 265                 270

<210> SEQ ID NO 35
<211> LENGTH: 129
<212> TYPE: PRT
<213> ORGANISM: Fusobacterium nucleatum

<400> SEQUENCE: 35

Met Lys Lys Phe Leu Leu Leu Ala Val Leu Val Val Ser Ala Ser Ala
1               5                   10                  15

Phe Ala Ala Asn Asp Ala Ala Ser Leu Val Gly Glu Leu Gln Ala Leu
                20                  25                  30

Asp Ala Glu Tyr Gln Asn Leu Ala Asn Gln Glu Ala Arg Phe Asn
            35                  40                  45

Glu Glu Lys Ala Gln Ala Asp Ala Ala Lys Gln Ala Leu Ala Gln Asn
    50                  55                  60

Glu Gln Val Tyr Asn Glu Leu Ser Gln Arg Ala Gln Arg Leu Gln Ala
65                  70                  75                  80

Glu Ala Asn Thr Arg Phe Tyr Lys Ser Gln Tyr Gln Asp Leu Ala Ser
                85                  90                  95

Lys Tyr Glu Asp Ala Leu Lys Lys Leu Glu Ala Glu Met Glu Gln Gln
            100                 105                 110

Lys Gly Val Ile Ser Asp Phe Glu Lys Ile Gln Ala Leu Arg Ala Gly
        115                 120                 125

Asn

<210> SEQ ID NO 36
<211> LENGTH: 300
<212> TYPE: PRT
<213> ORGANISM: Escherichia coli

<400> SEQUENCE: 36

Met Lys Arg Val Ile Thr Leu Phe Ala Val Leu Leu Met Gly Trp Ser
1               5                   10                  15

Val Asn Ala Trp Ser Phe Ala Cys Lys Thr Ala Asn Gly Thr Ala Ile
                20                  25                  30

Pro Ile Gly Gly Gly Ser Ala Asn Val Tyr Val Asn Leu Ala Pro Val
            35                  40                  45

Val Asn Val Gly Gln Asn Leu Val Val Asp Leu Ser Thr Gln Ile Phe
    50                  55                  60
```

```
Cys His Asn Asp Tyr Pro Glu Thr Ile Thr Asp Tyr Val Thr Leu Gln
 65                  70                  75                  80

Arg Gly Ser Ala Tyr Gly Gly Val Leu Ser Asn Phe Ser Gly Thr Val
                 85                  90                  95

Lys Tyr Ser Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
            115                 120                 125

Tyr Leu Thr Pro Val Ser Ser Ala Gly Gly Val Ala Ile Lys Ala Gly
        130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
            180                 185                 190

Leu Pro Asp Tyr Pro Gly Ser Val Pro Ile Pro Leu Thr Val Tyr Cys
        195                 200                 205

Ala Lys Ser Gln Asn Leu Gly Tyr Tyr Leu Ser Gly Thr Thr Ala Asp
210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                245                 250                 255

Asn Thr Val Ser Leu Gly Ala Val Gly Thr Ser Ala Val Ser Leu Gly
            260                 265                 270

Leu Thr Ala Asn Tyr Ala Arg Thr Gly Gly Gln Val Thr Ala Gly Asn
        275                 280                 285

Val Gln Ser Ile Ile Gly Val Thr Phe Val Tyr Gln
    290                 295                 300

<210> SEQ ID NO 37
<211> LENGTH: 321
<212> TYPE: PRT
<213> ORGANISM: Klebsiella pneumoniae

<400> SEQUENCE: 37

Met Lys Lys Leu Thr Leu Phe Ile Gly Leu Met Ala Leu Gly Thr Thr
  1               5                  10                  15

Ser Ala Trp Ala Ser Cys Trp Gln Ser Asn Ser Ala Tyr Glu Ile Asn
                 20                  25                  30

Met Ala Met Gly Arg Val Val Ser Pro Asp Leu Pro Val Gly Ser
             35                  40                  45

Val Ile Ala Thr Lys Thr Trp Thr Met Pro Asp Asn Asn Thr Ile Tyr
         50                  55                  60

Val Thr Cys Asp Arg Asn Thr Thr Leu Lys Ser Asp Ala Lys Val Val
 65                  70                  75                  80

Ala Ala Gly Leu Val Gln Gly Ala Asn Lys Val Tyr Ser Thr Ala Ile
                 85                  90                  95

Pro Gly Ile Gly Leu Arg Phe Ser Arg Lys Gly Ala Ile Ser Met Ile
            100                 105                 110

Tyr Pro Asp Ser Tyr Thr Thr Thr Gly Ser Ser Phe Arg Leu Val Gly
            115                 120                 125
```

```
Ser Thr Phe Thr Leu Asp Ile Ile Lys Thr Ser Thr Thr Gly Ser
    130                 135                 140

Gly Thr Leu Ala Ser Gly Pro Tyr Thr Glu Tyr Gly Pro Gly Phe Thr
145                 150                 155                 160

Ile Leu Lys Thr Ser Leu Asn Ala Asp Ala Ile Thr Ile Val Ser Pro
                165                 170                 175

Ser Cys Thr Ile Leu Gly Gly Lys Asn Met Asn Val Asp Ile Gly Thr
                180                 185                 190

Ile Lys Arg Ala Asp Leu Lys Gly Val Gly Thr Trp Ala Gly Gly Thr
            195                 200                 205

Pro Phe Asp Ile Lys Leu Glu Cys Ser Gly Gly Val Ser Val Ser Gly
            210                 215                 220

Tyr Ala Asn Ile Asn Thr Ser Phe Ser Gly Thr Leu Ala Thr Asn Thr
225                 230                 235                 240

Ser Ala Asn Gln Gly Val Leu Leu Asn Glu Lys Thr Gly Asn Ser Ala
                245                 250                 255

Ala Lys Gly Val Gly Val Gln Val Ile Lys Asp Asn Thr Pro Leu Glu
                260                 265                 270

Phe Asn Lys Lys His Asn Ile Gly Thr Leu Gln Ser Gln Glu Thr Arg
            275                 280                 285

Tyr Ile Thr Leu Pro Leu His Ala Arg Phe Tyr Gln Tyr Ala Pro Thr
            290                 295                 300

Thr Ser Thr Gly Glu Val Glu Ser His Leu Val Phe Asn Leu Thr Tyr
305                 310                 315                 320

Asp

<210> SEQ ID NO 38
<211> LENGTH: 151
<212> TYPE: PRT
<213> ORGANISM: Escherichia coli

<400> SEQUENCE: 38

Met Lys Leu Leu Lys Val Ala Ala Ile Ala Ala Ile Val Phe Ser Gly
1               5                   10                  15

Ser Ala Leu Ala Gly Val Val Pro Gln Tyr Gly Gly Gly Asn His
                20                  25                  30

Gly Gly Gly Gly Asn Asn Ser Gly Pro Asn Ser Glu Leu Asn Ile Tyr
            35                  40                  45

Gln Tyr Gly Gly Gly Asn Ser Ala Leu Ala Leu Gln Thr Asp Ala Arg
        50                  55                  60

Asn Ser Asp Leu Thr Ile Thr Gln His Gly Gly Gly Asn Gly Ala Asp
65                  70                  75                  80

Val Gly Gln Gly Ser Asp Asp Ser Ser Ile Asp Leu Thr Gln Arg Gly
                85                  90                  95

Phe Gly Asn Ser Ala Thr Leu Asp Gln Trp Asn Gly Lys Asn Ser Glu
            100                 105                 110

Met Thr Val Lys Gln Phe Gly Gly Gly Asn Gly Ala Ala Val Asp Gln
        115                 120                 125

Thr Ala Ser Asn Ser Ser Val Asn Val Thr Gln Val Gly Phe Gly Asn
    130                 135                 140

Asn Ala Thr Ala His Gln Tyr
145                 150

<210> SEQ ID NO 39
```

<211> LENGTH: 341
<212> TYPE: PRT
<213> ORGANISM: Agrobacterium radiobacter
<220> FEATURE:
<221> NAME/KEY: Xaa is carboxylated lysine
<222> LOCATION: (145)..(145)

<400> SEQUENCE: 39

```
Met Ser Met Ala Arg Pro Ile Gly Thr Gly Asp Leu Ile Asn Thr Val
1               5                   10                  15

Arg Gly Pro Ile Pro Val Ser Glu Ala Gly Phe Thr Leu Thr His Glu
            20                  25                  30

His Ile Cys Gly Ser Ser Ala Gly Phe Leu Arg Ala Trp Pro Glu Phe
        35                  40                  45

Phe Gly Ser Arg Lys Ala Leu Val Glu Lys Ala Val Arg Gly Leu Arg
50                  55                  60

His Ala Arg Ala Ala Gly Val Gln Thr Ile Val Asp Val Ser Thr Phe
65                  70                  75                  80

Asp Ile Gly Arg Asp Val Arg Leu Leu Ala Glu Val Ser Arg Ala Ala
                85                  90                  95

Asp Val His Ile Val Ala Ala Thr Gly Leu Trp Phe Asp Pro Pro Leu
            100                 105                 110

Ser Met Arg Met Arg Ser Val Glu Glu Leu Thr Gln Phe Phe Leu Arg
        115                 120                 125

Glu Ile Gln His Gly Ile Glu Asp Thr Gly Ile Arg Ala Gly Ile Ile
130                 135                 140

Xaa Val Ala Thr Thr Gly Lys Ala Thr Pro Phe Gln Glu Leu Val Leu
145                 150                 155                 160

Arg Ala Ala Ala Arg Ala Ser Leu Ala Thr Gly Val Pro Val Thr Thr
                165                 170                 175

His Thr Ser Ala Ser Gln Arg Asp Gly Glu Gln Gln Ala Ala Ile Phe
            180                 185                 190

Glu Ser Glu Gly Leu Ser Pro Ser Arg Val Cys Ile Gly His Ser Asp
        195                 200                 205

Asp Thr Asp Asp Leu Ser Tyr Leu Thr Gly Leu Ala Ala Arg Gly Tyr
210                 215                 220

Leu Val Gly Leu Asp Arg Met Pro Tyr Ser Ala Ile Gly Leu Glu Gly
225                 230                 235                 240

Asn Ala Ser Ala Leu Ala Leu Phe Gly Thr Arg Ser Trp Gln Thr Arg
                245                 250                 255

Ala Leu Leu Ile Lys Ala Leu Ile Asp Arg Gly Tyr Lys Asp Arg Ile
            260                 265                 270

Leu Val Ser His Asp Trp Leu Phe Gly Phe Ser Ser Tyr Val Thr Asn
        275                 280                 285

Ile Met Asp Val Met Asp Arg Ile Asn Pro Asp Gly Met Ala Phe Val
290                 295                 300

Pro Leu Arg Val Ile Pro Phe Leu Arg Glu Lys Gly Val Pro Pro Glu
305                 310                 315                 320

Thr Leu Ala Gly Val Thr Val Ala Asn Pro Ala Arg Phe Leu Ser Pro
                325                 330                 335

Thr Val Arg Ala Ser
            340
```

<210> SEQ ID NO 40
<211> LENGTH: 347
<212> TYPE: PRT

```
<213> ORGANISM: Artificial Sequence
<220> FEATURE:
<223> OTHER INFORMATION: Supercharged protein
<220> FEATURE:
<221> NAME/KEY: Xaa is carboxylated lysine
<222> LOCATION: (151)..(151)

<400> SEQUENCE: 40
```

| | | | | | | | | | | | | | | |
|---|---|---|---|---|---|---|---|---|---|---|---|---|---|---|
| Met | His | His | His | His | His | Ser | Met | Ala | Arg | Pro | Ile | Gly | Thr | Gly |
| 1 | | | | 5 | | | | | 10 | | | | | 15 |
| Asp | Leu | Ile | Asn | Thr | Val | Arg | Gly | Pro | Ile | Pro | Val | Ser | Glu | Ala | Gly |
| | | | | 20 | | | | | 25 | | | | | 30 | |
| Phe | Thr | Leu | Thr | His | Glu | His | Ile | Cys | Gly | Ser | Ser | Ala | Gly | Phe | Leu |
| | | | 35 | | | | | 40 | | | | | 45 | | |
| Arg | Ala | Trp | Pro | Glu | Phe | Phe | Gly | Ser | Arg | Lys | Ala | Leu | Val | Glu | Lys |
| 50 | | | | | 55 | | | | | 60 | | | | | |
| Ala | Val | Arg | Gly | Leu | Arg | His | Ala | Arg | Ala | Gly | Val | Gln | Thr | Ile |
| 65 | | | | | 70 | | | | | 75 | | | | | 80 |
| Val | Lys | Val | Ser | Thr | Phe | Asp | Ile | Gly | Arg | Asp | Val | Arg | Leu | Leu | Ala |
| | | | | 85 | | | | | 90 | | | | | 95 | |
| Glu | Val | Ser | Arg | Ala | Ala | Lys | Val | His | Ile | Val | Ala | Ala | Thr | Gly | Leu |
| | | | | 100 | | | | | 105 | | | | | 110 | |
| Trp | Phe | Lys | Pro | Pro | Leu | Ser | Met | Arg | Met | Arg | Ser | Val | Lys | Lys | Leu |
| | | | 115 | | | | | 120 | | | | | 125 | | |
| Thr | Gln | Phe | Phe | Leu | Arg | Glu | Ile | Gln | His | Gly | Ile | Lys | Lys | Thr | Gly |
| | | 130 | | | | | 135 | | | | | 140 | | | |
| Ile | Arg | Ala | Gly | Ile | Ile | Xaa | Val | Ala | Thr | Thr | Gly | Lys | Ala | Thr | Pro |
| 145 | | | | | 150 | | | | | 155 | | | | | 160 |
| Phe | Gln | Glu | Leu | Val | Leu | Arg | Ala | Ala | Arg | Ala | Ser | Leu | Ala | Thr |
| | | | | 165 | | | | | 170 | | | | | 175 | |
| Gly | Val | Pro | Val | Thr | Thr | His | Thr | Ser | Ala | Ser | Gln | Arg | Lys | Gly | Glu |
| | | | 180 | | | | | 185 | | | | | 190 | | |
| Gln | Gln | Ala | Ala | Ile | Phe | Glu | Ser | Glu | Gly | Leu | Ser | Pro | Ser | Arg | Val |
| | | 195 | | | | | 200 | | | | | 205 | | | |
| Cys | Ile | Gly | His | Ser | Asp | Asp | Thr | Lys | Lys | Leu | Ser | Tyr | Leu | Thr | Gly |
| 210 | | | | | 215 | | | | | 220 | | | | | |
| Leu | Ala | Ala | Arg | Gly | Tyr | Leu | Val | Gly | Leu | Asp | Arg | Met | Pro | Tyr | Ser |
| 225 | | | | | 230 | | | | | 235 | | | | | 240 |
| Ala | Ile | Gly | Leu | Lys | Gly | Asn | Ala | Ser | Ala | Leu | Ala | Leu | Phe | Gly | Thr |
| | | | | 245 | | | | | 250 | | | | | 255 | |
| Arg | Ser | Trp | Gln | Thr | Arg | Ala | Leu | Leu | Ile | Lys | Ala | Leu | Ile | Asp | Arg |
| | | | 260 | | | | | 265 | | | | | 270 | | |
| Gly | Tyr | Lys | Asp | Arg | Ile | Leu | Val | Ser | His | Asp | Trp | Leu | Phe | Gly | Phe |
| | | 275 | | | | | 280 | | | | | 285 | | | |
| Ser | Ser | Tyr | Val | Thr | Asn | Ile | Met | Asp | Val | Met | Asp | Arg | Ile | Asn | Pro |
| | 290 | | | | | 295 | | | | | 300 | | | | |
| Asp | Gly | Met | Ala | Phe | Val | Pro | Leu | Arg | Val | Ile | Pro | Phe | Leu | Arg | Glu |
| 305 | | | | | 310 | | | | | 315 | | | | | 320 |
| Lys | Gly | Val | Pro | Pro | Glu | Thr | Leu | Ala | Gly | Val | Thr | Val | Ala | Asn | Pro |
| | | | | 325 | | | | | 330 | | | | | 335 | |
| Ala | Arg | Phe | Leu | Ser | Pro | Thr | Val | Arg | Ala | Ser |
| | | | 340 | | | | | 345 | | |

PROTEIN DELIVERY TO MEMBRANES

TECHNICAL FIELD

The invention relates to novel methods of positioning a protein such as an active enzyme into a phospholipid structure such as a cell membrane. It also relates to structures arising from the method and uses of such structures.

BACKGROUND

It is often desirable in many areas of cell biology to "label" a cell with a protein or other moiety at the cell surface. There are a number of systems available to achieve this, such as labelling with biotin or streptavidin, or with gold particles, or with Green Fluorescent Protein (GFP). Integral membrane proteins can also be a useful target for labelling processes.

For example, Armstrong et al. (Nat. Commun. (2015) Jun. 17; 6:7405) described a method of functionalising human mesenchymal stem cells (hMSCs) by polymer-surfactant conjugation of proteins, which enabled delivery of functional proteins to the hMSC membrane. This built on previous work which provided protein-polymer surfactant conjugates (PPSCs) in which surfactant molecules were conjugated to the surface of proteins via electrostatic interactions, either directly (Matsuura et al. (1993) *J. Am. Chem. Soc.* vol. 155, 1261-1264), or by way of cationisation of the protein surface by N-(3-dimethylaminopropyl)-N'-ethylcarbodiimide (EDC)-mediated coupling of N,N'-dimethyl-1,3-propanediamine (DMPA) groups to solvent-accessible acidic amino acid side chains (Perriman et al. (2010) *Nature Chem.* vol. 2, 622-626; Brogan et al. (2013) *J. Phys. Chem. B* vol. 117, 8400-8407; Sharma et al. (2013) *Adv. Mater.* vol. 25, 2005-2010). This enabled workers to alter the solubility of proteins in water and organic solvent (Matsuura et al. (1993) *J. Am. Chem. Soc.* vol. 155, 1261-1264), or to provide proteins in liquid form (as opposed to being in solution; see, for example, Perriman et al. (2010) *Nature Chem.* vol. 2, 622-626), or proteins which form a self-standing film (Sharma et al. (2013) *Adv. Mater.* vol. 25, 2005-2010).

The present invention described here provides alternative methods for localisation of specific proteins, for the first time including functional enzymes, onto a phospholipid bilayer, such as a cell membrane or the membrane of a liposome.

SUMMARY OF THE INVENTION

According to a first aspect of the invention, there is provided a phospholipid composition which is a phospholipid bilayer or micelle comprising at least one embedded protein-polymer surfactant conjugate, the conjugate comprising an anchor protein, the composition characterised in that the anchor protein is a cationised protein or an anionised protein and is (a) an active enzyme and/or (b) is a protein which does not comprise a —$CH_2C(O)NCH_3(CH_2)_3N(CH_3)_2H^+$ linker covalently bonded to an amino acid side chain, for example, to an acidic amino acid side chain.

The compositions and methods disclosed herein are applicable to a wide range of cell types including stem cells, lymphocytes and vesicles (including exosomes) and to a very broad range of proteins. The result is a platform with potential in a wide range of clinical and non-clinical applications requiring the targeted delivery of cells to specific locations. Several areas of unmet clinical need can be addressed by use of the invention, for example provision of stem cells for cardiac therapy, cell-based wound glues and organophosphate poisoning treatment.

The presence or absence in a protein of a linker such as that described above (i.e., a —$CH_2C(O)NCH_3(CH_2)_3N(CH_3)_2H^+$ linker), covalently bonded to an amino acid side chain, is readily determined by the skilled person, for example by proteomics methods (such as tryptic digestion followed by mass spectrometry) to determine the amino acid composition of the protein, and therefore to find any unnatural groups such as a linker as described above (for example, amino acid residues modified by DMPA as described elsewhere herein).

The terms "cationised protein" or "anionised protein" indicate that the anchor protein is an electrostatically modified protein. This is a protein which differs from its native state (i.e., from the state of the wild-type version of the protein) in that it has a different surface charge distribution compared to the native (or "unmodified" or "wild-type") protein. Typically, this surface charge distribution is assessed at physiological pH, for example at about pH 6-9, for example about pH 6, 6.5, 7, 7.5, 8, 8.5 or about 9. The native protein may be referred to herein as an "anchor precursor protein". The electrostatic modification differences between the anchor protein and the anchor precursor protein (such as the addition of diamine groups, in some embodiments), as described herein, are present regardless of the pH of the protein environment (e.g., the protein solution). The electrostatic modification may, for example, be achieved by cationisation of an anchor precursor protein, or by anionisation of an anchor precursor protein, or by recombinant expression of a protein having a more positive or a more negative overall charge compared to an anchor precursor protein, for example at physiological pH as described above. The resulting protein may be referred to as a cationised protein in the case of modification to have an overall increased surface positive charge, or as an anionised protein in the case of modification to have an overall increased surface negative charge. Therefore, the anchor protein is not a naturally occurring, or wild-type, protein, for example as determined at physiological pH. For a cationised protein the overall change in surface positive charge may be +1 to +100, for example, +1 to +80, +10 to +70, +20 to +60, or +30 to +50, such as about +5, +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39, +40, +41, +42, +43, +44, +45, +46, +47, +48, +49, +50, +51, +52, +53, +54, or +55. For an anionised protein the overall change in surface negative charge may be −1 to −100, for example, −1 to −80, −10 to −70, −20 to −60, or −30 to −50, such as about −5, −6, −7, −8, −9, −10, −11, −12, −13, −14, −15, −16, −17, −18, −19, −20, −21, −22, −23, −24, −25, −26, −27, −28, −29, −30, −31, −32, −33, −34, −35, −36, −37, −38, −39, −40, −41, −42, −43, −44, −45, −46, −47, −48, −49, −50, −51, −52, −53, −54 or −55.

The name of a particular protein may be used herein to refer interchangeably to an anchor protein or to the anchor protein precursor. For example, the composition may comprise an electrostatically modified thrombin, in which case the term "thrombin" may be used to refer either to the anchor protein or to the anchor precursor protein. Alternatively, a cationised anchor protein may be referred to herein with a "c" prefix, for example, "cThrombin" for cationised thrombin. A recombinantly prepared supercharged protein (as described further below) may be referred to herein with a "sc" prefix, for example, "scOpdA" for supercharged OpdA.

An anchor precursor protein, therefore, as used throughout this specification, is a protein which is modifiable or modified to provide an anchor protein. For example, an anchor precursor protein may be submitted to a chemical method of electrostatic modification, as described elsewhere herein, or is a protein which may be used as a base or starting point for rational design of a modified protein, having an overall charge modified compared to the precursor protein, the modified protein being expressed and obtained using recombinant DNA technology. An anchor precursor protein may, therefore, be a naturally occurring or wild-type protein at physiological pH.

When the anchor protein is an enzyme, it is an active enzyme, i.e. an enzyme which retains the ability to catalyse the reaction catalysed by the anchor precursor protein. For example, the enzyme activity of the anchor protein (being a cationised or anionised anchor precursor protein) may be at least about 75% of the activity of the anchor precursor protein enzyme, for example, at least about 80%, 85%, 90%, 91%, 92%, 93%, 94%, 95%, 96%, 97%, 98% or at least about 99% the activity of the anchor precursor protein enzyme. Enzyme activity may be determined by any routine method relevant to the enzyme concerned, in accordance with the routine ability of the skilled person. In some cases, the enzyme activity of the anchor protein (being a cationised or anionised anchor precursor protein) may increase compared to the activity of the anchor precursor protein, i.e. have an activity of more than 100% of the activity of the anchor precursor protein.

The phospholipid composition according to the invention may take the form of a bilayer structure, which may form part of a vesicle, liposome, cell, artificial cell or cell organelle, or may take the form of a micelle. The phospholipid composition may, therefore, itself be a vesicle, liposome, artificial cell or cell organelle, or may be a micelle. The term "composition" does not require the presence of any components other than the phospholipid bilayer or micelle and the embedded protein-polymer surfactant conjugate, although the phospholipid composition may be present within a wider composition such as a cell, a pharmaceutical composition or a surgical composition as mentioned elsewhere herein.

The term "protein-polymer surfactant conjugate", as used throughout this specification, indicates a discrete construct which comprises a protein (referred to as the "anchor protein") having one or more surfactant molecules electrostatically complexed to a charged amino acid residue at the surface of the protein. As mentioned above, the preparation of similar constructs was described, for example, by Perriman et al. (2010; *Nature Chem*. vol. 2, 622-626), Brogan et al. (2013; *J. Phys. Chem. B* vol. 117, 8400-8407) and Sharma et al. (2013; *Adv. Mater*. vol. 25, 2005-2010). The conjugates are proteins having an amphiphilic surfactant corona, as described herein, around at least a portion of the overall structure. The presence of such a corona may be confirmed by comparison of the conjugate with the corresponding wild-type anchor precursor protein, to detect changes in charge and/or size. Techniques such as mass spectrometry, zeta potentiometry, small angle X-ray scattering and/or dynamic light scattering, particularly a combination of two or more of these, may be employed to detect such changes.

The term "embedded" indicates that the protein-polymer surfactant conjugate is located at least partially within the phospholipid bilayer or layer (in the case of a micelle). That is, the protein-polymer surfactant conjugate at least partially intersects with the phospholipid bilayer or layer, rather than merely interacting with a surface of the phospholipid bilayer or layer. Non-embedding/intersecting surface interaction is described, for example, by Futami et al. (*J. Biosci. Bioeng.* (2005) vol. 99, 95-103) and such electrostatic interactions between a protein and a phospholipid bilayer or layer are not encompassed by the present invention.

A schematic diagram of a phospholipid composition according to the invention which is a bilayer comprising an embedded protein-polymer surfactant conjugate is shown in FIG. 2. A composition according to the invention may be useful to enable the introduction of a wide range of proteins into a wide range of phospholipid bilayer and/or micelle types, such as a cell membrane. Advantageously and surprisingly, the compositions and methods described herein enable the localisation of active enzymes to a cell surface and, thereby, to a tissue or other population of cells.

The anchor protein in the protein-polymer surfactant conjugate may be linked to a secondary molecule which may, for example, also be a protein, or a polypeptide or peptide, or may be one half of a bioconjugation system such as the SpyCatcher/SpyTag system (Reddington & Howarth (2015) *Curr. Op. Chem. Biol*. vol. 29 p 94-99; WO2014/176311), or streptavidin/biotin. The secondary molecule may be a protein which is not a cationised or anionised protein and, although forming part of the overall protein-polymer surfactant conjugate, does not have an amphiphilic surfactant corona. This is because, in the secondary molecule, there is not a sufficiently high surface distribution of charged amino acid side chains to which surfactant molecules may electrostatically complex.

In consequence, in the phospholipid composition, the secondary molecule may be positioned such that it is not embedded with the rest of the protein-polymer surfactant conjugate in the phospholipid bilayer or layer. That is, the secondary molecule may be linked to the anchor protein such that, in the composition, it is positioned to the interior or exterior of a vesicle, liposome, cell, artificial cell, cell organelle, or micelle of which the phospholipid bilayer or layer forms at least a part. A schematic diagram of this arrangement is shown in FIG. 3. Effectively, as a result of being part of the overall protein-polymer surfactant conjugate, the secondary molecule is attached to the interior or exterior surface of a vesicle, liposome, cell, artificial cell, cell organelle, or micelle of which the phospholipid bilayer or layer forms at least a part, via linkage to the anchor protein, which is embedded within the phospholipid bilayer or layer. The anchor protein in each protein-polymer surfactant conjugate may be linked to more than one of the secondary molecules as described. Therefore, the term "protein-polymer surfactant conjugate" may encompass any embodiment in which the anchor protein is linked to one or more secondary molecules.

The protein-polymer surfactant conjugate may comprise, by way of non-limiting example, a labelling protein such as GFP, PsmOrange or magnetoferritin, a protein conjugated to labelling molecule or nanoparticle, an enzymatic protein such as a peroxidase or a phosphotriesterase (such as OpdA from *Agrobacterium radiobacter* (SEQ ID NO:10, also described by SEQ ID NO:39) or a functional variant or portion thereof) or a protease (such as thrombin) or an enzyme precursor protein such as prothrombin (e.g., SEQ ID NO:25 or 26)), an adhesion or "homing" protein such as an antibody, lectin, integrin or adhesion molecule (for example the protein CshA from *Streptococcus gordonii* (SEQ ID NO:20), or a functional variant or portion thereof comprising the fibronectin binding domain of CshA (SEQ ID NO:19), or any of the proteins listed in Table 4), a growth factor (such as PIGF-2 (SEQ ID NO:22) or a functional variant or portion thereof comprising PlGF-2$_{(123-144)}$ (SEQ ID NO:21)), or a carrier protein such as a globin, for example, myoglobin. Depending on the protein, the protein may be cationised or anionised in order to form the anchor protein, or may be the secondary molecule as described above. In addition to the options above, the secondary molecule may be selected from a peptide, polypeptide or other molecule, such as a SpyCatcher or SpyTag motif, biotin or streptavidin.

The term "thrombin" may indicate a thrombin from any species, for example bovine thrombin or human thrombin. The skilled person is readily able to identify suitable thrombin molecules.

The term "surfactant molecule" is well understood by the skilled person, surfactants typically being organic compounds that are amphiphilic, meaning they contain both hydrophobic groups (their tails) and hydrophilic groups (their heads). A cationic surfactant has a positively charged head group, whilst an anionic surfactant has a negatively charged head group. A zwitterionic surfactant is one, such as sodium lauroamphoacetate, which includes both positive and negative charge within the headgroup. The surfactant may additionally comprise functional characteristics such as imaging labels (e.g., a magnetic surfactant (Brown (2013) Adv. Mater. vol. 24, 6244-6247) or a fluorescent surfactant), or features such as oxygen binding capability.

The phospholipid composition may comprise lipids other than phospholipids, for example, cholesterol. It may also comprise other components, such as integral membrane proteins. This may especially be the case where the phospholipid composition is a bilayer forming a cell membrane.

The protein-polymer surfactant conjugate may comprise a polyethylene glycol (PEG)-containing surfactant. For example, the surfactant may have the general structure of Formula I below:

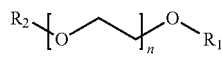

Formula I

In Formula I, n can be any integer including or between 5 and 150, for example any integer including or between 8 and 110. For example, n may be 8, 9, 10, 11, 12, 13, 14, 15, 16, 17, 18, 19, 20, 25, 30, 35, 36, 37, 38, 39, 40, 45, 50, 55, 60, 65, 70, 75, 80, 85, 90, 95, 100, 105 or 110.

R$_1$ may be:

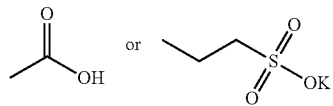

R$_2$ may be C$_x$H$_{(2x+1)}$, where x is any integer including or between 8-18; for example, x=may be 11, 12 or 13. R$_2$ may also be an unsaturated hydrocarbon having 8-18 carbon atoms, for example 11, 12 or 13 carbon atoms. In a further alternative, R$_2$ may be:

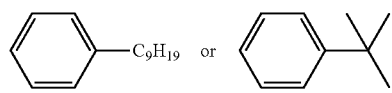

The surfactant may be one of those described herein, such as S621 (Sigma-Aldrich catalogue no. 463221), S907 (Sigma-Aldrich catalogue no. 463256), S1198 (Sigma-Aldrich catalogue no. 473197), or S1783 (oxidised form of glycolic acid ethoxylate 4-nonylphenyl ether, Sigma-Aldrich catalogue no. 238678).

These anionic surfactants have the following structures, as also shown in FIG. 4:

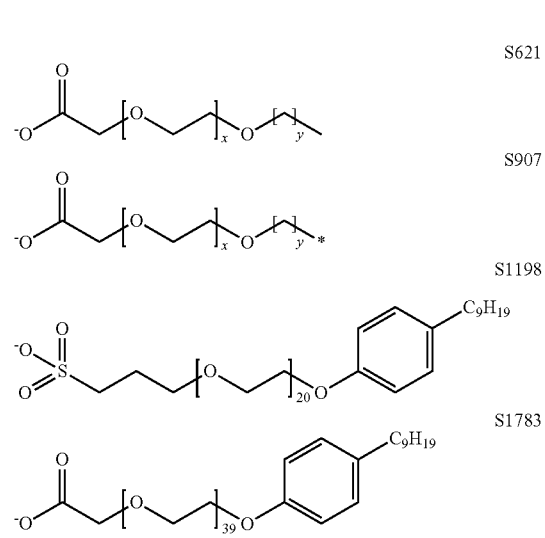

For S621 and S907 x=11-13
For S621, y=7-9
For S907, y=14-15

The molecular weight and polydispersity were measured by mass spectrometry and were found to be as follows:

TABLE 1 molecular weight and polydispersity of surfactants

| Name | MWt | PDi ($Ð_M$) |
|---|---|---|
| S621 | 621 | 1.05 |
| S907 | 907 | 1.06 |
| S1198 | 1198 | 1.03 |
| S1783 | 1783 | 1.12 |

The "polydispersity" reflects the fact that synthetic polymers produced from chemical reactions have a distribution of molecular masses arising from the intrinsically entropic process of polymerisation. The degree of variation is dependent on both the reaction mechanism and the reaction conditions. This degree of variation is defined by the dispersity (Ð), which was until recently known as the "polydispersity". It is defined by the equation:

$$Ð_M = M_w / M_n$$

where $M_w$ is the weight-average molar mass and $M_n$ is the number-average molar mass. The dispersity of a polymer can be estimated using matrix-assisted laser desorption ionization time-of-flight mass spectrometry (MALDI-TOF).

The protein-polymer surfactant conjugate may comprise a surfactant having a molecular weight of at least about 500 Da, for example, at least about 1000, 1100, 1200, 1300, 1400, 1500, 1600, 1700, 1800, 1900, 2000, 2200, 2400, 2600, 2800, 3000, 3200, 3400, 3600, 3800 or at least about 4000 Da.

The protein-polymer surfactant conjugate may comprise a surfactant which is S1783 (i.e., oxidised glycolic acid ethoxylate 4-nonylphenyl ether). Alternatively or additionally, the protein-polymer surfactant conjugate may comprise a cationic surfactant, for example, PEG-15 hydrogenated tallowmodium chloride (sold as Ethoquad® HT25).

The composition according to the invention may comprise a protein-polymer surfactant conjugate which comprises at least two types of surfactant. At least one surfactant may comprise functional characteristics such as imaging labels (e.g., a magnetic surfactant (Brown (2013) Adv. Mater. vol. 24, 6244-6247) or a fluorescent surfactant), or features such as oxygen binding capability.

When the anchor protein is an active enzyme, the cationised protein may be obtained by covalent bonding of a cationic or polycationic linker to an acidic amino acid side chain on the protein. For example, this may be achieved by mixing the protein with N,N'-dimethyl-1,3-propanediamine (DMPA) or an analogue thereof, in the presence of a carbodiimide such as N-(3-dimethylaminopropyl)-N'-ethyl-carbodiimide hydrochloride (EDC) or dicyclohexyl carbodiimide (DCC). The reaction is shown in FIG. 1, which shows that acid residues (numeral (1) in the Figure) are activated towards nucleophilic attack by addition of the zero length cross-linker EDC (2) to form activated o-acylisourea groups (3). The nucleophile DMPA (4) then attacks the activated carbonyl and eliminates isourea to form cationised residues (5). Therefore, the cationised protein may comprise the linker $-CH_2C(O)NCH_3(CH_2)_3N(CH_3)_2H^+$. DMPA or an analogue thereof may be added to the protein prior to mixing with EDC, to ensure the presence of an excess of DMPA or an analogue thereof and thereby avoid cross-linking of proteins to one another.

The step of covalent bonding of a cationic linker to an acidic amino acid side chain on the protein may be carried out in the presence of N-hydroxysuccinimide (NHS) or its water-soluble analogue Sulfo-NHS, to improve the stability of electrostatic coupling.

In the present invention, the mixing of the protein with DMPA or an analogue thereof in the presence of a carbodiimide may be allowed to continue for a limited time so as to avoid protein denaturation and/or aggregation. Such a limited time may be, for example, up to or for about 2 hours, or up to or for about 10, 15, 20, 25, 30, 35, 40, 45, 50, 55, 60, 65, 70, 75, 80, 85 or about 90 minutes. Alternatively or additionally, the product of the mixing with DMPA in the presence of a carbodiimide may be subjected to subsequent size exclusion chromatography, with the product from the chromatography being utilised as the cationised protein. The skilled person is capable of determining the theoretical size of the desired anchor protein, so as to determine the appropriate chromatography eluate to collect, for example by use of a calibrated chromatography column. The inclusion in the method of either or both of these method features ensures that the enzyme is retained in an active state. This was not anticipated in view of prior art methods such as those of Armstrong et al. (Nat. Commun. (2015) Jun. 17; 6:7405) which, if utilised with an enzyme, would destroy its activity. Suitable methods for preparing an anchor protein are outlined in more detail below.

An analogue of DMPA may be N,N'-dimethylhexane-1,6-diamine (DMHA), dimethylethylenediamine (DMEA), 3-dimethylamino propylamine (DMAPA), ethylenediamine (EN), 1,3-diaminopropane (DAP), 1,4-diaminobutane (DAB), 1,5-diaminopropane (DAP), 1,6-diaminohexane (DAH), hexamethylenediamine (HMA), 1,7-diaminheptane (DAH) 1,8-diaminooctane (DAO) and 2-(2-aminoethyl)guanidine (AEG). Other suitable nucleophiles may be contemplated by the skilled person, for example, charged nucleophiles. For example, nucleophiles could also include other primary, secondary and tertiary alkyl diamines and alkyl diamines terminated with a quaternary amine if the opposing terminus contains either a primary, secondary or tertiary amine. Polyalkylamines such as polyethylenimine as either linear chains or branched structures are also contemplated.

Alternatively, the electrostatically modified protein may be obtained by anionisation of the protein. This may be achieved, for example, by nucleophilic addition of dicarboxylic acids (HOOC—R—COOH) to lysine side-chains of the native proteins.

In a further alternative, the electrostatically modified cationised or anionised protein (which does not comprise a $-CH_2C(O)NCH_3(CH_2)_3N(CH_3)_2H^+$ linker covalently bonded to an amino acid side chain) may be obtained by recombinant expression of an anchor protein having an altered charge, i.e., a more positive or a more negative overall charge compared to an anchor precursor protein. Recombinant modification may comprise recombinantly expressing an anchor protein which is a mutant comprising one or more amino acid substitutions within its overall amino acid sequence compared to the sequence of the non-mutant anchor precursor protein, the amino acid substitutions introducing a different surface charge distribution to the anchor protein compared to the anchor precursor protein, by providing a different amino acid charge to the native amino acid at the or each substitution position. Such proteins are known in the art and are referred to as "supercharged" proteins.

For example, an amino acid having an uncharged side group may be replaced by an amino acid having a positively or negatively charged side group (to give an overall charge change of +1 or −1 respectively), or an amino acid having a negatively charged side group may be replaced by an amino acid having a positively charged side group (to give an overall charge change of +2), or an amino acid having a positively charged side group may be replaced by an amino acid having a negatively charged side group (to give an overall charge change of −2), provided that the tertiary structure and/or biological activity of the protein is not significantly altered. This rational design approach may be especially advantageous if the function/activity of the protein depends on the involvement of a particular amino acid, for example one having a charged side group, since the user can direct protein surface charge alterations to non-critical amino acid positions; this may not always be possible with the chemical modification methods described elsewhere herein. The biological activity of the protein in native (anchor precursor protein) or supercharged (anchor protein) form may be determined using an assay appropriate for the protein, as readily selected by the skilled person. For example, thrombin activity may be assessed by contacting with fibrinogen and detecting the rate of fibrin formation. Specific such assays are described in the detailed methods below.

Typically, the amino acid sequence identity, determined at a global level (otherwise known as "global sequence identity"), between the native protein (i.e., the anchor precursor protein) and the recombinantly modified protein (i.e., the anchor protein) is at least about 60%, for example at least about 65%, 70%, 75%, 80%, 85%, 90%, 91%, 92%, 93%, 94%, 95%, 96%, 97%, 98% or at least about 99%. Determination of sequence identity at a global level may be carried out using, for example, the Needleman-Wunsch Global Sequence Alignment Tool available on the internet via the NCBI Blast® internet site (blast.ncbi.nlm.nih.gov/Blast.cgi). This tool allows a user to compare two sequences across their entire span.

For example, where the protein is CshA (SEQ ID NO:20) or a functional variant or portion thereof, it may be a protein which comprises the amino acid sequence SEQ ID NO:19 (which is the fibronectin-binding portion of CshA), or an amino acid sequence which is at least about 90% identical, at a global level, to SEQ ID NO:19. Where the protein is a variant of CshA, the global sequence identity of the variant with CshA (SEQ ID NO:20) may be less than 60%, provided that the variant comprises an amino acid sequence which is at least 90% identical, at a global level, to SEQ ID NO:19, optionally at least about 91%, 92%, 93%, 94%, 95%, 96%, 97%, 98% or at least about 99%, or which is SEQ ID NO:19.

In an alternative, where the protein is PlGF-2 (SEQ ID NO:22) or a functional variant or portion thereof, the protein comprises SEQ ID NO:21 (which is PlGF-2$_{(123-144)}$), or an amino acid sequence which is at least about 90% identical, at a global level, to SEQ ID NO:21. Where the protein is a variant of PlGF-2, the global sequence identity of the variant with PlGF-2 (SEQ ID NO:22) may be less than 60%, provided that the variant comprises an amino acid sequence which is at least 90% identical, at a global level, to SEQ ID NO:21, optionally at least about 91%, 92%, 93%, 94% or at least about 95%, or which is SEQ ID NO:21.

Where the protein is OpdA (SEQ ID NO:10 or SEQ ID NO:39) or a functional variant or portion thereof, the protein comprises the native amino acids at positions 31, 33, 145, 177, 206 and 277 as found in SEQ ID NO:10 or SEQ ID NO:39, i.e., histidine at positions 31, 33, 177 and 206, carboxylated lysine at position 145 and aspartic acid at position 277. (SEQ ID NO:10 is the sequence showing "lysine" at position 145, which the skilled person understands to be a carboxylated lysine. SEQ ID NO:39 is identical to SEQ ID NO:10 other than explicitly specifying carboxylated lysine at position 145.) Therefore, this means that the amino acids at these positions are not substituted by another amino acid and that any variant sequence comprises these positions. For example, a functional variant of SEQ ID NO:10 may comprise a portion of SEQ ID NO:10 which is at least about 90% identical to a sequence having (i.e., comprising) amino acids 31-277 of SEQ ID NO:10 (for example, amino acids 30-280, 25-285, 20-290, 15-295, 10-300, 5-305), the portion comprising histidine at positions 31, 33, 177 and 206, carboxylated lysine at position 145 and aspartic acid at position 277. A functional variant of SEQ ID NO:39 may comprise a portion of SEQ ID NO:39 which is at least about 90% identical to a sequence having (i.e., comprising) amino acids 31-277 of SEQ ID NO:39 (for example, amino acids 30-280, 25-285, 20-290, 15-295, 10-300, 5-305), the portion comprising histidine at positions 31, 33, 177 and 206, carboxylated lysine at position 145 and aspartic acid at position 277. These amino acid positions in OpdA are known to be important to the correct functioning of the enzyme.

For the avoidance of doubt, SEQ ID NO:39 describes the same protein sequence as SEQ ID NO:10, merely providing an explicit indication of carboxylated lysine at position 145, which would in any case be understood by the skilled person to be present in SEQ ID NO:10.

Reference throughout this specification to a "functional variant" indicates an amino acid sequence which is not identical to the non-variant sequence, but which displays activity which is not significantly reduced (e.g., is substantially similar) compared to the activity of the non-variant sequence. For example, a non-variant sequence may be an enzyme having a level of activity which may be assessed by the skilled person, whereas the functional variant retains a level of activity of at least 75%, preferably at least about 80%, 85%, 90% or at least about 95% compared to the non-variant sequence. In some cases, the activity of the functional variant may be greater than the activity of the non-variant. Alternatively, the non-variant sequence may be capable of binding another entity (such as a molecule, protein, peptide, antigen or cell) and the binding affinity may be assessed by the skilled person. A functional variant retains a level of binding affinity of at least 75%, preferably at least about 80%, 85%, 90% or at least about 95% compared to the non-variant sequence, or may have an increased binding affinity. The skilled person is readily able to determine whether a variant amino acid sequence is a functional variant or not.

Such recombinant methods can be used to prepare an anchor protein which is electrostatically modified and which does not comprise a —CH$_2$C(O)NCH$_3$(CH$_2$)$_3$N(CH$_3$)$_2$H$^+$ linker covalently bonded to an amino acid side chain. Typically, such an anchor protein consists of amino acids which are naturally occurring, for example which are selected from proteinogenic amino acids (including canonical amino acids) or non-proteinogenic amino acids. A proteinogenic amino acid is one which is incorporated into proteins by natural translation processes. A non-proteinogenic amino acid is one which is not utilised in natural protein translation but which may be incorporated into an amino acid sequence by a mechanism which may include natural or artificial post-translational mechanisms. Non-limiting examples of amino acids which may be included within the anchor protein are provided in Tables 2 and 3 below:

TABLE 2 examples of proteinogenic amino acids; bold indicates positively charged amino acids, italic indicates negatively charges amino acids.

| | | | | |
|---|---|---|---|---|
| Alanine | Phenylalanine | Glutamine | Arginine | Selenocysteine |
| Isoleucine | Tryptophan | Serine | Histidine | Pyrrolysine |
| Leucine | Tyrosine | Threonine | Lysine | |
| Methionine | Asparagine | *Aspartic acid* | Glycine | |
| Valine | Cysteine | *Glutamic acid* | Proline | |

Modifications of proteinogenic and non-proteinogenic amino acids are also contemplated, provided that they do not include a —CH$_2$C(O)NCH$_3$(CH$_2$)$_3$N(CH$_3$)$_2$H$^+$ linker covalently bonded to an amino acid side chain.

Non-naturally occurring amino acids may also be included (such as those which may be introduced into a protein by use of a unique codon and a corresponding aminoacyl-tRNA system), provided that any such amino acid does not comprise a —$CH_2C(O)NCH_3(CH_2)_3N(CH_3)_2$ $H^+$ linker covalently bonded to an amino acid side chain.

TABLE 3 examples of non-proteinogenic amino acids

| | | | | |
|---|---|---|---|---|
| β-alanine | γ-aminobutyric acid | δ-aminovulinic acid | 4-aminobenzoic acid | aminoisobutyric acid |
| dehydroalanine | cystathione | lanthionine | djenkolic acid | diaminopimelic acid |
| α-amino-n-butyric acid | norvaline | norleucine | alloisoleucine | t-leucine |
| α-amino-n-heptanoic acid | pipecolic acid | α,β-diaminopropionic acid | α,γ-diaminobutyric acid | ornithine |
| allothreonine | homocysteine | homoserine | β-amino-n-butyric acid | β-aminoisobutyric acid |
| γ-aminobutyric acid | α-aminoisobutyric acid | isovaline | sarcosine | N-ethyl glycine |
| N-propyl glycine | N-isopropyl glycine | N-methyl glycine | N-ethyl glycine | N-ethyl alanine |
| N-methyl β-alanine | N-ethyl β-alanine | isoserine | α-hydroxy-γ-aminobutyric acid | homonorleucine |
| tellurocysteine | telluromethionine | ornithine | citrulline | γ-carboxyglutamate |
| hydroxyproline | hypusine | pyroglutamic acid | | |

Typically, an anchor protein within the protein-polymer surfactant conjugate may comprise a percentage of positively charged amino acid residues (such as those marked bold in Table 2 above), determined as a percentage of the total number of amino acid residues in the protein, which is greater than the percentage of such residues in the corresponding anchor precursor protein. For example, the anchor precursor protein may have 5.0-17.5% of its total amino acid residues as positively charged residues and the anchor protein may have a higher percentage than in the corresponding anchor precursor protein. The anchor protein may have at least about 18%, 19%, 20%, 21%, 22%, 23%, 24%, 25%, 26%, 27%, 28%, 29% or at least about 30% of its total amino acid residues as positively charged residues. For example, the supercharged GFP described herein has about 28% of its total amino acid residues as positively charged residues whilst the supercharged OpdA described herein has about 18% of its total amino acid residues as positively charged residues. Non-supercharged naturally occurring OpdA has 13% of its total amino acid residues as positively charged residues, whilst non-supercharged GFP has 15% of its total amino acid residues as positively charged residues. The overall charge of the protein may typically be assessed at physiological pH, as described above.

The anchor protein may comprise only amino acids selected from the group consisting of alanine, isoleucine, leucine, methionine, valine, phenylalanine, tryptophan, tyrosine, asparagine, cysteine, glutamine, serine, threonine, aspartic acid, glutamic acid, glycine, proline, selenocysteine and pyrrolysine. Alternatively or additionally, the anchor protein may comprise fewer arginine and/or histidine and/or lysine residues than the number of arginine and/or histidine and/or lysine residues present in the corresponding anchor precursor protein. For example, the anchor protein may comprise no arginine and/or no histidine and/or no lysine residues. Alternatively or additionally, the anchor protein may comprise fewer positively charged residues than the corresponding anchor precursor protein, or may comprise fewer negatively charged residues than the corresponding anchor precursor protein. One or more uncharged and/or positively charged residues in the anchor precursor protein each may be replaced by a negatively charged residue, to form an anionised anchor protein. Alternatively, one or more uncharged and/or negatively charged residues in the anchor precursor protein each may be replaced by a positively charged residue, to form a cationised anchor protein.

Examples of the production of such a modified ("supercharged") protein, in the context of Green Fluorescent Protein (GFP), are disclosed in Lawrence et al. (J. Am. Chem. Soc. (2007) vol. 129 p. 10110-10112). Such so-called "supercharged" proteins have previously been used to facilitate delivery of molecules through the phospholipid bilayer cell membrane to the interior of a cell (Zang et al. (2017) PLoS One 12(6):e0180138; WO2009/134808; WO2010/129023; WO2016/069910; Thompson et al. (2012) Methods Enzymol. vol. 503 p. 293-319; McNaughton et al. (2009) Proc. Natl. Acad. Sci. U.S.A. vol. 106 p. 6111-6116). It is, therefore, wholly surprising that, when incorporated into a protein-polymer surfactant conjugate as described herein, a phospholipid composition, such as a cell, comprising an embedded protein-polymer surfactant conjugate can be obtained.

In a composition according to the invention and as mentioned above, the phospholipid bilayer may form the surface membrane of a cell. The cell may be any comprising a phospholipid bilayer, particularly a cell which does not also comprise an exterior cell wall. However, in this specification, the term "cell" encompasses a protoplast or spheroplast, i.e., a cell normally comprising a cell wall but having had at least some of said wall removed or disrupted, for example, by a mechanical or enzymatic process.

The cell may be any which a user desires to contact with a protein-polymer surfactant conjugate in order to embed the protein-polymer surfactant conjugate in the cell membrane, such as an animal or a plant cell, or a microorganism cell, for example a mammalian cell in vivo or in vitro or ex vivo such as in cell or tissue culture. The mammalian cell may be a human, dog, cat or horse cell, or a bovine, porcine or ovine cell. For example, the mammalian cell may be a human cell including a mesenchymal stem cell, or a cell derived from an embryonic stem cell or an induced pluripotent stem cell, which may be a human cell. The cell may be one which is not a human cell or human embryonic cell or human embryonic stem cell and/or is not derived from a human cell or human embryonic cell or human embryonic stem cell. The cell may also be a specialised cell such as a cardiomyocyte for targeting the heart, a chondrocyte for targeting cartilage, an osteoblast for targeting bone, a hepatocyte for targeting liver, a pancreatic islet beta cell for targeting the pancreas, a nerve cell or neural progenitor cell for targeting the brain, an endothelial cell for targeting the internal lumen of blood vessels, a myocyte for targeting muscles or a ligamentocyte for targeting ligaments. These examples are not limiting and any specialised cell might be used for any part of the body. In addition, cell lines such as CHO or HELA might be used for animal studies or in vitro studies to demonstrate cell distribution using an appropriate label.

The composition according to the invention may be one wherein the phospholipid composition forms at least a portion of the membrane of a mesenchymal stem cell (i.e., the cell membrane of the MSC is the phospholipid composition). The stem cell may be one which has not been obtained from a human embryonic cell or stem cell. The phospholipid composition may comprise one or more of:

supercharged fibronectin-binding domain of CshA;

supercharged CshA, or a supercharged functional variant or portion thereof comprising fibronectin-binding domain of CshA;

supercharged PIGF-$2_{(123-144)}$, or supercharged PIGF-2 or a supercharged functional variant or portion thereof comprising PIGF-$2_{(123-144)}$;

cationised or supercharged prothrombin or thrombin, or a cationised or supercharged functional variant of prothrombin or thrombin.

The phospholipid composition of the invention may form at least a portion of the membrane of a mesenchymal stem cell or a cardiomyocyte. In this context, the phospholipid composition may comprise supercharged fibronectin-binding domain of CshA, or supercharged CshA or a supercharged functional variant or portion of CshA comprising the fibronectin-binding domain.

When the phospholipid bilayer forms the surface membrane of a cell, the protein-polymer surfactant conjugate may be embedded in the phospholipid bilayer for 1-30 days, or 1-15 or 1-10 or 1-5 days after the phospholipid composition according to the invention is formed, by contacting the cell with the protein-polymer surfactant conjugate. For example, the protein-polymer surfactant conjugate may be embedded for about 1, 2, 3, 4, 5, 6, 7, 8, 9 or about 10 days.

The phospholipid composition according to the invention may be present within a complex composition further comprising at least one additional component, for example, water, a buffer solution, one or more components required to form a pharmaceutical composition as described below, or one or more components required to form a surgical composition such as a liquid or a scaffold material such as a membrane or a fabric.

According to a second aspect of the invention, there is provided a method of preparing a phospholipid composition according to the first aspect of the invention, the method comprising a) providing a protein-polymer surfactant conjugate; and
b) contacting a phospholipid bilayer or micelle with the conjugate;

wherein the protein-polymer surfactant conjugate comprises an anchor protein which is a cationised protein or an anionised protein and (i) is an active enzyme and/or (ii) is a protein which does not comprise a —$CH_2C(O)NCH_3(CH_2)_3 N(CH_3)_2H^+$ linker covalently bonded to an amino acid side chain, for example, to an acidic amino acid side chain.

The phospholipid bilayer may be in the form of a cell, artificial cell, liposome or other vesicle, or may form a part of a cell, artificial cell, liposome or other vesicle. In a method according to the second aspect of the invention, the phospholipid bilayer may be a cell which is contacted in step (b) with a protein-polymer surfactant conjugate as defined above and incubated at a temperature of at least about 10° C. for a period of at least about 2 minutes. The temperature may typically be about 30-40° C., for example about 30, 31, 32, 33, 34, 35, 36, 37, 38, 39 or about 40° C., for example about 37° C.±about 1° C. The time period may typically be 2-60 minutes, for example about 2, 3, 4, 5, 10, 15, 20, 30, 40, 50 or about 60 minutes, for example about 15, about 20 or about 30 minutes. The step may take place in an atmosphere of about 0-10% $CO_2$, for example, of about 5% $CO_2$. When the phospholipid bilayer is in the form of an artificial cell, liposome or other non-cell vesicle, step (b) may be conducted at room temperature (e.g., between about 15° C. and about 25° C.) with <1% $CO_2$, for example, in air.

Step (b) of the method according to the second aspect of the invention may optionally followed by a step (c) of washing the phospholipid bilayer or micelle (e.g. a cell), for example using a buffer such as Phosphate Buffered Saline (PBS), for example with two or more washing steps. The skilled person is readily able to adapt such steps as required, and to determine when a washing step is desirable.

Step (a) of the method according to the second aspect of the invention, to provide a protein-polymer surfactant conjugate, comprises contacting an anchor protein which is a cationised protein or an anionised protein with a surfactant under conditions which enable electrostatic conjugation of the surfactant with the protein. The surfactant may be added in solid or liquid form to a solution of the protein. The surfactant may be added in an amount equivalent to 0.5-5 moles surfactant per cationic site on the protein, for example, equivalent to about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or about 3.0 moles surfactant per cationic site on the protein. The protein may be in a solution with a suitable buffer such as a HEPES buffer, with or without $CoCl_2$, or in a Tris-HCl buffer. The selection of an appropriate buffer is within the routine abilities of the skilled person. The conditions may include a pH of between 5 and 8, for example of about 5, 6, 7 or about 8 (encompassing any individual intermediate pH value between 5.1 and 5.9, between 6.1 and 6.9, and between 7.1 and 7.9), and may include agitation of the mixture for 0-30 hours, for example, for about 1, 2, 3, 4, 5, 6, 7, 8, 9, 10, 11 or about 12 hours, at a temperature of 0-25° C., for example at about 4° C. or at about room temperature. For example, the conjugation conditions as described by Armstrong et al. (*Nat. Commun.* (2015) Jun. 17; 6:7405) may be suitable.

A "cationic site" is a position within the amino acid sequence of the protein which has an amino acid with a positively charged side chain or comprising a cationic (i.e., positively charged) linker. The number of cationic sites within an anchor protein may be determined without use of inventive skill by the skilled person.

The surfactant may comprise polyethylene glycol, which may, for example, have a molecular weight of at least about 500 Da, for example, at least about 1000, 1100, 1200, 1300, 1400, 1500, 1600, 1700, 1800, 1900, 2000, 2200, 2400, 2600, 2800, 3000, 3200, 3400, 3600, 3800 or at least about 4000 Da. The surfactant may be in a buffer solution at a concentration of 5-50 mg/mL, for example, about 10, 15, 20, 25, or about 30 mg/mL.

The surfactant may be S1783 (i.e., oxidised glycolic acid ethoxylate 4-nonylphenyl ether). Alternatively, the surfactant conjugate may comprise a cationic surfactant, for example, PEG-15 hydrogenated tallowmodium chloride (sold as Ethoquad® HT25).

The anchor protein may be linked to a secondary molecule, as described above, prior to contacting with the surfactant.

Step (a) may also comprise, prior to contacting the phospholipid bilayer or micelle with the protein-polymer surfactant conjugate, a buffer exchange step. The buffer exchange step may comprise a spin concentration of the product of the step of contacting the cationised or anionised protein with the surfactant. Alternatively, the buffer exchange step may comprise a dialysis step. Such methods are described in the Examples section herein and are within the routine ability of the skilled person.

When the anchor protein is an active enzyme, it may be a cationised protein which has been obtained by covalent bonding of a cationic linker (which may be polycationic) to an acidic amino acid side chain on the protein. For example, at least one acidic amino acid side chain may comprise a —$CH_2C(O)NCH_3(CH_2)_3N(CH_3)_2H^+$ linker. This may be achieved by a method in which a solution of N,N'-dimethyl-1,3-propanediamine (DMPA) or an analogue thereof is mixed with an anchor precursor protein (as defined above), in the presence of N-(3-dimethylaminopropyl)-N'-ethylcarbodiimide hydrochloride (EDC). As outlined above, the reaction is shown in FIG. 1. An analogue of DMPA may be N,N'-dimethylhexane-1,6-diamine (DMHA), N,N'-dimethylethylenediamine (DMEA), 3-dimethylamino propylamine (DMAPA), ethylenediamine (EN), 1,3-diaminopropane (DAP), 1,4-diaminobutane (DAB), 1,5-diaminopropane (DAP), 1,6-diaminohexane (DAH), hexamethylenediamine (HMA), 1,7-diaminheptane (DAH) 1,8-diaminooctane (DAO) and 2-(2-aminoethyl)guanidine (AEG). Other suitable nucleophiles may be contemplated by the skilled person, for example, charged nucleophiles. For example, nucleophiles could also include other primary, secondary and tertiary alkyl diamines and alkyl diamines terminated with a quaternary amine if the opposing terminus contains either a primary, secondary or tertiary amine. Polyalkylamines such as polyethylenimine as either linear chains or branched structures are also contemplated.

Therefore, when the anchor protein is an active enzyme, it may be obtained by a method comprising:
i) mixing a solution of an anchor precursor protein with a pH-neutralised solution of N,N'-dimethyl-1,3-propanediamine (DMPA) or analogue thereof and optionally (for example, if step (ii) is conducted non-concurrently with step (i)) adjusting the mixture to pH 5-7, for example about pH 6;
ii) subsequently or concurrently adding a carbodiimide such as N-(3-dimethylaminopropyl)-N'-ethylcarbodiimide hydrochloride (EDC) and adjusting the mixture to pH 4-7;
iii) agitating the mixture from (ii) for 1-30 hours at pH 4-7, at a temperature of 0-25° C.;
iv) dialysing the protein in the mixture from (iii) against water or buffer for at least 4 hours at pH 6.5-8.5;
v) if necessary, adjusting the pH of the mixture from (iv) to pH 6.5-8.5.

In the method, either step (iii) continues for no longer than about 120 minutes, for example, for no longer than about 90 minutes; and/or the method further comprises a step (vi) of conducting size exclusion chromatography on the mixture from step (iv), or from step (v) when present, and obtaining an eluate comprising an anchor protein at the required molecular weight. Either or both of these limitations ensure that the process is controlled to reduce or prevent protein denaturation and/or aggregation, such that the anchor protein enzyme product of the method retains enzymatic activity. This was not predictable from the disclosure of the prior art.

The solution of anchor precursor protein used in step (i) may be prepared in any conventional buffer, for example, HEPES. The anchor precursor protein solution is mixed with DMPA at a ratio of moles DMPA:number of anionic sites on the protein of 100:1-400:1, for example, about 100:1, 150:1, 200:1, 250:1, or about 300:1. EDC is added at a ratio of moles EDC:number of anionic sites on the protein of 30:1-60:1, for example, about 30:1, 31:1, 32:1, 33:1, 34:1, 35:1, 40:1, 45:1 or about 50:1.

An "anionic site" is a position within the amino acid sequence of the protein which has an amino acid with a negatively charged side chain. The number of anionic sites within an anchor precursor protein may be determined using the routine ability of the skilled person.

Step (ii) may be completed at the same time as step (i), i.e. the protein solution, DMPA and EDC may be mixed concurrently. Where step (ii) is completed after step (i), step (ii) may be a single step as defined above and immediately followed by step (iii), or may be subdivided into two steps (iia) in which a portion of the EDC is added to the mixture from step (i) and the mixture agitated for about 2, 3, 4, 5, 6, 7 or about 8 hours at a temperature of 0-25° C., followed by (iib) in which further EDC is added to the mixture from (iia) and the agitation continues; step (iib) is followed by step (iii).

The required agitation in step (iii) may be achieved by any conventional means such as stirring, for example, and the pH may be about 4, about 5, about 6 or about 7 (encompassing any intermediate pH value between 4.1 and 4.9 and between 5.1 and 5.9 and between 6.1 and 6.9). When the time period in step (iii) exceeds 120 minutes, it may continue for about 20-30 hours, for example, about 20, 21, 22, 23, 24, 25, 26, 27, 28, 29 or about 30 hours, for example about 24 hours. All steps may, for example, be conducted at about room temperature, for example, 18-23° C., or may be conducted at about 4° C.

The skilled person may determine the appropriate time period for step (iii), whether or not there is a subsequent size exclusion chromatography step, by conducting the step (iii) for a range of time periods and testing for the retention of enzyme activity, using any routine suitable assay depending on the enzyme, to determine the optimal time period for step (iii).

An example of a specific method for providing a cationised OpdA anchor protein for inclusion in a protein-polymer surfactant conjugate is as follows:
1) adding a solution of OpdA (in 30 mM HEPES with 100 µM $CoCl_2$) to a pH neutralised solution of DMPA at a ratio of DMPA to anionic sites in the OpdA of 300:1 and adjusting the pH to about 5.1;
2) adding EDC to the mixture from (1), at a ratio of moles of EDC to anionic sites in the OpdA of 50:1, in two half-additions 4 hours apart;
3) agitating the mixture from (2) for a total of about 20 hours (including the period where only the first half-addition of EDC is included) at a temperature of about 4° C.;

4) desalting the mixture from (3) using 10,000 MWCO spin concentrators;
5) conducting size exclusion chromatography on the mixture from (4) and retaining eluate comprising the cationised OpdA anchor protein.

Step (4) may be repeated about 1, 2, 3, 4, 5 or about 6 times.

An example of a specific method for providing a cationised thrombin anchor protein for inclusion in a protein-polymer surfactant conjugate is as follows:

01) adding a solution of Thrombin (in 60 mM HEPES) to a pH neutralised solution of DMPA at a ratio of DMPA to anionic sites in the Thrombin of 150:1 and adjusting the pH to about 6.5;
02) adding EDC to the mixture from (01), at a ratio of moles of EDC to anionic sites in the Thrombin of 34:1;
03) agitating the mixture from (02) for about 60 minutes at room temperature;
04) diluting the mixture from (03) with 20 mM HEPES (pH7), for example about 4-fold, at 4° C. and applying to a 10K MWCO spin concentrator.

Step (04) may be repeated about 1, 2, 3, 4, 5 or about 6 times.

In an alternative general method, the protein-polymer surfactant conjugate may be prepared by contacting an anchor protein which is an anionised protein as described with a surfactant which is a cationic surfactant. For example, the protein may be anionised by nucleophilic addition of dicarboxylic acids (HOOC—R—COOH) to the lysine sidechains of the native protein.

Alternatively or additionally to the above modifications, the anchor protein to be contacted with a surfactant as described above, i.e., for inclusion in the protein-polymer surfactant conjugate provided for use in the method according to the second aspect of the invention, may have been obtained by a recombinant method, to provide an anionised anchor protein or cationised anchor protein which does not comprise a $-CH_2C(O)NCH_3(CH_2)_3N(CH_3)_2H^+$ linker covalently bonded to an amino acid side chain, for example, to an acidic amino acid side chain. For example, the anchor protein may be obtained by a method comprising expression of a recombinant DNA sequence encoding for a supercharged protein. The resulting protein, which is the anchor protein, subsequently may be isolated.

For example, preparation of a supercharged protein may involve substituting an amino acid having an uncharged side group with an amino acid having a charged side group, or substituting an amino acid with a charged side group with a side group having the opposite charge, provided that the tertiary structure and/or biological activity of the protein is not significantly altered. This may be especially advantageous if the function/activity of the protein depends on the involvement of an amino acid with a charged side group, since the user can direct protein surface charge alterations to non-critical amino acid positions. Where the protein is an enzyme or a protein having another biological activity, the supercharged protein may comprise a functionally important portion or domain of the protein in wild-type form, i.e., the domain or portion may not include any amino acid substitutions. Alternatively or additionally, the skilled person may establish, from the literature or using routine methods, a wild-type amino acid residue at one or more positions which is critical to protein activity (e.g., enzymatic activity); the supercharged protein may comprise the wild-type amino acid at the or each position, with amino acids at other positions optionally being substituted.

Typically, the amino acid sequence identity, determined at a global level (otherwise known as "global sequence identity"), between the recombinantly modified supercharged protein (i.e., the anchor protein) and the native protein (i.e., the anchor precursor protein) is at least about 60%, for example at least about 65%, 70%, 75%, 80%, 85%, 90%, 91%, 92%, 93%, 94%, 95%, 96%, 97%, 98% or at least about 99%. Determination of sequence identity at a global level may be carried out using, for example, the Needleman-Wunsch Global Sequence Alignment Tool available on the internet via the NCBI Blast® internet site. As mentioned above, the sequence identity of a functionally important domain may be at least about 90%, 91%, 92%, 93%, 94%, 95%, 96%, 97%, 98% or at least about 99% identical between the anchor protein and the anchor precursor protein.

Such recombinant methods can be used to prepare an anchor protein which is electrostatically modified relative to the anchor precursor protein and which does not comprise a $-CH_2C(O)NCH_3(CH_2)_3N(CH_3)_2H^+$ linker covalently bonded to an amino acid side chain. Typically, such an anchor protein consists of amino acids which are naturally occurring, for example which are selected from proteinogenic amino acids (including canonical amino acids) or non-proteinogenic amino acids, as described in more detail above. Modifications of proteinogenic and non-proteinogenic amino acids are also contemplated, provided that they do not include a $-CH_2C(O)NCH_3(CH_2)_3N(CH_3)_2H^+$ linker covalently bonded to an amino acid side chain. Non-naturally occurring amino acids may also be included, as described above.

Typically, an anchor protein for inclusion in the protein-polymer surfactant conjugate for use in the method according to the second aspect of the invention may comprise a percentage of positively charged amino acid residues (such as those marked bold in Table 2 above), determined as a percentage of the total number of amino acid residues in the protein, which is greater than the percentage of such residues in the corresponding anchor precursor protein. For example, the anchor precursor protein may have 5.0-17.5% of its total amino acid residues as positively charged residues and the anchor protein may have a higher percentage than in the corresponding anchor precursor protein. The anchor protein may have at least about 18%, 19%, 20%, 21%, 22%, 23%, 24%, 25%, 26%, 27%, 28%, 29% or at least about 30% of its total amino acid residues as positively charged residues. For example, the supercharged GFP described herein has about 28% of its total amino acid residues as positively charged residues whilst the supercharged OpdA described herein has about 18% of its total amino acid residues as positively charged residues. Non-supercharged naturally occurring OpdA has 13% of its total amino acid residues as positively charged residues, whilst non-supercharged GFP has 15% of its total amino acid residues as positively charged residues. The overall charge of the protein may typically be assessed at physiological pH as described above.

The anchor protein may comprise only amino acids selected from the group consisting of alanine, isoleucine, leucine, methionine, valine, phenylalanine, tryptophan, tyrosine, asparagine, cysteine, glutamine, serine, threonine, aspartic acid, glutamic acid, glycine, proline, selenocysteine and pyrrolysine. Alternatively or additionally, the anchor protein may comprise fewer arginine and/or histidine and/or lysine residues than the number of arginine and/or histidine and/or lysine residues present in the corresponding anchor precursor protein. For example, the anchor protein may comprise no arginine and/or no histidine and/or no lysine residues. Alternatively or additionally, the anchor protein may comprise fewer positively charged residues than the corresponding anchor precursor protein, or may comprise fewer negatively charges residues than the corresponding anchor precursor protein. One or more uncharged and/or positively charged residues in the anchor precursor protein each may be replaced by a negatively charged residue, to form the anchor protein. Alternatively, one or more uncharged and/or negatively charged residues in the anchor precursor protein each may be replaced by a positively charged residue, to form the anchor protein.

Examples of the production of such a modified ("supercharged") protein, in the context of Green Fluorescent Protein (GFP), are disclosed in Lawrence et al. (*J. Am. Chem. Soc.* (2007) vol. 129 p. 10110-10112). The methods disclosed therein are readily adaptable by the skilled person to enable provision of other supercharged proteins, for example as described herein.

The recombinant DNA may comprise SEQ ID NO:2, or any polynucleotide sequence encoding for supercharged OpdA, for example, encoding for SEQ ID NO:11, which is a supercharged OpdA having carboxylated lysine at the position equivalent to position 145 in SEQ ID NO:10; this position is position 151 in SEQ ID NO:11. SEQ ID NO:40 is the same sequence as SEQ ID NO:11, explicitly indicating that carboxylated lysine is present at position 151, as would be understood by the skilled person to be the case in SEQ ID NO:11. Therefore, SEQ ID NO:2 may also be said to encode for SEQ ID NO:40.

The recombinant DNA sequence may encode for a fusion protein comprising the supercharged protein (which may be the anchor protein as described herein) and a secondary molecule. The secondary molecule may be, or may comprise, by way of non-limiting example, a labelling protein such as GFP, PsmOrange or magnetoferritin, a protein conjugated to labelling molecule or nanoparticle, an enzymatic protein such as a peroxidase or a phosphotriesterase (such as OpdA from *Agrobacterium radiobacter*) or a protease (such as thrombin), or an enzyme precursor protein such as prothrombin, an adhesion or "homing" protein such as an antibody, lectin, integrin or adhesion molecule (for example the protein CshA from *Streptococcus gordonii*), or a functional variant or portion of CshA comprising the fibronectin binding domain of CshA), a growth factor such as PIGF-2 or a portion thereof or functional variant thereof comprising PIGF-2$_{(123-144)}$, or a carrier protein such as a globin, for example, myoglobin, or a peptide or polypeptide such as a SpyCatcher or SpyTag motif.

The anchor protein may be supercharged GFP (e.g. SEQ ID NO:12) or supercharged OpdA (SEQ ID NO:11, also described by SEQ ID NO:40). Alternatively or additionally, the secondary molecule included within the fusion protein may be a thrombin or a prothrombin (e.g., SEQ ID NO:25 or 26), CshA (e.g., SEQ ID NO:20, from *Streptococcus gordonii*) or a functional variant or portion thereof comprising the fibronectin binding domain (SEQ ID NO:19), OpdA (SEQ ID NO:10, from *Rhizobium radiobacter*, or a functional variant or portion thereof; this sequence is also described as SEQ ID NO:39), Placental Growth Factor-2 (SEQ ID NO:22), or a functional variant or portion thereof comprising PIFG-2$_{(123-144)}$ (SEQ ID NO:21), a SpyCatcher polypeptide (SEQ ID NO:23) or a SpyTag polypeptide (SEQ ID NO:24). Therefore, the secondary molecule may comprise SEQ ID NO:19 or a functional variant thereof having at least about 90%, 91%, 92%, 93%, 94%, 95%, 96%, 97%, 98% or at least about 99% sequence identity to SEQ ID NO:19. Or, the secondary molecule may comprise SEQ ID NO:19 or a functional variant thereof having at least about 90%, 91%, 92%, 93%, 94% or at least about 95% sequence identity to SEQ ID NO:21.

The term "thrombin" may indicate a thrombin from any species, for example bovine thrombin or human thrombin. The skilled person is readily able to identify alternative suitable thrombin molecules.

The recombinant DNA sequence encoding a fusion protein may be selected from SEQ ID NOs:4-7, or equivalent sequences to any of these in which codons have been altered but wherein the sequence encodes for the same amino acid sequence. The fusion protein may have an amino acid sequence selected from SEQ ID NOs:13-16, or for a functional variant of any of these having at least about 60%, for example at least about 65%, 70%, 75%, 80%, 85%, 90%, 91%, 92%, 93%, 94%, 95%, 96%, 97%, 98% or at least about 99% sequence identity with the non-variant sequence. A functional variant may comprise SEQ ID NO:19 or 21. Therefore, the recombinant DNA sequence may be any which encodes for any of SEQ ID NO:13-16, or for a functional variant as described. Determination of sequence identity at a global level may be carried out as described above. Other proteins which may be electrostatically modified for use in the invention are listed in Table 4:

TABLE 4 listing of suitable adhesion proteins

| Uniprot ID | Protein | Organism | SEQ ID NO: |
|---|---|---|---|
| A8AWJ3_STRGC | CshA | *Streptococcus gordonii* | 20 |
| Q54194_STRGN | CshA (variant) | *Streptococcus gordonii* | 27 |
| Q8VP45_STRGN | CshB | *Streptococcus gordonii* | 28 |
| Q9KWR3_STRGN | Hsa | *Streptococcus gordonii* | 29 |
| Q48S75_STRPM | AspA | *Streptococcus pyogenes* | 30 |
| Q8E589_STRA3 | BspA | *Streptococcus agalactiae* | 31 |
| PFBA_STRR6 | PfbA | *Streptococcus pneumoniae* | 32 |
| Q8GH87_MORCA | UspA1 | *Moraxella catarrhalis* | 33 |
| Q51227_NEIME | OpcA | *Neisseria meningitidis* | 34 |
| Q4U4F4_FUSNU | FadA | *Fusobacterium nucleatum* | 35 |
| FIMH_ECOLI | FimH | *Escherichia coli* | 36 |
| MRKD_KLEPN | MrkD | *Klebsiella pneumoniae* | 37 |
| CSGA_ECOLI | CsgA | *Escherichia coli* | 38 |

Reference to "CshA", as used throughout this specification, may refer to SEQ ID NO:20 or 27, for example, SEQ ID NO:20.

The recombinant DNA sequence may be expressed according to any routine method, for example, using any expression system such as expression in *E. coli*, in accordance with the routine abilities of the skilled person. Isolation of the expressed anchor protein from the expression system is also within the routine abilities of the skilled person.

A third aspect of the invention provides a method of labelling a cell with a protein label, comprising a method according to the second aspect of the invention, wherein the phospholipid bilayer of step (b) forms the external membrane of the cell and the protein-polymer surfactant conjugate comprises the protein label. The protein label may be the anchor protein or the secondary molecule, where present. The protein label may be GFP, PsmOrange or magnetoferritin, a protein conjugated to labelling molecule or nanoparticle, an enzymatic protein such as a peroxidase or a phosphotriesterase (such as OpdA from *Agrobacterium radiobacter*, or a functional variant or portion thereof) or a protease (such as thrombin), an enzyme precursor (such as prothrombin), an adhesion or "homing" protein such as an antibody, lectin, integrin or adhesion molecule (for example the protein CshA from *Streptococcus gordonii*, or a functional variant or portion thereof comprising the fibronectin binding domain of CshA such as SEQ ID NO:19, or any of the proteins listed in Table 4), a growth factor (such as PIGF-2 or a functional variant or portion thereof comprising PIGF-$2_{(123-144)}$ (SEQ ID NO:21)), or a carrier protein such as a globin, for example, myoglobin. In addition to the options above, the secondary molecule may additionally be selected from a peptide, polypeptide or other molecule, such as a SpyCatcher or SpyTag motif, biotin or streptavidin The protein label may be a detectable protein label such as a fluorescent protein, or a protein conjugated to a labelling molecule such as a metal particle, a nanoparticle, a fluorescent dye or a fluorescent probe. The label may be one which facilitates separation of a labelled cell from an equivalent cell which does not comprise the protein-polymer surfactant conjugate. The label may be one which is capable of interacting with or binding to a label-binding moiety; for example, there the protein label is an antibody, the label-binding moiety may be an antigen capable of binding to the antibody; where the protein label is a SpyCatcher polypeptide the label-binding moiety may be a SpyTag polypeptide; where the protein label is a SpyTag polypeptide the label-binding moiety may be a SpyCatcher polypeptide; where the protein label is streptavidin, the label-binding moiety may be biotin. The label-binding moiety itself may be further attached to a cell or form part of a larger construct, molecule or structure, by the methods described herein or by other methods known in the art.

A related aspect of the invention therefore provides a cell obtained by the method according to the third aspect of the invention. Such a cell is typically a phospholipid composition according to the first aspect of the invention. The term "cell" as used throughout this specification, in relation to any aspect or embodiment of the invention described herein, may be a prokaryotic or eukaryotic cell, for example a bacterial, fungal, protist, plant, insect, reptile, bird, fish or mammal cell, for example a human, dog, cat or horse cell, or a bovine, porcine or ovine cell. The cell may be one which is not a human cell, and/or not a human embryonic cell or cell derived therefrom, and/or not a human embryonic stem cell or cell derived therefrom.

A fourth aspect of the invention provides a method for forming a tissue engineering scaffold, comprising use of a phospholipid composition (such as a cell) according to the first aspect of the invention (for example obtained by the method according to the second or third aspects of the invention), wherein the protein-polymer surfactant conjugate comprises a protein (which may be the anchor protein or may be a secondary molecule) which is, in its naturally occurring form, known to promote growth and/or healing of tissue. For example, the anchor protein may be cationised or supercharged thrombin or prothrombin or may be a cationised or supercharged functional variant or portion of thrombin or prothrombin, or the secondary molecule may be thrombin or prothrombin (e.g., SEQ ID NO:25 or 26) or a functional variant or portion of thrombin or prothrombin, or PIGF-2 (SEQ ID NO:22), or a functional variant or portion thereof comprising SEQ ID NO:21. For example, the method may comprise contacting a cell, which is a phospholipid composition according to the first aspect of the invention wherein the anchor protein is cationised or supercharged thrombin or wherein the secondary molecule is thrombin, with a fibrinogen composition such as a fibrinogen-containing gel, or with a fibrinogen-containing structure formed by the method described in Armstrong et al. (*Adv. Healthcare Mat.* (2016) vol. 5 p 1724-1730) and co-pending application PCT/GB2016/053358 (published as WO2017/187114). Alternatively or additionally, the method may comprise contacting a cell, which is a phospholipid composition according to the first aspect of the invention wherein the protein-polymer surfactant conjugate comprises a secondary molecule which is PIGF-2 (SEQ ID NO:22), or a functional variant or portion thereof comprising SEQ ID NO:21, with a material which comprises one or more of fibronectin, vitronectin, tenascine C, osteopontin and/or fibrinogen. The material may be an extracellular matrix and/or gel and/or or a structure formed by the method described in Armstrong et al. (*Adv. Healthcare Mat.* (2016) vol. 5 p 1724-1730) and co-pending application PCT/GB2016/053358 (published as WO2017/187114).

A fifth aspect of the invention provides a tissue engineering scaffold comprising a phospholipid composition (such as a cell) according to the first aspect of the invention, for example a scaffold prepared by the method according to the fourth aspect of the invention. The protein-polymer surfactant conjugate may comprise a protein (which may be the anchor protein or may be a secondary molecule) which is, in its naturally occurring anchor precursor protein form, known to promote growth and/or healing of tissue. For example, the anchor protein may be cationised or supercharged thrombin or prothrombin or a cationised or supercharged functional variant or portion of thrombin or prothrombin, or the secondary molecule may be thrombin or prothrombin (e.g., SEQ ID NO:25 or 26) or a functional variant or portion of thrombin or prothrombin, or may be PIGF-2 (SEQ ID NO:22) or a functional variant or portion thereof comprising SEQ ID NO:21. The tissue engineering scaffold may be formed by a method comprising the method described in Armstrong et al. (*Adv. Healthcare Mat.* (2016) vol. 5 p 1724-1730) and co-pending application PCT/GB2016/053358 (published as WO2017/187114). Alternatively or additionally, the tissue engineering scaffold may comprise one or more of fibronectin, vitronectin, tenascine C, osteopontin and/or fibrinogen.

A sixth aspect of the invention provides a method of promoting tissue growth and/or healing, comprising use of a cell which is (or comprises) a phospholipid composition according to the first aspect of the invention (for example obtained by the method according to the second aspect of the invention), wherein the protein-polymer surfactant conjugate comprises a protein (which may be the anchor protein or may be a secondary molecule) which is, in its naturally occurring anchor precursor protein form, known to promote growth and/or healing of the tissue, by introducing the cell to a site where the tissue is desired to grow and/or heal. For example, the cell may be a mesenchymal stem cell and the anchor protein may be cationised or supercharged thrombin or prothrombin (e.g., SEQ ID NO:25 or 26) or a cationised or supercharged functional variant of thrombin or prothrombin, or the secondary molecule may be thrombin or prothrombin (e.g., SEQ ID NO:25 or 26) or a functional variant or portion of thrombin or prothrombin, or PIGF-2 (SEQ ID NO:22), or a functional variant or portion thereof comprising SEQ ID NO:21. The tissue may be in vitro or ex vivo, or may be in vivo within an animal, for example a mammal such as a human, dog, cat or horse. The method may comprise use of a scaffold according to the fifth aspect of the invention, and/or of a pharmaceutical composition according to the eleventh aspect of the invention, and/or of a surgical composition according to the twelfth aspect of the invention.

A seventh aspect of the invention provides a method of targeting a cell to a tissue, comprising use of a cell which is a phospholipid composition according to the first aspect of the invention (for example obtained by the method according to the second aspect of the invention), wherein the phospholipid bilayer forms at least a portion of the external membrane of the cell and the protein-polymer surfactant conjugate comprises a protein (which may be the anchor protein or a secondary molecule) specific for the tissue, such as an antibody, lectin, integrin or adhesin. The tissue may be in vitro or ex vivo, or may be in vivo within an animal, for example a mammal such as a human, dog, cat or horse. The tissue may be cardiac tissue and the cell may be a mesenchymal stem cell or a cardiomyocyte, in which case the protein-polymer surfactant conjugate may comprise a secondary molecule which is CshA or a functional variant or portion thereof comprising SEQ ID NO:19. The method may comprise introducing the cell to a system (which may be a system which is not a human or animal body) in which the tissue is present, such as a tissue culture container, an ex vivo tissue (for example, one obtained from an individual suffering from myocardial infarction, cardiomyopathy and/or myocarditis), or a body comprising the tissue, for example a body suffering from myocardial infarction, cardiomyopathy and/or myocarditis. The tissue may, therefore, be in vitro or ex vivo, or may be in vivo within an animal, for example a mammal such as a human, dog, cat or horse. The method may comprise use of a scaffold according to the fifth aspect of the invention, and/or of a pharmaceutical composition according to the eleventh aspect of the invention, and/or of a surgical composition according to the twelfth aspect of the invention.

An eighth aspect of the invention provides a method of delivering a protein to the interior of a cell, comprising the method according to the second aspect of the invention, wherein the phospholipid bilayer forms the external membrane of the cell. This is enabled by allowing or promoting the process of endocytosis, well known to the skilled person, by which portions of the cell membrane and/or molecules associated with the membrane are internalised into the cell. The composition of the protein-polymer surfactant conjugate may promote or inhibit the process, i.e., promoting or inhibiting the speed/rate of endocytosis of the embedded protein-polymer surfactant conjugate. The cell may be a cell which is not a human embryonic cell or human embryonic stem cell. The cell may be a cell which is in vitro or ex vivo, i.e. a cell which is not in vitro within a human or animal body.

A ninth aspect of the invention provides a phospholipid composition according to the first aspect of the invention, for use in therapy. The phospholipid composition may be a cell such as a mesenchymal stem cell. In the ninth aspect, the phospholipid composition may be for use in a method of promoting tissue growth and/or healing, wherein the embedded protein-polymer surfactant conjugate comprises a protein (which may be the anchor protein or a secondary molecule) known to promote growth and/or healing of the tissue. For example, the protein may be cationised or supercharged thrombin or prothrombin or a cationised or supercharged functional variant of thrombin or prothrombin, or the protein-polymer surfactant conjugate may comprise a secondary molecule which is thrombin or prothrombin (e.g., SEQ ID NO:25 or 26) or a functional variant or portion of thrombin or prothrombin, or PIGF-2 (SEQ ID NO:22), or a functional variant or portion thereof comprising SEQ ID NO:21. Alternatively, the protein known to promote growth and/or healing of the tissue may be myoglobin, in which case the tissue may be cartilage. Alternatively, the secondary molecule may be CshA or a functional variant or portion thereof comprising SEQ ID NO:19, in which case the tissue may be heart tissue and the composition may be for use in a method for the treatment of myocardial infarction, cardiomyopathy and/or myocarditis. In this case, the cell may be a cardiomyocyte. The tissue may be in vitro or ex vivo, or may be in vivo within an animal, for example a mammal such as a human, dog, cat or horse. The method may comprise use of a scaffold according to the fifth aspect of the invention, and/or of a pharmaceutical composition according to the eleventh aspect of the invention and/or of a surgical composition according to the twelfth aspect of the invention.

Alternatively, in the ninth aspect of the invention the phospholipid composition according to the first aspect of the invention may be for use in the treatment of a poisoned human or animal, for example a human or animal which has been contacted with a poison. A tenth aspect of the invention provides a method for the treatment of a poisoned human or animal, for example a human or animal which has been contacted with a poison, comprising contacting the human or animal with a composition according to the first aspect of the invention, or administering such a composition to the human or animal in a therapeutically effective amount. "Contacted with a poison" may indicate that the human or animal has ingested the poison with or as food or drink, or inhaled the poison, or absorbed the poison after contact with the skin or other exterior body surface, or internalised the poison by any other means. The term "poisoned" is a routinely used term which may indicate that the normal health of the human or animal is reduced or negatively impacted following the contact with the poison and the term "treatment" may indicate that the health of the human or animal is improved or restored to a pre-poisoning state. "Treatment" may encompass avoidance or prevention of death of the human or animal where this would have been the expected outcome after contact of the human or animal with the poison, in the absence of treatment in accordance with the ninth aspect of the invention. Reduced and/or improved health may be determined by any routine measure, for example, occurrence or reduction of a rash, bleeding, vomiting, diarrhoea, increased temperature, dehydration, weight loss, sight loss, hearing loss, muscle spasm and/or paralysis, by way of non-limiting example. The term "poison" encompasses any substance which adversely impacts the normal functioning of a cell or organism, including a human or animal body or a plant, and includes toxins and venoms, as well as a pesticide or a nerve agent, by way of non-limiting example.

In the ninth or tenth aspect of the invention, the composition according to the first aspect of the invention may (a) comprise an anchor protein which is an enzyme which can neutralise the poison; or (b) comprise an anchor protein which is linked to a secondary molecule which can bind to or neutralise the poison. The term "neutralise" indicates that the poison substance is broken down or otherwise altered (or its effect in the human or animal body is altered) so that it is no longer toxic (i.e., harmful to the human or animal), or so that the toxicity is reduced. The anchor protein may be cationised or supercharged OpdA, or a cationised or supercharged functional variant or portion thereof capable of degrading an organophosphorus compound, or the secondary molecule may comprise OpdA or a functional variant or portion thereof capable of degrading an organophosphorus compound.

In the sixth, seventh, eighth, ninth or tenth aspects of the invention, the phospholipid composition may be in the form of a pharmaceutical composition, which forms an eleventh aspect of the invention, further comprising a pharmaceutically acceptable carrier, diluent or vehicle. For example, the pharmaceutical composition may be in the form of a sterile injectable preparation which may be an aqueous or an oleaginous suspension, or a suspension in a non-toxic parenterally-acceptable diluent or solvent. The aqueous suspension may be prepared in, for example, mannitol, water, Ringer's solution or isotonic sodium chloride solution. Alternatively, it may be prepared in phosphate buffered saline solution. The oleaginous suspension may be prepared in a synthetic monoglyceride, a synthetic diglyceride, a fatty acid or a natural pharmaceutically-acceptable oil. The fatty acid may be an oleic acid or an oleic acid glyceride derivative. The natural pharmaceutically-acceptable oil may be an olive oil, a castor oil, or a polyoxyethylated olive oil or castor oil. The oleaginous suspension may contain a long-chain alcohol diluent or dispersant, for example, conforming to Ph. Eur. and/or Ph. Helv. The pharmaceutical composition may comprise one or more pharmaceutically or otherwise biologically active agents in addition to the phospholipid composition of the invention. For example, the composition may include a therapeutic agent such as a conventional drug, antibody or other protein component.

A twelfth aspect of the invention provides a surgical composition comprising the phospholipid composition according to the first aspect of the invention, and fibrinogen and/or a surgically acceptable carrier, diluent or vehicle, for example any those mentioned above for the eleventh aspect of the invention. A surgically acceptable carrier, diluent or vehicle may comprise a hydrogel. The surgically acceptable carrier may be a scaffold material such as a membrane or a fabric. The scaffold material may be formed by a method comprising the method described in Armstrong et al. (Adv. Healthcare Mat. (2016) vol. 5 p 1724-1730) and co-pending application PCT/GB2016/053358 (published as WO2017/187114). In some embodiments, the surgical composition may be referred to herein as a "surgical glue".

A thirteenth aspect of the invention provides a method of decontaminating a sample comprising a poison, comprising either: (a) contacting the sample with a composition according to the first aspect of the invention, wherein the anchor protein is an enzyme which can neutralise the poison; or (b) contacting the sample with a composition according to the first aspect of the invention, wherein the anchor protein is linked to a secondary molecule which can bind to or neutralise the poison. The term "neutralise" indicates that the poison substance is broken down or otherwise altered so that it is no longer toxic, or so that the toxicity is reduced. A sample may be any liquid sample (such as a water sample) or a solid sample (which may be any solid surface, or land, or a soil sample, or fabric, for example clothing or material for use as bed linen). The poison may be any chemical which is toxic to humans, animals, insects, fish and/or plants, for example a pesticide or a nerve agent. In the ninth aspect of the invention, the anchor protein, or the secondary molecule when present, may be an organophosphate hydrolase enzyme such as OpdA obtained from *Rhizobium radiobacter*, or a homologous enzyme obtained from another organism or adapted from such an enzyme.

A fourteenth aspect of the invention provides a polypeptide comprising a fusion protein of: a supercharged anchor protein and any of SEQ ID NOs:19-38; or a supercharged anchor protein and a functional variant of any of any of SEQ ID NOs:19-38 having at least 60% sequence identity thereto. For example, the supercharged anchor protein may be scGFP and the polypeptide may comprise at least one of SEQ ID NOs:13-16 or a functional variant of any of these having at least about 60%, for example at least about 65%, 70%, 75%, 80%, 85%, 90%, 91%, 92%, 93%, 94%, 95%, 96%, 97%, 98% or at least about 99% sequence identity with the non-variant sequence. In an alternative fourteenth aspect of the invention, there is provided a polypeptide comprising a supercharged version of SEQ ID NO:10, also described by SEQ ID NO:39 (e.g., comprising SEQ ID NO:11, also described by SEQ ID NO:40), or comprising a supercharged version of any of SEQ ID NOs:10, 19-22 or 25-39. A fifteenth aspect of the invention provides a recombinant nucleic acid sequence (i.e., a polynucleotide), such as a DNA sequence, encoding for a polypeptide according to the fourteenth aspect of the invention, for example, comprising at least one of SEQ ID NOs:2 or 4-7, or equivalent sequences to any of these in which codons have been altered but wherein the sequence encodes for the same amino acid sequence. The polypeptide according to the fourteenth aspect of the invention or the nucleic acid according to the fifteenth aspect of the invention may be for use in therapy; for example, where the polypeptide comprises any of SEQ ID NO:14, 19, 20 or 27-38, the polypeptide according to the fourteenth aspect of the invention or the nucleic acid according to the fifteenth aspect of the invention may be for use in a method of treatment of myocardial infarction, cardiomyopathy and/or myocarditis.

Therefore, a sixteenth aspect of the invention provides a therapeutic method comprising administering a polypeptide according to the fourteenth aspect of the invention or the nucleic acid according to the fifteenth aspect of the invention, or a pharmaceutical composition comprising such a polypeptide or nucleic acid sequence, to a subject requiring therapeutic treatment. Such a pharmaceutical composition may by in a form as described above in relation to the eleventh aspect of the invention. For example, the pharmaceutical composition may further comprise a pharmaceutically acceptable carrier, diluent or vehicle, as described above. The method may be a method of treatment of myocardial infarction, cardiomyopathy and/or myocarditis comprising administering a therapeutic amount of a polypeptide comprising any of SEQ ID NO:14, 19, 20 or 27-38, or a nucleic acid sequence encoding for one or more of these, or a pharmaceutical composition comprising one or more such polypeptide or nucleic acid sequence, to a subject in need thereof (i.e., a subject suffering from one or more of myocardial infarction, cardiomyopathy and/or myocarditis).

Throughout the description and claims of this specification, the words "comprise" and "contain" and variations of the words, for example "comprising" and "comprises", mean "including but not limited to", and do not exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be described, by way of example only, with reference to the accompanying drawings, in which.

EXAMPLES

Figure 1:
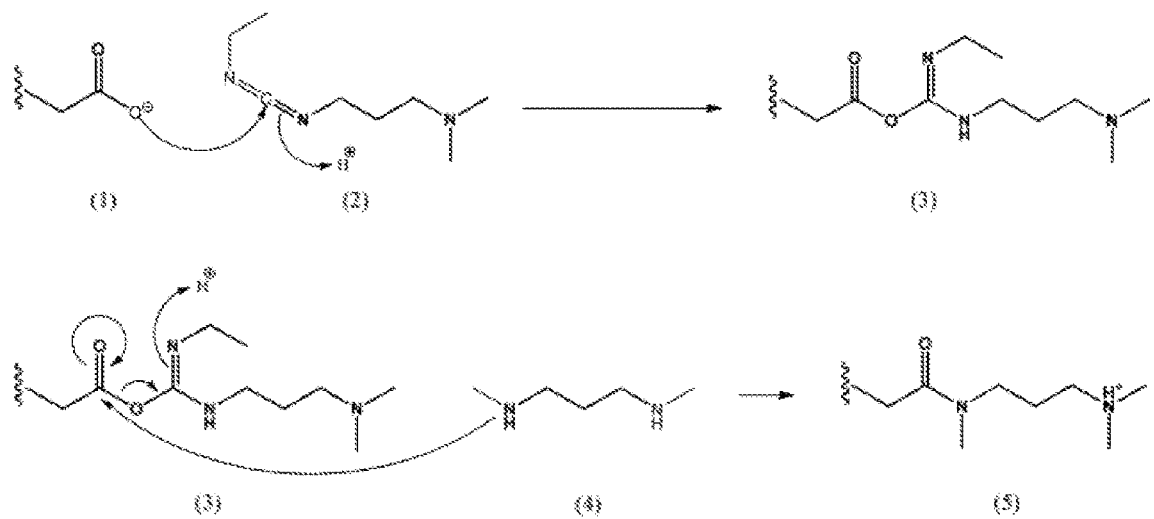
FIG. 1 shows the reaction pathway for the covalent alteration of glutamic acid and aspartic acid residues via a nucleophilic addition-elimination mechanism.
Figure 2:
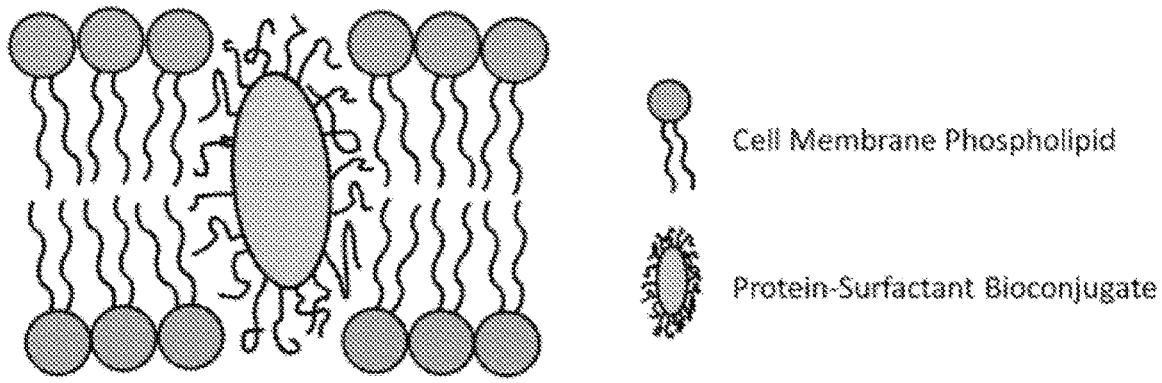
FIG. 2 is a diagram showing a protein-polymer surfactant conjugate (or "protein-surfactant bioconjugate") inserted into a phospholipid bilayer.
Figure 3:
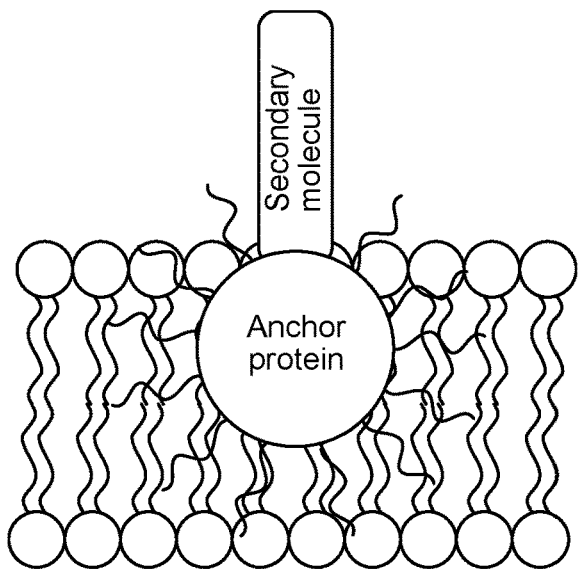
FIG. 3 is a diagram showing a protein-polymer surfactant conjugate comprising an anchor protein and a secondary molecule, with the secondary molecule positioned outside the membrane.
Figure 4:
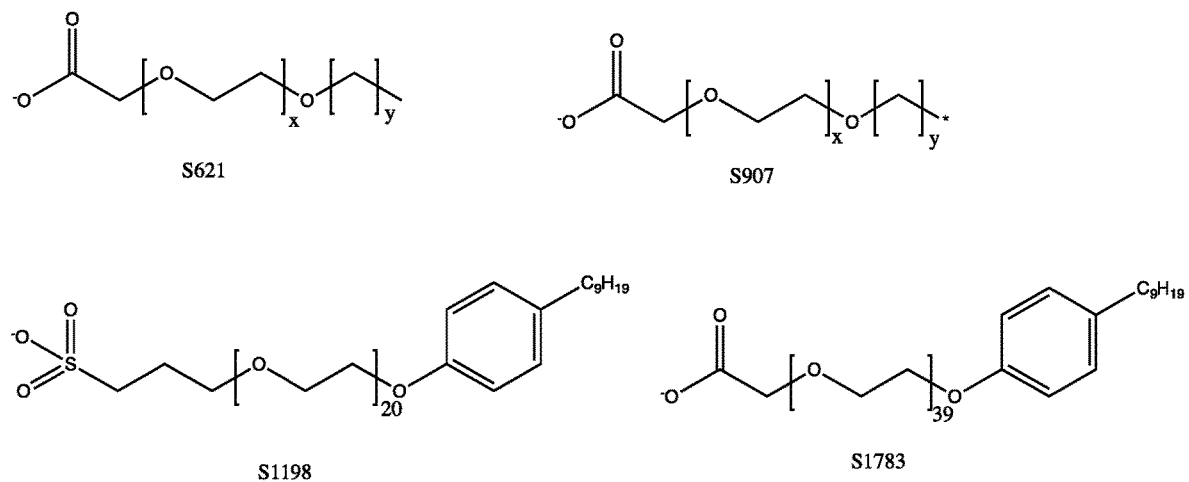
FIG. 4 shows the chemical structure of various surfactants used in the work described herein (for S621 and S907 x=11-13, for S621 y=7-9, for S907 y=14-15)

General Methods
Plasmid Preparation

The OpdA gene was acquired in a pETMCSI vector, and required no further processing. The scOpdA gene was inserted into a pETMCSI vector via Gibson assembly, as described previously in Gibson et al. (Nat Methods. (2009) Apr. 12; 6(5):343-5). scGFP-CshA, scGFP-SpyCatcher, mCherry-SpyTag, CshA-SpyTag, scGFP-OpdA, and scGFP-PIGF genes were inserted into pOPINF vectors via the In-Fusion™ cloning system, according to manufacturer's instructions. The vectors were amplified via transformation into Stellar cells (Clontech, US) or Top10 cells (Thermo Fisher Scientific, US), followed by miniprep purification (Qiagen, Germany), each according to the manufacturer's instructions. DNA and amino acid sequences are listed in Table 5:

TABLE 5

Protein gene and amino acid sequences utilised herein

| Protein/construct as referred to herein | Gene sequence | Amino acid sequence |
|---|---|---|
| OpdA | SEQ ID NO: 1 | SEQ ID NO: 10; SEQ ID NO: 39 |
| scOpdA | SEQ ID NO: 2 | SEQ ID NO: 11; SEQ ID NO: 40 |
| scGFP | SEQ ID NO: 3 | SEQ ID NO: 12 |
| scGFP-OpdA | SEQ ID NO: 4 | SEQ ID NO: 13 |
| scGFP-CshA | SEQ ID NO: 5 | SEQ ID NO: 14 |
| scGFP-PIGF$_{(123-144)}$ | SEQ ID NO: 6 | SEQ ID NO: 15 |
| scGFP-SpyCatcher | SEQ ID NO: 7 | SEQ ID NO: 16 |
| mCherry-SpyTag | SEQ ID NO: 8 | SEQ ID NO: 17 |
| CshA-SpyTag | SEQ ID NO: 9 | SEQ ID NO: 18 |
| Fibronectin binding domain of CshA | — | SEQ ID NO: 19 |
| CshA | — | SEQ ID NO: 20 |
| PIGF-2$_{(123-144)}$ | — | SEQ ID NO: 21 |
| PIGF-2 | — | SEQ ID NO: 22 |
| SpyCatcher | — | SEQ ID NO: 23 |
| SpyTag | — | SEQ ID NO: 24 |
| bovine prothrombin | — | SEQ ID NO: 25 |
| human prothrombin | — | SEQ ID NO: 26 |

Protein Expression

OpdA, scOpdA, scGFP-CshA, scGFP-OpdA, and scGFP-PIGF$_{(123-144)}$ were obtained by expression in BL21(DE3) cells (New England Biolabs, USA), transformed with vectors containing their respective genes, using routine methods. Protein specific parameters are outlined in Table 6. Bovine thrombin and human fibrinogen were obtained from commercial sources (Sigma, Cat. No T7326 and F3879, respectively).

TABLE 6

Protein expression parameters

| Protein | Medium | Temperature | Induction |
|---|---|---|---|
| OpdA | Terrific broth, with 100 μM CoCl$_2$ | 30° C. | None |
| scOpdA | Terrific broth, with 100 μM CoCl$_2$ | 30° C. | 1 mM IPTG when Abs$_{600}$ ≥ 0.6 |

TABLE 6-continued

Protein expression parameters

| Protein | Medium | Temperature | Induction |
| --- | --- | --- | --- |
| scGFP-OpdA | Terrific broth, with 100 µM $CoCl_2$, 10 g/L NaCl | 37° C. | 1 mM IPTG when $Abs_{600} \geq 0.6$ |
| scGFP-CshA | Terrific broth | 37° C. | 1 mM IPTG when $Abs_{600} \geq 0.6$ |
| scGFP-PIGF$_{(123-144)}$ | Lysogeny broth | 37° C. | 1 mM IPTG when $Abs_{600} \geq 0.6$ |
| scGFP-SpyCatcher | Terrific broth | 37° C. | 1 mM IPTG when $Abs_{600} \geq 0.6$ |
| mCherry-SpyTag | Terrific broth | 37° C. | 1 mM IPTG when $Abs_{600} \geq 0.6$ |
| CshA-SpyTag | Terrific broth | 37° C. | 1 mM IPTG when $Abs_{600} \geq 0.6$ |

Protein Purification

Lysis buffer was added to cell pellets and lysed using pulse sonication, using routine methods. The protein was then purified using fast protein liquid chromatography (FPLC). Proteins were further purified using size exclusion chromatography, using routine methods.

Protein specific purification steps are outlined in Table 7. No purification was required for the commercially purchased thrombin or fibrinogen.

TABLE 7

Protein purification conditions

| Protein | Method | Lysis buffer | Elution buffer |
| --- | --- | --- | --- |
| OpdA | Anion exchange (DEAE column) | 30 mM HEPES, 100 µM $CoCl_2$, pH 8 | N/A |
| scOpdA | IMAC (Ni-NTA column) | 30 mM HEPES, 1.5M NaCl, 20 mM imidazole, pH 8 | 30 mM HEPES, 1.5M NaCl, 1M imidazole, pH 8 |
| scGFP-OpdA | IMAC (Ni-NTA column) | 20 mM Sodium phosphate, 1M NaCl, 2 nM $MgCl_2$, 50 mM imidazole, pH 8 | 20 mM Sodium phosphate, 1M NaCl, 2 nM $MgCl_2$, 500 mM imidazole, pH 8 |
| scGFP-CshA | IMAC (Ni-NTA column) | 20 mM Tris-HCl, 1M NaCl, 20 mM imidazole, pH 7.5 | 20 mM Tris-HCl, 1M NaCl, 500 mM imidazole, pH 7.5 |
| scGFP-PIGF$_{(123-144)}$ | IMAC (Ni-NTA column) | 20 mM Tris-HCl, 1M NaCl, 20 mM imidazole, pH 7.5 | 20 mM Tris-HCl, 1M NaCl, 500 mM imidazole, pH 7.5 |
| scGFP-SpyCatcher | IMAC (Ni-NTA column) | 20 mM Tris-HCl, 1M NaCl, 20 mM imidazole, pH 7.5 | 20 mM Tris-HCl, 1M NaCl, 500 mM imidazole, pH 7.5 |
| mCherry-SpyTag | IMAC (Ni-NTA column) | 20 mM Tris-HCl, 1M NaCl, 20 mM imidazole, pH 7.5 | 20 mM Tris-HCl, 1M NaCl, 500 mM imidazole, pH 7.5 |
| CshA-SpyTag | IMAC (Ni-NTA column) | 20 mM Tris-HCl, 1M NaCl, 20 mM imidazole, pH 7.5 | 20 mM Tris-HCl, 1M NaCl, 500 mM imidazole, pH 7.5 |

Synthesis of Glycolic Acid Ethoxylate 4-nonylphenyl ether (Oxidised IGEPAL-00890) Surfactant Surfactant was prepared as described in Armstrong et al. (Nat. Commun. (2015) Jun. 17; 6:7405). Briefly, 2 g IGEPAL CO-890 dissolved in 50 mL deionised-water was mixed with 30 mg 2,2,6,6,-tetramethyl-1-piperidinyloxyl (TEMPO), 50 mg NaBr, and 5 mL NaClO solution containing 10-15% available chlorine. The solution was periodically adjusted to pH 11 and stirred for 24 hours. The reaction was quenched with ethanol and adjusted to pH 1. Solvent extraction was performed with 3 washes of 80 mL aliquots of chloroform, then 3 washes with 80 mL aliquots of deionised water adjusted to pH 1. The resulting solution was dried under reduced pressure at 40° C. The remaining solid was redissolved in 40 mL ethanol, recrystallised at −20° C., the ethanol decanted, and the crystals dried under reduced pressure at 65° C.

Protein-Surfactant Conjugation

To form the conjugated constructs, glycolic acid ethoxylate 4-nonylphenyl ether was added to a solution of cationised protein or protein comprising supercharged GFP or OpdA (see below). Any excess surfactant may be removed via dialysis, using 14,000 MWCO tubing.

The specific parameters are presented in Table 8.

TABLE 8

| | | Conjugation parameters | | | |
|---|---|---|---|---|---|
| Protein | Surfactant form | Moles of surfactant per cationic site | Buffer | Time | Temperature |
| cationised OpdA | 10 mg/mL solution | 1 | 30 mM HEPES, 100 µM $CoCl_2$, pH 8 | 1 hour | 4° C. |
| cationised Thrombin | Solid | 1.4 | 60 mM HEPES, pH 7 | 1 hour | Room temperature |
| scGFP-CshA/ OpdA/ $PIGF_{(123-144)}$ | 25 mg/mL solution | 1.4 | 20 mM Tris-HCl, pH 7.5 | Overnight | 4° C. |

Mass Spectrometry

Mass spectrometry was performed using a Bruker ultrafleXtreme MALDI-TOF/TOF mass spectrometer in linear positive mode. The matrix was a saturated solution of either sinapinic acid or α-hydroxycinnamic acid in a mixture of equal volumes acetonitrile and water, with a final concentration of 0.1% trifluoroacetic acid. 0.5 µL of 1:1 sample and matrix mixture was spotted on a ground steel plate for analysis.

Dynamic Light Scattering and Zeta Potentiometry

Dynamic light scattering (DLS) and zeta potentiometry analyses were performed on a Zetasizer Nano SP (Malvern Instruments, UK), and the data analysed using Zetasizer software (Malvern Instruments).

Small Angle X-ray Scattering

Small angle X-ray scattering was performed on the B21 beamline at the Diamond Light Source, Oxford. Samples were concentrated with 10,000 MWCO spin concentrators and flow-through retained for use as backgrounds. The samples were then spun through 1,000,000 MWCO spin concentrators to remove large contaminants. Samples were exposed for 18 frames of 10 seconds each. Data analyses were performed with the ScÅtter software package, using ATSAS plugins.

Cell Culture

Human mesenchymal stem cells (hMSCs) were harvested from the proximal femur bone marrow of osteoarthritic patients undergoing total hip replacement surgery, in full accordance with Bristol Southmead Hospital Research Ethics Committee guidelines (reference #078/01), and having received informed consent from all patients. Cells were cultured at 5% CO2, using low-glucose DMEM, supplemented with 10% fetal bovine serum, 2 mM GlutaMAX (Gibco, US), 100 µg/mL penicillin-streptomycin and 5 ng/mL freshly supplemented basic human Fibroblast Growth Factors (FGF) (Peprotech, USA).

Cell Priming

Cells were washed with PBS, and suspended with trypsin-EDTA solution (Sigma, UK). The protein solution was added to the suspended cells in phenol free DMEM, and left to shake and incubate at 37° C. for 15 minutes. The cells were then centrifuged at 500 g for 5 minutes, and the supernatant discarded. The cells were then resuspended for immediate use or to be plated.

Alternatively, a protein solution was applied directly to plated cells. The cells were washed with PBS, and the protein solution added in an appropriate buffer for up to 30 minutes with shaking at 37° C. The cells were then washed with PBS again, and ready for use.

Cell Cytotoxicity Assays

The cytotoxicity of the constructs was assayed using either (3-(4,5-dimethylthiazol-2-yl)-5-(3-carboxymethoxyphenyl)-2-(4-sulfophenyl)-2H-tetrazolium) (MTS) or alamarblue® according to the manufacturers' instructions. Briefly, hMSCs were plated in 96-well plates at a range of concentrations to produce a standard curve. A known quantity of cells was primed with a solution of the construct for 15 minutes then washed with PBS before incubation with either MTS or alamarBlue solution for 1-2 hours. Absorbance or fluorescence values were then collected using a plate reader, and the values compared against the standard curve to determine the percentage survival of primed cells.

UV-Visible and Fluorescence Spectrophotometry

UV-visible and fluorescence spectrophotometry were performed using routine methods.

Bicinchoninic Acid Assay

Bicinchoninic acid assays were performed according to the manufacturer's instructions. Briefly, 20 µL of samples were added to 200 µL of reagents A and B (Thermo Scientific, UK) mixed in a 50:1 ratio in a 96-well plate. The plate was then incubated for 30 minutes at 37° C., before measuring the absorbance at 530 nm using a plate reader. Absorbance values collected for analytes were compared against a standard curve of a protein at known concentrations to calculate the concentration of the analytes.

Sodium Dodecyl Sulfate-Polyacrylamide Gel Electrophoresis (SDS-PAGE)

SDS-PAGE analysis was performed using routine methods. Briefly, analytes were mixed 1:1 with sample application buffer comprising glycerol, SDS, EDTA, Tris, mercaptoethanol and bromophenol blue, and heated to 95° C. for 5 minutes. The samples were then loaded into Novex® 4-20% Tris-glycine pre-cast gels (Thermo Fisher Scientific). A voltage of 200 V was applied for 50 minutes, and the resultant gel stained with Coomassie Blue stain.

Circular Dichroism

Synchrotron-radiation circular dichroism was performed on the B23 beamline at the Diamond Light Source, Oxford. Samples were desalted into chloride-free buffers. Spectra were collected from 185 to 260 nm, using a cuvette with a pathlength of 200 µm. For thermal studies, data were collected from 20 to 90 to 20° C. at 5° C. intervals with 1 minute incubation time. Alternatively, lamp-radiation circular dichroism was performed on a J-1500 CD spectrophotometer (JASCO, Germany), using a 100 µm pathlength cuvette. Data deconvolution was performed using the BeStSel web service. (Micsonai et al. (2015) Proc. Natl. Acad. Sci. U.S.A. 112, E3095-3103).

Fluorescence Microscopy

Confocal microscopy was performed using a Leica TCS SP8 confocal laser scanning fluorescence microscope (Leica Microsystems, Germany), using routine methods. Widefield microscopy was performed using a Leica DMI6000 inverted epifluorescence microscope (Leica Microsystems, Germany), using routine methods. OpdA and thrombin were fluorescently tagged with either 5(6)-carboxyfluorescein N-hydroxysuccinimide (Sigma) or rhodamine N-hydroxysuccinimide (Thermo Scientific, Germany), according to the manufacturer's instructions, whereas scGFP-based constructs are inherently fluorescent. To observe localization of the complexes, proteins were added to cells plated in a glass-bottom dish for 10-30 minutes, washed with PBS, then imaged.

Scanning Electron Microscopy

Bovine articular surface samples were fixed with 2.5% glutaraldehyde for 1 hour, rinsed three times for 10 minutes with 100 mM sodium phosphate buffer pH 7.4, placed in 1% osmium tetroxide for one hour, washed three times for 10 minutes with 100 mM sodium phosphate buffer, then washed with water for 10 minutes. Dehydration steps were made with 25, 50, 70, 80, 90, 96, and 100% ethanol, changing concentration every 10 minutes, and then processed with a critical point dryer. The samples were sputter coated with palladium or chromium and imaged on an FEI field emission scanning electron microscope (Quanta 200).

Proliferation

Proliferation of tissue engineered hMSCs within [cThrombin][S] catalysed fibrin constructs was analysed by comparing the results of MTS assays (described above in 'Cell cytotoxicity assays') performed over time. The effect of priming hMSCs with [scGFP-CshA] and [scGFP-CshA][S] on their proliferation was analysed using a haemocytometer to count cells, and comparing them to their seeding number.

Flow Cytometry hMSCs primed with protein complexes were harvested, washed in an initial wash step, and centrifuged at 1500 RPM for five minutes. The sediment was re-suspended in PBS containing a dead stain. Suspensions containing approximately 1,000,000 cells per mL were transferred to individual flow cytometry tubes, and analysed using a flow cytometer and associated software. The cell suspension was passed through the interrogation point at a rate of 100-300 events per second with a total of 20,000 whole cell events measured. The side scatter area (SSC-A), forward scatter area (FSC-A), forward scatter height (FSC-H), and experiment-specific fluorescence were measured, with unlabelled cells as a control group to define the gated areas used for all samples. The whole cell populations were defined by an FSC-A vs SSC-A gate firstly, with data outside this region excluded as cell debris. Following this, the whole cell populations were gated by FSC-A vs FSC-H defining the single cell populations. The single cell populations were further gated by defining an upper limit on the FSC-A vs the dead stain filter dot plot, and data above this limit were excluded as dead cells. The live cells were gated on a FSC-A vs. FITC-A plot, with data inside the region corresponding to scGFP positive labelled cells and data outside the region corresponding to non-fluorescent cells (priming hMSCs with scGFP-CshA constructs), or were gated on a PE-CF594-A vs. FITC-A plot, with data inside the region corresponding to scGFP positive (Q1 and Q2) and mCherry positive labelled cells (Q2 and Q4), and data outside the region corresponding to non-fluorescent cells (Q3) (cell-surface scGFP-SpyCatcher and mCherry SpyTag reaction). Experiment-specific parameters are given in Table 9.

TABLE 9

Flow cytometry parameters

| Experiment | Initial wash step | Dead staining | Fixing solution | Instrument and software | Filters for measuring fluorescence |
| --- | --- | --- | --- | --- | --- |
| scGFP-CshA priming | Phenol-free DMEM | 0.004 mg/mL Propidium iodide in PBS | No fixing | NovoCyte, NovoExpress | Qdot 605-A (propidium iodide), FITC-A (scGFP) |
| scGFP-SpyCatcher and mCherry-SpyTag cell-surface reaction | Phenol-free DMEM then PBS | 1% (v/v) Zombie NIR in PBS for 15 minutes at room temperature, then washed with PBS and fixed | 1% para-formaldehyde | LSR Fortessa X20, FACSDiva | APC-Cy7-A (Zombie NIR), FITC-A (scGFP), PE-CF594-A (mCherry) |

Cell Membrane Uptake Quantification hMSCs were primed for 15 minutes using protein (e.g. [scGFP-CshA]) and conjugate (e.g. [scGFP-CshA][S]) at a range of concentrations in phenol-free DMEM. The amount of protein bound to cell membranes could be calculated by subtracting the amount of protein in the supernatant, determined using UV-visible spectrophotometry at 487 nm, from the amount of protein added to the cells.

Sedimentation velocity analytical ultracentrifugation (SV-AUC) SV-AUC experiments were performed on a Beckman Optima XL-I (Beckman Coulter, USA) using the UV/Visible absorption system at 280 nm and 487 nm, at 40,000 rpm and at 20° C. using two channel 12 mm Epon centerpieces. Buffer density and viscosity was determined using a Lovis 2000 rolling ball viscometer (Anton Paar, Austria). Sedimentation coefficients (S) were determined using the continuous distribution Lamm equation model (c(S)) and were converted to standard conditions (Sw (20, w)). Molecular weights were calculated directly from integrated c(s) peaks.

Chemical Cationisation Methods

Protein Cationisation

Protein (OpdA pr thrombin) was cationised using a method derived from that described in Armstrong et al. (Nat. Commun. (2015) Jun. 17; 6:7405). Briefly, a solution of protein (OpdA or thrombin) in HEPES buffer was added to pH-neutralised N—N'-dimethyl-1,3-propanediamine (DMPA) at a given ratio, and the solution pH-adjusted with 6M HCl. N-(3-dimethylaminopropyl)-N'-ethylcarbodiimide hydrochloride (EDC) was added either in a single addition or two half additions, and the solution was left to stir, then desalted using buffer exchange with 10K MWCO spin concentrators to end the reaction. Specific experimental parameters for each protein are presented in Table 10. Performing the method as reported by Armstrong et al. would lead to severe loss of enzyme activity, as the cationisation reaction leads to inactivation over time. The inventors have determined that either limiting the reaction time or performing size exclusion chromatography on the crude cationisation solution produces active enzyme.

[cOpdA][S] Membrane Activity Assay

3',6'-bis(diphenylphosphinyl) fluorescein (DPPF) was synthesised as a substrate for fluorescence imaging as described by Liguo An et al. (Chem. Eur. J. (2007), Feb. 2; 13:1411). DPPF was dissolved in DMSO to a stock concentration of 100 mM, and applied to cells at a final concentration of 1 mM for 30 minutes. Cells plated on glass bottom microwell dishes were labelled with 12 μM [cOpdA][S] after DPPF exposure. Images were collected using confocal microscopy. Acetylthiocholine was also used to assay the activity of membrane-bound [cOpdA][S] over 5 days. 450 μM acetylthiocholine and 300 μM 5,5'-dithiobis-(2-nitrobenzoic acid) was applied to hMSCs and hMSCs primed with 10 μM [cOpdA][S] plated in a 96-well plate at day 0, 1, and 5. The resulting absorbance was read at 412 nm over time, and an extinction coefficient of 14150 $M^{-1} \cdot cm^{-1}$ was used to calculate acetylthiocholine turnover from the initial rate.

TABLE 10

Cationisation parameters.

| Protein | Buffer | Ration DMPA:anionic sites | Ratio EDC:anionic sites | Reaction pH | Reaction time | Reaction temp. | Purification |
|---|---|---|---|---|---|---|---|
| OpdA | 30 mM HEPES, 100 μM CoCl$_2$ | 300:1 | 50:1 | 5.1 | 24 hours | 4° C. | Size exclusion chromatography |
| Thrombin | 60 mM HEPES | 150:1 | 34:1 | 6.5 | 1 hour | Room temp. | None |

Recombinant Preparation of Supercharged Proteins

Preparing Supercharged Fusion Proteins

Supercharged GFP was as described in Lawrence et al. (J. Am. Chem. Soc. (2007) vol. 129 p. 10110-10112). For preparation of scGFP fusion proteins with the fibronectin-binding portion of CshA (SEQ ID NO:19), OpdA (SEQ ID NO:20), PlGF-2$_{(123-144)}$ (SEQ ID NO:21) and SpyCatcher (SEQ ID NO:23), a linker region was designed as outlined below. Subsequent steps were carried out as described above in the section headed "Plasmid preparation".

Linker Design

The linking regions used to form the fusion proteins were designed using methods outlined in Chen et al. (Adv. Drug. Deliv. Rev. (2013) Sep. 29; 65,1357-69).

Supercharging OpdA

OpdA was supercharged to form scOpdA by mutation of 11 aspartic/glutamic acid residues to lysine residues, listed in Table 11 below (position numbering with reference to SEQ ID NO:10). The gene with mutated residues was ordered from Eurofins Genomics (Germany).

OpdA Neutron Reflectometry

Neutron reflectometry was performed on the INTER beamline at the Isis facility, Oxford, and on the D17 beamline at the Institut Laue-Langevin, Grenoble. Floating bilayers of 4:1 2-oleoyl-1-palmitoyl-sn-glycero-3-phosphocholine (POPC) and 1-palmitoyl-2-oleoyl-sn-glycero-3-phospho-(1'-rac-glycerol) (POPG) were assembled on a silicon block with a 1-Palmitoyl-2-[16-(acryloyloxy)hexadecanoyl]-sn-glycero-3-phosphorylcholine (al-PC) monolayer covalently bound to the silicon substrate using the Langmuir-Blodgett trough deposition method. OpdA constructs were loaded at concentrations of 0.2 and 5 μM, and loosely bound material washed with buffer. Data deconvolution was performed with the RasCal software package for MATLAB.

cThrombin Fibrin Formation

Thrombin-catalysed fibrin formation was measured through absorbance at 600 nm during the cationisation process. Briefly, 75 μL of 0.06 mg/mL thrombin was added to 125 μL of 5 mg/mL fibrinogen, shaken for 20 seconds, and the absorbance at 600 nm measured over time.

Fibrin Constructs Catalysed by Membrane-Bound [cThrombin][S]

[cThrombin][S]-primed hMSCs were added to a solution of 7.5 mg/mL human fibrinogen in wells precoated with agarose. Successful fibrin formation could be analysed using confocal microscopy with Alexa-594 tagged fibrinogen.

Solution Coupling of SpyCatcher and SpyTag Constructs

TABLE 11

Mutations made to OpdA to produce scOpdA
scOpdA modifications

| D76K | D97K | D109K | E120K | E121K | E135K | D136K | D184K | D211K | D212K | E239K |
|---|---|---|---|---|---|---|---|---|---|---|

Protein-Specific Assays

Paraoxon Hydrolysis

Proteins (OpdA-based constructs) were diluted to a working concentration in buffer. 100× paraoxon stocks were prepared in isopropanol. Formation of 4-nitrophenolate was measured at 405 nm, using an empirically determined extinction coefficient of $\varepsilon_{405}$=12013 $M^{-1} \cdot cm^{-1}$. Non-linear regression was performed on initial-rate data to determine the Michaelis-Menten parameters.

The coupling of [scGFP-SpyCatcher] or [scGFP-Spy-Catcher][S] with either [mCherry-SpyTag] or [CshA-SpyTag] was investigated using SDS-PAGE. Equal volumes of either [scGFP_SpyCatcher] or [scGFP_SpyCatcher][S] and [mCherry_SpyTag] or [CshA_SpyTag] were mixed in a glass vial and agitated using a magnetic stirrer. At predetermined time points throughout the reaction, 10 uL of the resulting solution was removed and mixed with an equal volume of SDS sample application buffer for 5 minutes. The range of samples obtained in this method were applied to SDS-PAGE gels as previously described before subsequent staining and destaining.

Static Adhesion Assay for scGFP-CshA and scGFP-PIGF$_{(123-144)}$

Cell-substrate adhesion was investigated using a CyQUANT® NF cell proliferation assay kit (Invitrogen, UK). Human fibronectin (Sigma Aldrich) was diluted to 10 μg/mL with PBS, collagen I (rat tail; Sigma Aldrich) and collagen II (bovine trachea; Sigma Aldrich) were diluted to 0.2 mg/mL. 100 μL of these solutions were used to coat each well of the non-tissue-culture-treated 96 well plate. The plates were then washed three times with PBS solution containing 10 mg/mL bovine serum albumin (BSA; Sigma Aldrich) to block the non-specific interactions. The wells treated with BSA were used as a control. Cells were primed with protein complexes and the cells were harvested and counted using a haemocytometer. Standard curve samples were established in expansion medium. After four hours of incubation, medium was removed from cells by gentle aspiration and 100 μL of dye binding solution was dispensed into each well. The plate was covered and incubated at 37° C. for 1 hour. The fluorescence intensity of each sample was measured using a plate reader with excitation at 485 nm and emission detection at 530 nm. Adhesive cell numbers were compared to control samples of untreated cells incubated with phenol-free DMEM.

Flow Adhesion Assay

Dynamic cell adhesion experiments were carried out with an ExiGo microfluidics pump (Cellix Ltd flowing through a Vena8 Fluoro+ biochip. The chip was coated overnight with 0.1 mg/mL collagen II (Sigma Aldrich) and unspecific sites were blocked with 10 μg/mL BSA (Sigma Aldrich). The channel was washed with phenol-free DMEM with no additives for 30 seconds at 40 μL/min. scGFP-PIGF$_{(123-144)}$-primed and [scGFP-PIGF$_{(123-144)}$][S]-primed hMSCs were resuspended at a density of 1 million cells per mL in phenol-free DMEM without additives. A 50 μL aliquot was added to the channel reservoir each time and the cells were withdrawn at flow rates of 6, 4, or 3 mL/minute.

Adhesion to Bovine Articular Cartilage Explants

Cartilage explants were harvested form the lateral and patellar groove of 6-8-week old calves, obtained 6-8 hours after death. The disks were delimited with an 8 mm biopsy punch and carefully detached with a surgical scalpel (size 22; Swann Morton). After dissection, the pieces were kept in DMEM with 10% FBS, 100 μg/mL penicillin-streptomycin. Cartilage discs were cut to 6 mm diameter with a biopsy punch and placed in a non-tissue culture treated 96 well plate (Fisher, UK) with 200 uL of phenol-free DMEM without supplements. Cells were primed with either scGFP-PIGF$_{(123-144)}$ or the corresponding conjugate and resuspended in phenol-free DMEM. Cells were added onto the cartilage and placed in incubator at 37° C. with 5% CO2 for 4 hours. The samples were then fixed for SEM imaging or histology analysis.

In Vivo Transplantation of scGFP-CshA-Primed hMSCs in Mice

Male 20-week-old FVB/N and BALB/c nude mice were purchased from the Animal Resource Centre (Perth, Western Australia). All animal procedures were approved by the Animal Ethics Committee of the University of Queensland and were carried out in accordance with Australian Code for the Care and Use of Animals for Scientific Purposes 8th edition. Mice were anaesthetized with isoflurane. Body temperature was controlled by placing mice on a heating pad set to 37° C. 150 μL of a suspension of [scGFP-CshA][S], 2×10$^6$ untreated hMSCs, or [scGFP-CshA][S] modified hMSCs was injected with a 27 gauge needle either through a tail vein (intravenous injection) or through the chest wall into the left ventricle (intracardiac injection), respectively. Prior to the injection, the hMSCs were maintained at 4° C., and the cells were gently resuspended with a pipette to ensure no aggregation before the injection. The mice were sacrificed at 2 hours and 24 hours after the injection. Genomic DNA of the heart and lung were isolated using DNA Mini Kit (Qiagen, USA) and primers targeting the human Alu sequence according to the manufacturer's instructions. Droplet digital PCR (ddPCR) was then used to quantify the number of human cells in each tissue. Briefly, 20 μL of ddPCR reaction mix was separated into droplets with a QX200 Droplet Generator (BioRad, USA). The droplets were transferred into a 96-well PCR plate, sealed and incubated at following cycling conditions: one cycle of 95° C. for 5 minutes, 45 cycles of 95° C. for 30 seconds, 55° C. for 1 minute and one cycle of 4° C. for 5 minutes, 90° C. for 5 minutes and an infinite hold of 12° C. After thermal cycling, the PCR plate was transferred in QX200 Droplet Reader (read) and read in the FAM channel using QuantaSoft version 1.7.

Results

Protein Expression and Purification

Figure 5:
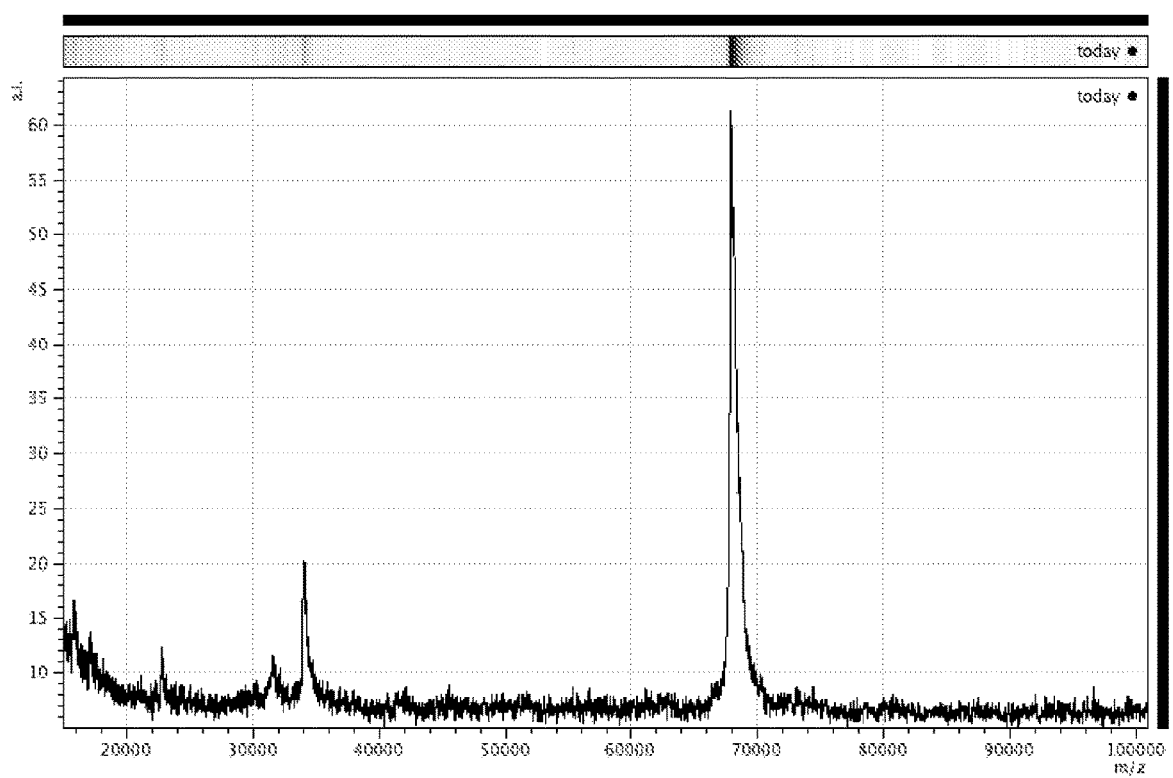
FIG. 5 shows the mass spectrum of scGFP-OpdA.
Figure 6:
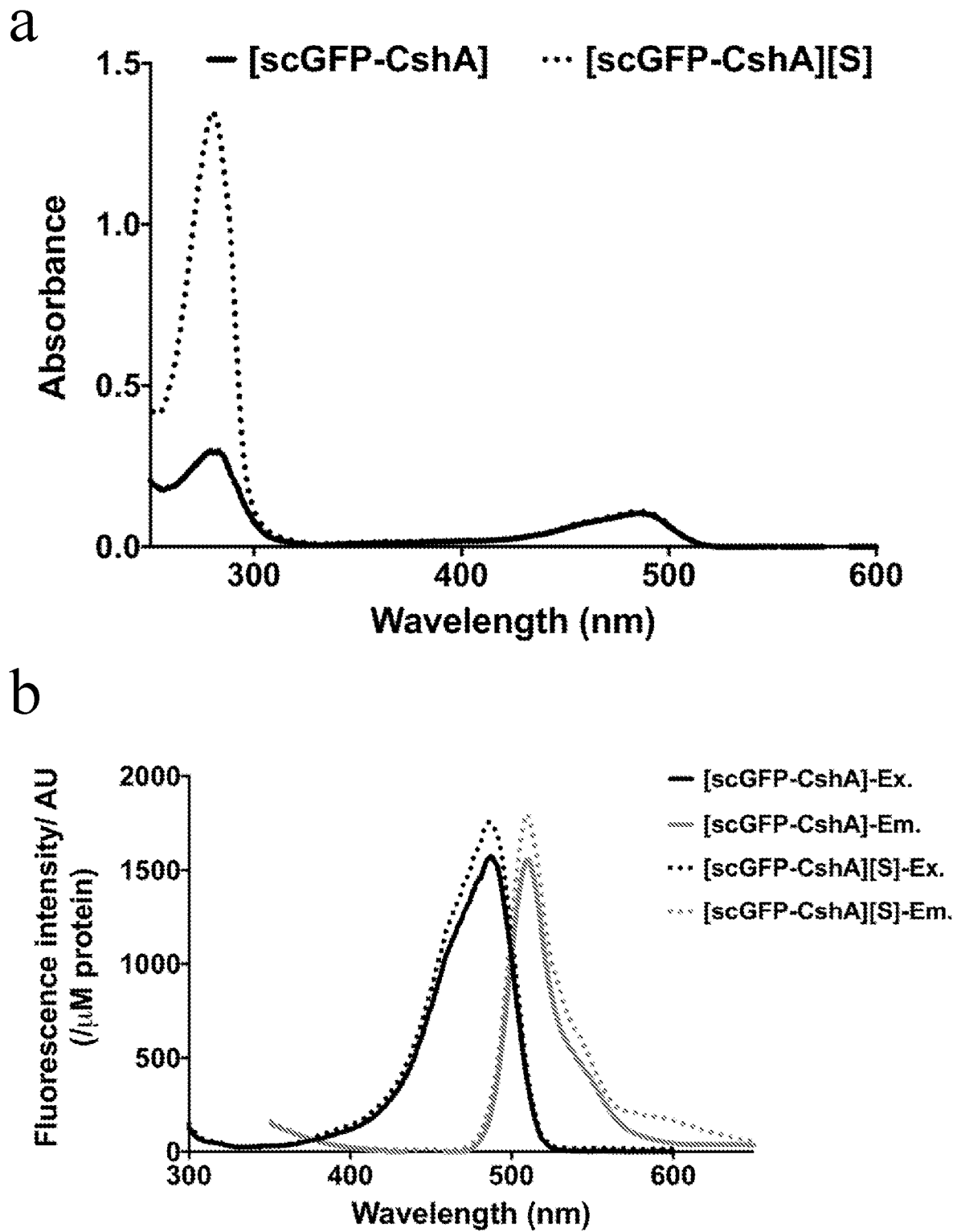
FIG. 6 shows (a) the UV-vis absorbance of [scGFP-CshA] and [scGFP-CshA][S] and (b) the fluorescence excitation and emission of [scGFP-CshA] and [scGFP-CshA][S]
Figure 7:
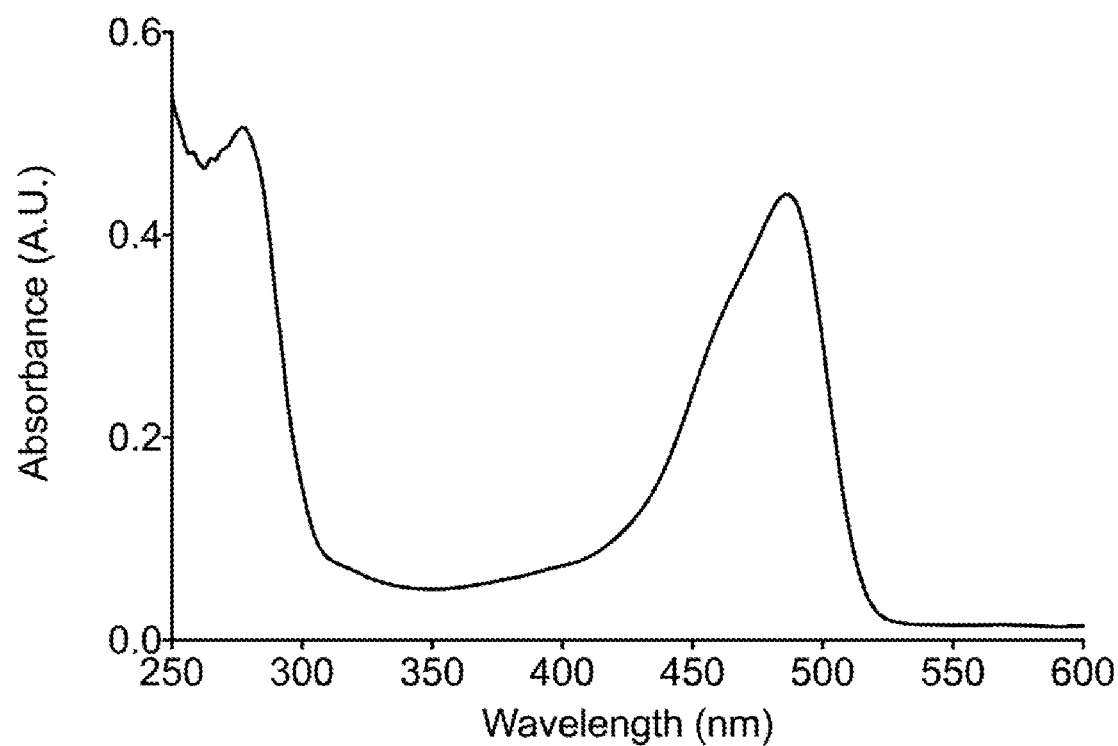
FIG. 7 shows UV-vis absorbance of scGFP-OpdA.
Figure 8:
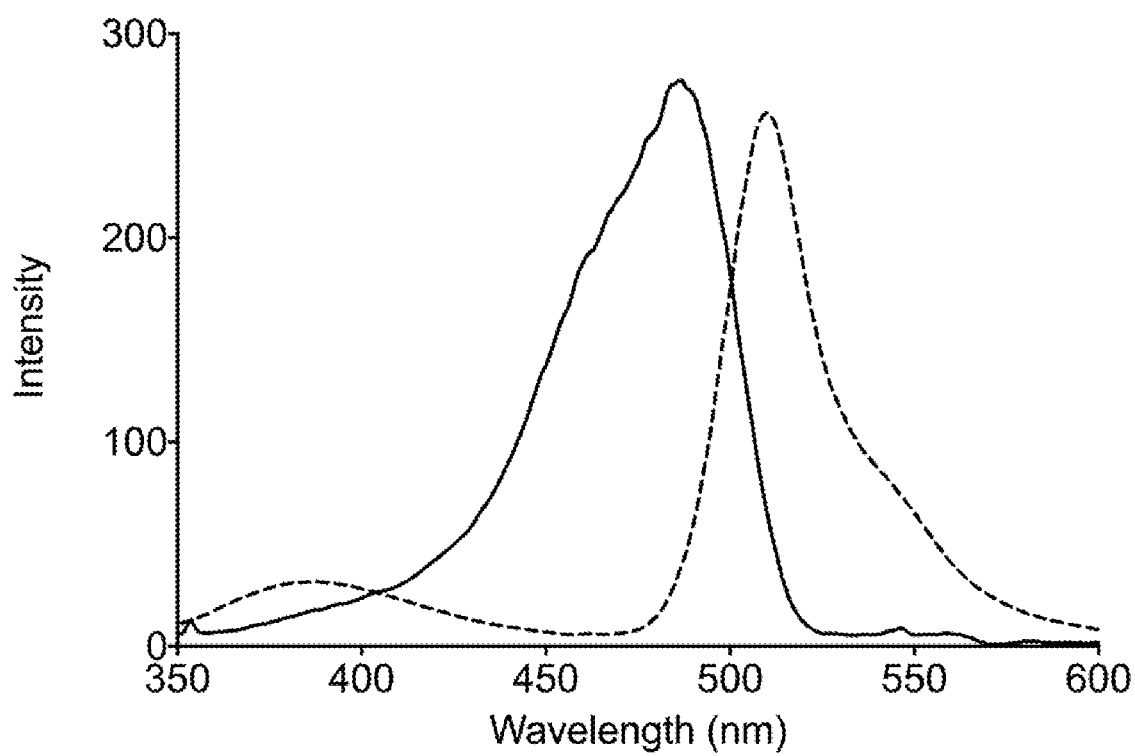
FIG. 8 shows excitation and emission properties of scGFP-OpdA.

All proteins were confirmed to be expressed and purified using SDS-PAGE, mass spectrometry (MADLI-TOF), and activity assays. The mass spectrum for scGFP-OpdA is shown in FIG. 5. UV-visible spectrophotometry and fluorescence spectrophotometry confirmed the correct folding of the scGFP-fusion constructs (FIGS. 6-8).

Cationisation

Figure 9:
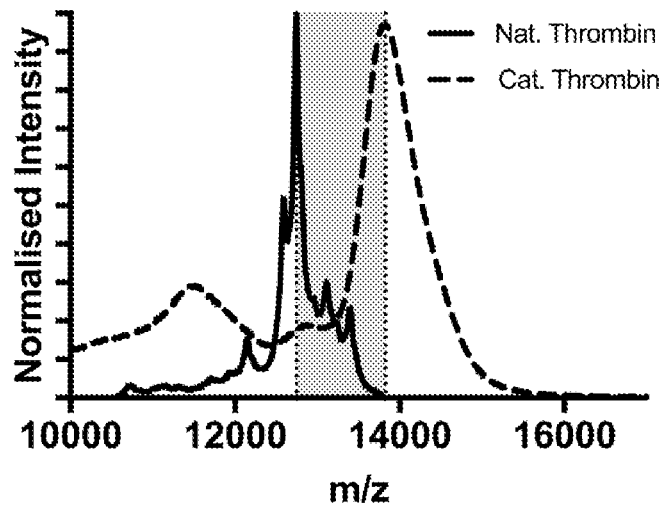
FIG. 9 shows mass spectra of thrombin and cationised thrombin at a charge number of 3.

The successful cationisation of OpdA and thrombin was confirmed using matrix-assisted laser-desorption-ionisation time-of-flight mass spectrometry (MALDI-TOF). OpdA was shown to increase in mass by approximately 1700 Da, corresponding to the addition of 20 DMPA molecules. Thrombin cationisation led to an increase in mass of approximately 3300 Da, equivalent to 39 DMPA molecules. The mass spectra collected at a charge number of 3 for thrombin are shown in FIG. 9.

Zeta potentiometry was used to show the increased charge associated with cationisation. Cationisation increased the zeta potential of OpdA from −7 mV to +21 mV (see FIG. 10). The change in zeta potential during cationisation of thrombin is shown in FIG. 11.

Figure 12:
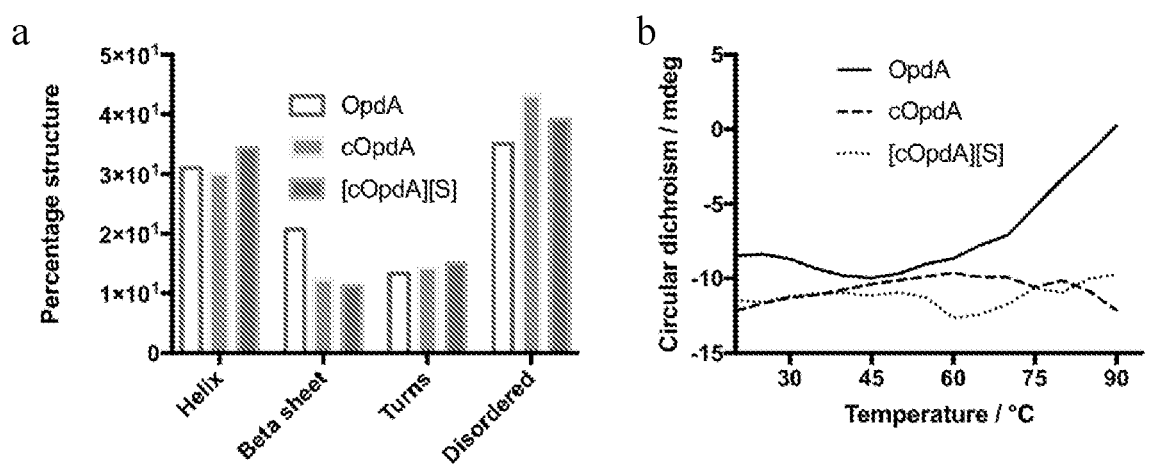
FIG. 12 shows (a) the secondary structure composition of OpdA, cOpdA, and [cOpdA][S], and (b) the thermal denaturation of OpdA, cOpdA, and [cOpdA][S]
Figure 13:
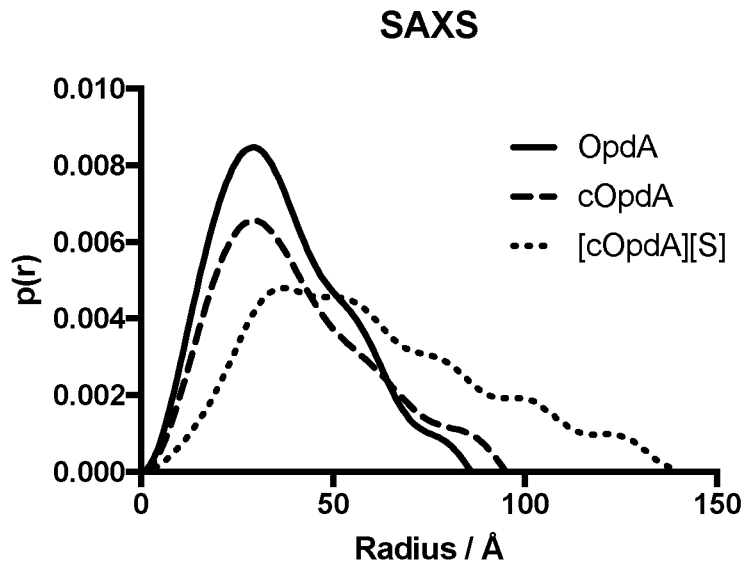
FIG. 13 shows the radial probability distribution of OpdA, cOpdA, and [cOpdA][S]

Structural changes associated with cationisation were assayed using dynamic light scattering (DLS), circular dichroism (CD), and small angle X-ray scattering (SAXS). DLS showed the cationisation of OpdA lead to an increase in size of 0.8 nm corresponding to the addition of DMPA molecules to surface residues, whilst CD showed minimal changes in secondary structure but an increase in thermal stability (FIG. 12). SAXS showed OpdA remained dimeric post-cationisation (FIG. 13).

Conjugation

Figure 10:
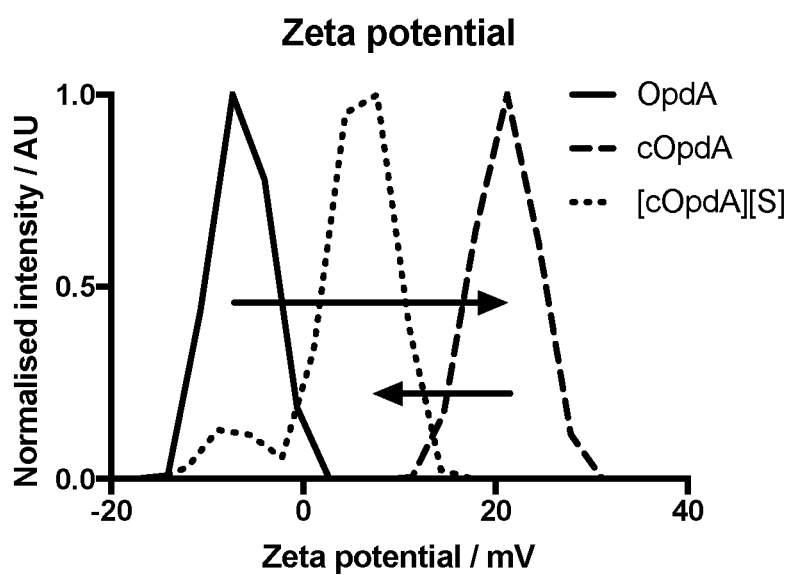
FIG. 10 shows the zeta potentiometries of OpdA, cOpdA and [cOpdA][S]
Figure 11:
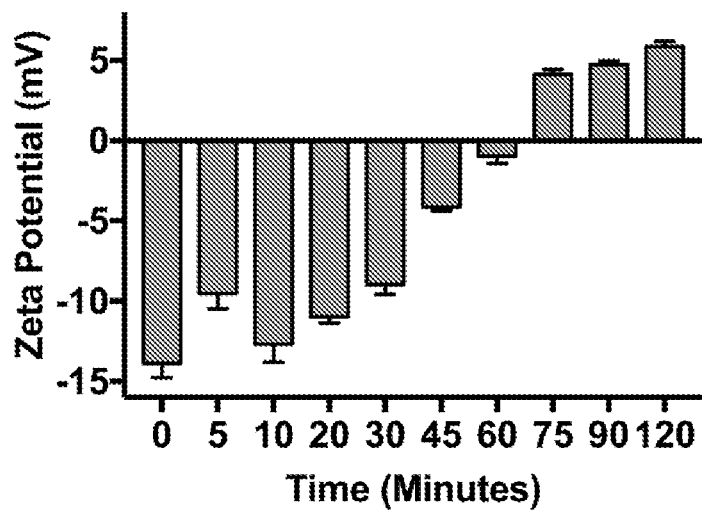
FIG. 11 shows the change in zeta potential over time during cationisation of thrombin.

Electrostatic grafting of the anionic headgroup of the surfactant to positively charged residues leads to a decrease in the surface charge of proteins, therefore the zeta potential is expected to decrease. scGFP-PIGF$_{(123-144)}$ was shown to have a zeta potential of +22 mV, while [scGFP-PIGF$_{(123-144)}$][S] was −0.5 mV. scGFP-CshA had a zeta potential of +1 mV despite the highly anionic CshA region, and [scGFP-CshA][S] was −15 mV. cOpdA to [cOpdA][S] showed a reduction of 13 mV (FIG. 10).

An increase in size corresponding to the addition of a surfactant corona is also expected. DLS showed an increase in hydrodynamic diameter of 1.9 nm, 2 nm and 2.9 nm for the conjugation of cOpdA, scGFP-CshA and scGFP-PIGF$_{(123-144)}$, respectively. scGFP-OpdA showed a 388 nm increase in size due to the formation of clusters. SV-AUC showed an increase in the sedimentation coefficient of [scGFP-CshA][S] from 4.1 to 4.8, indicating surfactant binding.

Figure 14:
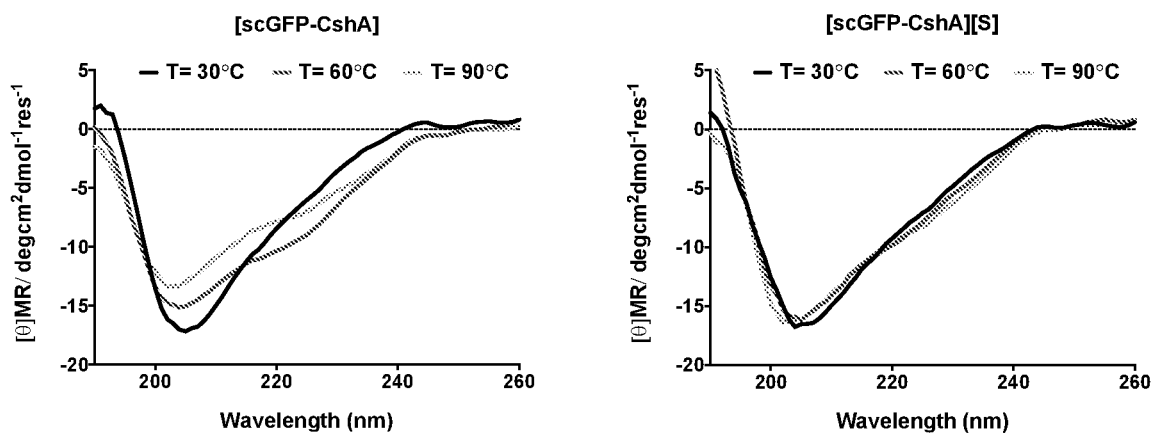
FIG. 14 shows (a) the circular dichroism of scGFP-CshA and (b) [scGFP-CshA][S] at 30, 60 and 90° C.
Figure 15:
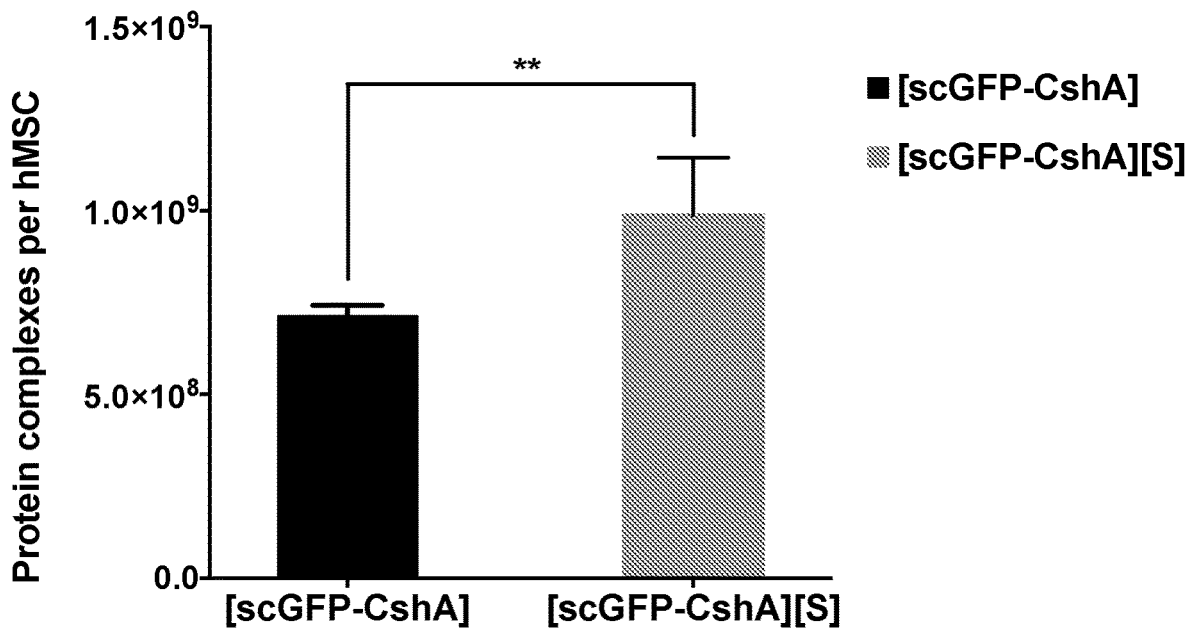
FIG. 15 shows the number of scGFP-CshA and [scGFP-CshA][S] molecules bound per hMSC.
Figure 16:
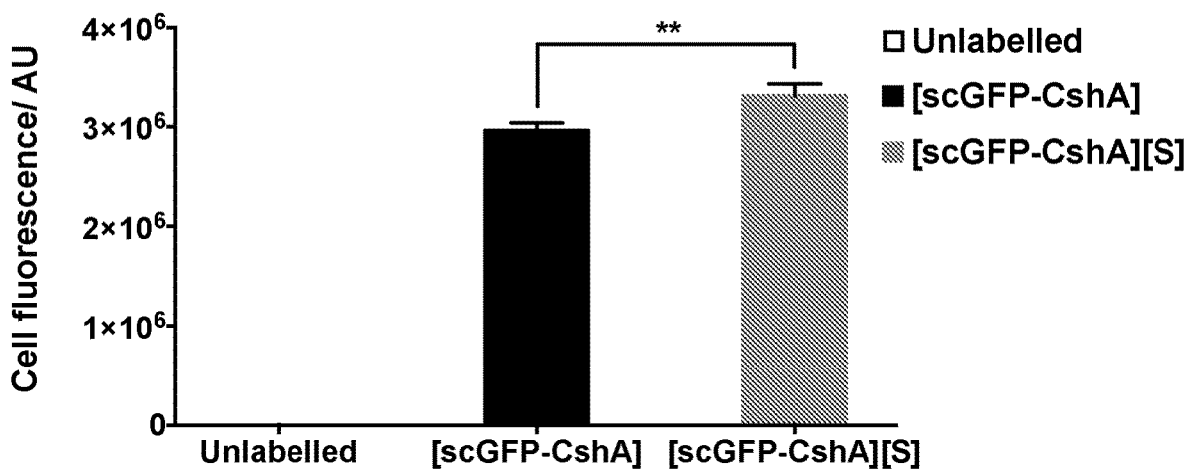
FIG. 16 shows the fluorescence of the primed hMSCs.
Figure 17:
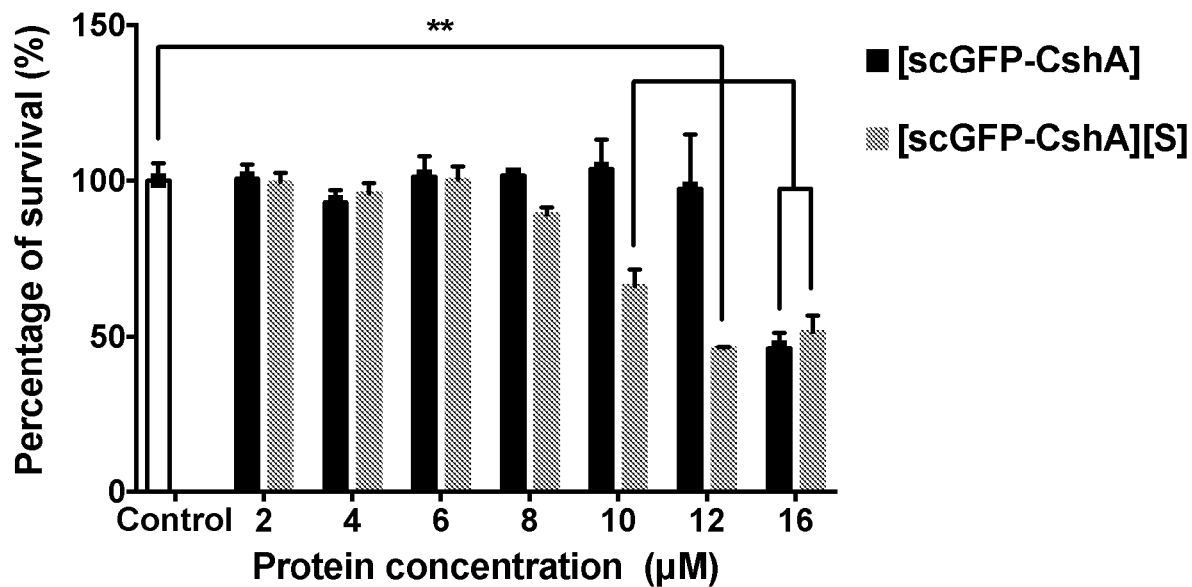
FIG. 17 shows the cytotoxicity of scGFP-CshA and [scGFP-CshA][S]
Figure 18:
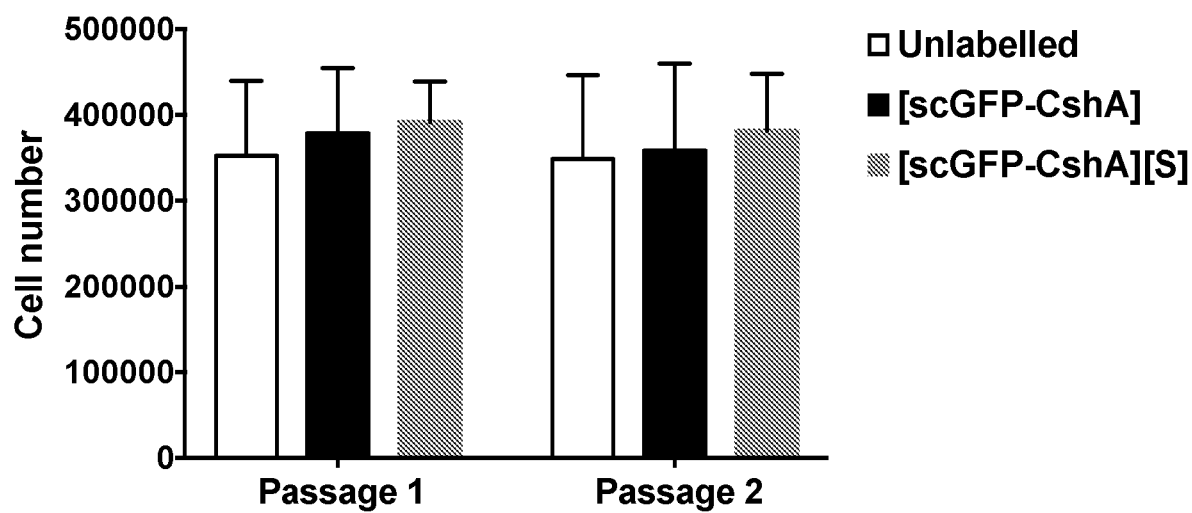
FIG. 18 shows the proliferation of hMSCs primed with [scGFP_CshA] and [scGFP_CshA][S]
Figure 19:
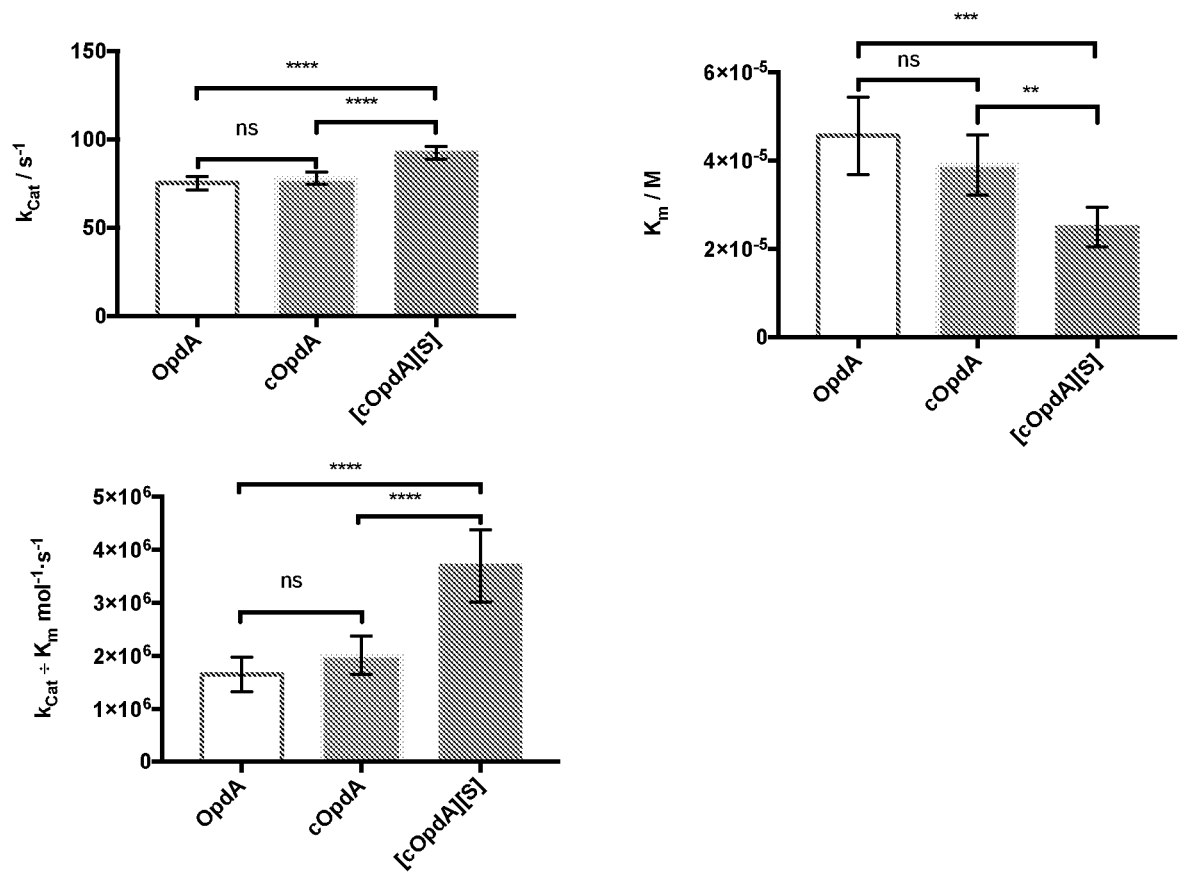
FIG. 19 shows the Michaelis-Menten parameters of OpdA, cOpdA, and [cOpdA][S]
Figure 20:
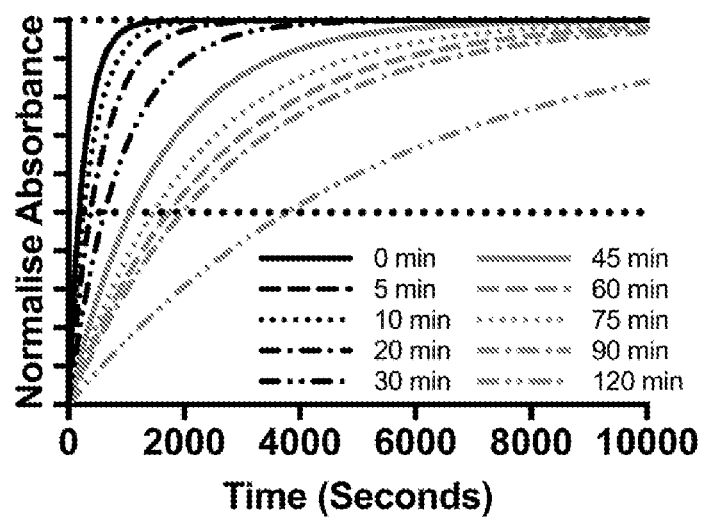
FIG. 20 shows the change in enzymatic activity over time during cationisation of thrombin.

Importantly, surfactant conjugation did not lead to denaturation. CD was used to assess the secondary structures of OpdA and scGFP-OpdA constructs. [cOpdA][S] showed minimal changes in secondary structure to each of OpdA and cOpdA, and retained the improved thermal stability of cOpdA (FIG. 12). Conjugation of scGFP-OpdA lead to an increase in thermal stability (FIG. 14). UV-visible spectrophotometry and fluorescence spectrophotometry confirmed that the fluorophore's structure was maintained (FIG. 6).

Cell Loading

The successful loading of the conjugate systems to membranes was confirmed through microscopy, spectrophotometry, flow cytometry, reflectometry and activity assays.

The scGFP-based constructs are inherently fluorescent, and so were simply visualised using fluorescence microscopy. scGFP-CshA, [scGFP-CshA][S], scGFP-PIGF$_{(123-144)}$, [scGFP-PIGF$_{(123-144)}$][S], scGFP-OpdA, and [scGFP-OpdA][S]-primed cells all displayed fluorescent membranes, but the conjugate species retained the membrane fluorescence for a longer time period: approximately 15 minutes for unconjugated protein versus more than 24 hours for conjugated protein, indicating that the unconjugated proteins are rapidly endocytosed, whilst conjugated protein is retained at the membrane.

Thrombin and OpdA each had to be fluorescently tagged prior to imaging, as described in 'Microscopy' method section. cOpdA was rapidly internalised, whereas [cOpdA][S] remained at the cell membrane. [cThrombin][S] was observed at the cell membrane for up to 7 days. Native OpdA and thrombin did not interact with cells.

UV-visible spectrophotometry may be used to determine the amount of protein bound to cell membranes. Approximately 0.7 billion scGFP-CshA complexes bound per cell, whereas 1 billion [scGFP-CshA][S] complexes bound per cell, after 15 minutes (FIG. 15). Similarly, flow cytometry showed significantly greater fluorescence for [scGFP-CshA][S]-loaded cells versus scGFP-CshA-loaded cells (FIG. 16). The amount of scGFP-CshA observable per cell is significantly reduced after longer time periods compared to the amount of [scGFP-CshA][S], due to rapid endocytosis of the unconjugated protein.

Neutron reflectometry was used to assess the insertion of [cOpdA][S] into a model membrane. [cOpdA][S] was shown to insert into the lipid bilayer and, once the membrane was saturated with conjugate, forms a layer above the membrane. cOpdA penetrated the bilayer and disrupted the supporting monolayer, indicating that it was not embedded within the membrane.

Importantly, the cells could be treated with each protein construct without significant cell cytotoxicity. The surfactant, glycolic acid ethoxylate 4-nonylphenyl ether, was also assayed. The maximum assayed loading concentrations below significant cytotoxicity are presented in Table 12 below. Asterisks mark the data where significant cytotoxicity was not observed. The data for scGFP-CshA and [scGFP-CshA][S] are shown in FIG. 17.

Primed cells were also shown to proliferate readily. [cThrombin][S]-primed cells were shown to proliferate via an MTS assay over 22 days (FIG. 11). scGFP-CshA and [scGFP-CshA][S]-primed cells proliferated at the same rate as unprimed cells, as confirmed by direct cell counting (FIG. 18), indicating that process of priming the cells with the priming entity (scGFP-CshA or [scGFP-CshA][S]) had no impact on the ability of cells to proliferate.

The differentiation potential of cells was also not affected by priming. [cThrombin][S]-primed cells treated with adipogenic or osteogenic media displayed characteristic fat droplets and extracellular calcium deposits, respectively, after 21 days, as observed with widefield microscopy.

TABLE 12

Maximum loading concentrations for the conjugated proteins;
* indicates significant cytotoxicity was not observed

| Protein | Maximum assayed loading concentration below significant cytotoxicity | Assay method |
|---|---|---|
| [cOpdA][S] | 15 μM | alamarBlue |
| [cThrombin][S] | 5.2 μM | MTS |
| [scGFP-CshA][S] | 8 μM | MTS |
| [scGFP-PIGF$_{(123-144)}$][S] | 12 μM | MTS |
| [scGFP-SpyCatcher][S] | 14 μM | MTS |
| mCherry-SpyTag | 14 μM | MTS |
| [scGFP-SpyCatcher][S]-[mCherry-SpyTag] | 14 μM | MTS |
| Glycolic acid ethoxylate 4-nonylphenyl ether | 25 mM* | MTS |

Solution Activity of Constructs

Post-modification, each protein maintained activity. Previous work by Brogan et al. (Nat. Commun. (2014) Oct. 10; 5:5058) with lipases from *Rhizomucor miehei* and *Thermomyces lanuginosus* reported a 98% and 85% reduction in substrate-turnover rate post-cationisation, and a further 55% and 40% reduction post-conjugation, respectively, therefore it is surprising that the inventors were able to maintain activity. The assays required to determine activity are specific to each protein.

OpdA-based constructs were assayed for activity by measuring the hydrolysis rates of paraoxon. The Michaelis-Menten parameters of cOpdA were not significantly different to those of OpdA, however the $K_M$ was significantly decreased (25.0±4.49 vs. 45.6±8.80 μM) and the $k_{cat}$ significantly increased (92.4±3.63 vs. 75.4±3.68 s-1) for [cOpdA][S], leading to a 2.2-fold increase in the specificity constant (FIG. 19). scGFP-OpdA was shown to have a $K_M$ of 31 μM, and a $k_{cat}$ of 1.98 $s^{-1}$.

The activity of thrombin was assayed by measuring the absorbance at 600 nm corresponding to fibrin formation from fibrinogen cleavage. During cationisation, the activity of thrombin was retained up to 120 minutes of cationisation, although the activity was gradually decreased with increased cationisation duration, as shown in FIG. 20.

The coupling of scGFP-SpyCatcher and [scGFP-SpyCatcher][S] to either mCherry-SpyTag or CshA-SpyTag was assayed using SDS-PAGE. The appearance of a band at a high molecular weight indicated the formation of the isopeptide bond between the SpyTag and SpyCatcher moieties, in each of the conjugated and non-conjugated samples, for each of the SpyTag constructs.

Membrane Activity of Constructs

The activity of [cOpdA][S] at cell membranes was followed via microscopy. Cells exposed to DPPF for 30 minutes then treated with [cOpdA][S] exhibited increased fluorescence at cell membranes. Furthermore, hMSCs primed with [cOpdA][S] were able to turn over more acetylthiocholine than unprimed cells over at least 5 days.

Figure 21:
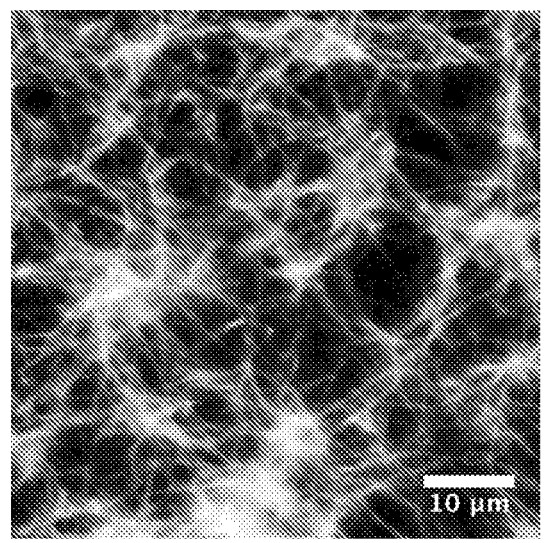
FIG. 21 shows a confocal micrograph of [Thrombin][S]-catalysed fibrin gel.
Figure 22:
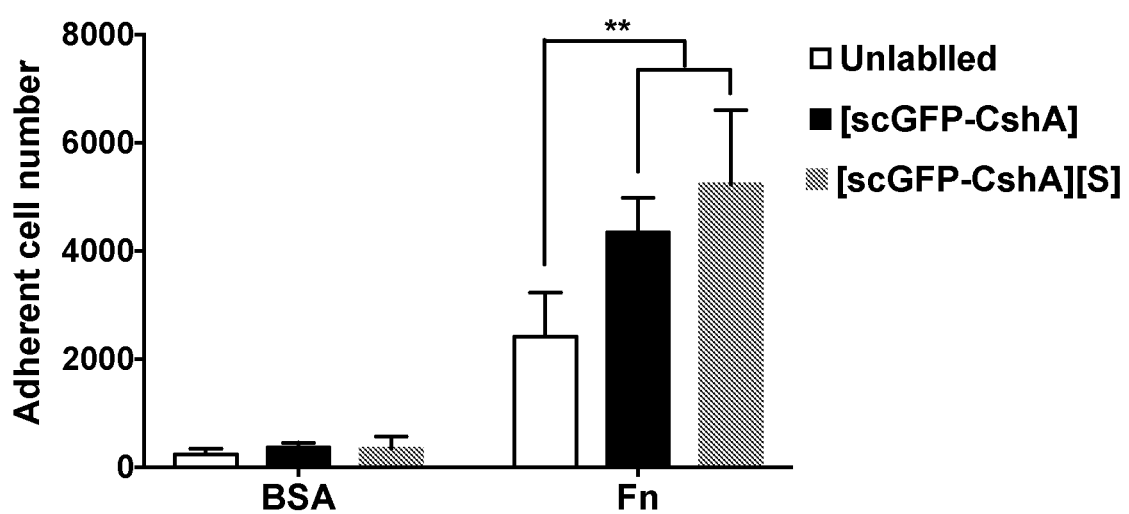
FIG. 22 shows the cell adherence of unlabelled hMSCs, scGFP-CshA primed hMSCs and [scGFP-CshA][S] primed hMSCs on BSA-coated and Fn-coated plates.

[cThrombin][S] bound to cell membranes was able to cleave fibrinogen to form a fibrin gel, as confirmed with confocal microscopy, using Alexa-594-tagged fibrinogen (FIG. 21).

scGFP-CshA, scGFP-PIGF$_{(123-144)}$, and their respective conjugates were assayed for their ability to bind to fibronectin (scGFP-CshA and scGFP-PIGF$_{(123-144)}$) and collagen I and II (scGFP-PIGF$_{(123-144)}$). scGFP-CshA-primed cells and [scGFP-CshA][S]-primed cells adhered in significantly greater numbers than unlabelled cells to fibronectin-treated plates (FIG. 22). Under 4 mL/min flow, hMSCs primed with [scGFP-PIGF$_{(123-144)}$][S] adhered in significantly greater numbers to collagen II than unprimed hMSCs, as observed via widefield microscopy.

Flow cytometry showed that hMSCs primed with scGFP-SpyCatcher or its corresponding conjugate were able to form covalent bonds with mCherry-SpyTag for up to 72 hours.

Figure 23:
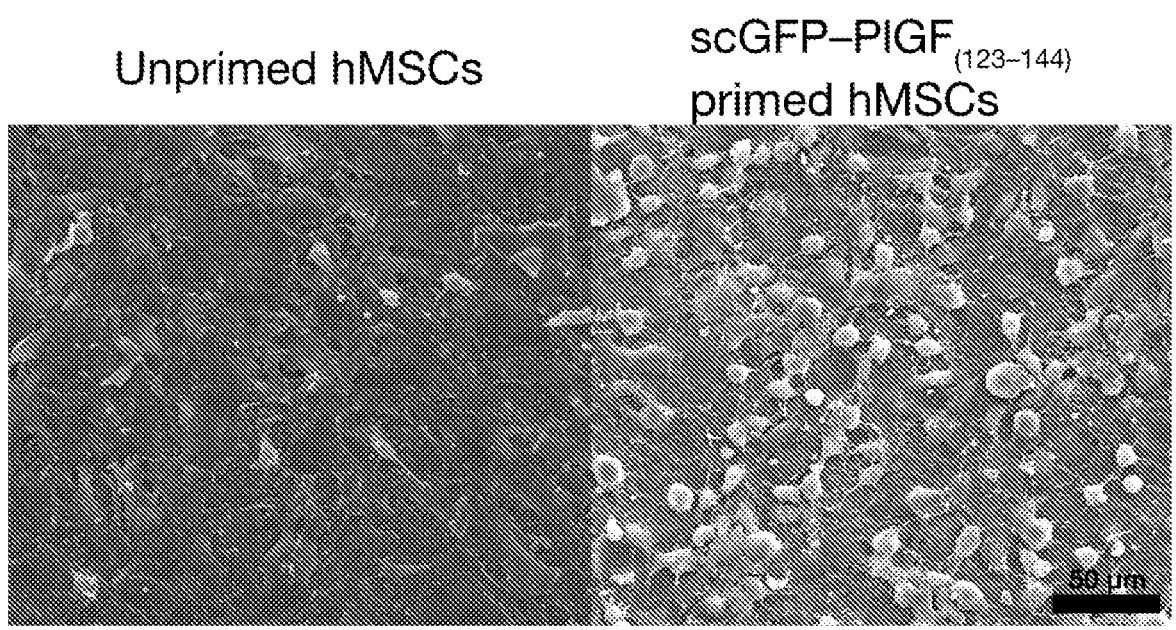
FIG. 23 shows scanning electron microscopy images of explanted bovine articular cartilage with hMSCs and scGFP-PIGF$_{(123-144)}$-primed hMSCs.

[scGFP-PIGF$_{(123-144)}$][S]-primed hMSCs were seen to adhere in greater numbers to explanted bovine articular cartilage than unprimed hMSCs, as seen in FIG. 23.

In Vivo Activity of Constructs

[scGFP-CshA][S]-primed hMSCs were transplanted into mice via intravenous and intracardiac injection. Upon harvesting the heart and lung tissue from the mice after 2 hours, 24 hours, and 4 weeks, the number of hMSCs in each tissue was determined using droplet digital PCR. The tissue:plasma distribution coefficient of [scGFP-CshA][S]-primed hMSCs in the heart was shown to have increased 2-fold relative to unprimed hMSCs at 2 hours and 24 hours.

The invention claimed is:

1. A phospholipid bilayer or micelle comprising at least one embedded protein-polymer surfactant conjugate comprising an anchor protein conjugated to a surfactant,
   wherein the anchor protein is a cationised protein or an anionised protein,
   wherein the at least one protein-polymer surfactant conjugate is embedded within the phospholipid bilayer or micelle; and
   wherein the anchor protein is a protein which does not comprise a —$CH_2C(O)NCH_3(CH_2)_3N(CH_3)_2H^+$ linker covalently bonded to an amino acid side chain.

2. The phospholipid bilayer or micelle according to claim 1, wherein the protein-polymer surfactant conjugate comprises a surfactant containing polyethylene glycol.

3. The phospholipid bilayer or micelle of claim 1, wherein the anchor protein is linked to a secondary molecule which is CshA, a portion of CshA comprising the fibronectin-binding portion of CshA (SEQ ID NO: 19) or is a functional variant having at least 90% sequence identity to SEQ ID NO:19.

4. The phospholipid bilayer or micelle according to claim 1, wherein the anchor protein is an enzyme.

5. A cell comprising a phospholipid bilayer according to claim 1 in its cell membrane.

6. The cell of claim 5, wherein the cell is a mesenchymal stem cell or a cardiomyocyte.

7. A pharmaceutical composition comprising the phospholipid bilayer or micelle according to claim 1, and further comprising a pharmaceutically acceptable carrier, diluent or vehicle.

8. A surgical composition comprising the phospholipid bilayer or micelle according to claim 1 and at least one surgically acceptable carrier, diluent or vehicle.

9. A tissue engineering scaffold comprising the phospholipid bilayer or micelle according to claim 1.

10. A polypeptide comprising:
    a) SEQ ID NOS: 11 or 40 or a functional variant having at least 97% sequence identity with SEQ ID NOS: 11 or 40;
    b) a fusion protein of a supercharged GFP and OpdA (SEQ ID NO: 13) or a functional variant having at least 60% sequence identity with SEQ ID NO: 13;
    c) a fusion protein of a supercharged GFP and SEQ ID NO: 14 or a functional variant having at least 80% sequence identity with SEQ ID NO: 14;
    d) a fusion protein of a supercharged GFP and P1GF$_{(123-144)}$ (SEQ ID NO: 15) or a functional variant having at least 93% sequence identity with SEQ ID NO: 15; or
    e) a fusion protein of a supercharged GFP and any of SEQ ID NOs: 19-39; or a supercharged GFP and a functional variant of any of SEQ ID NOs: 19-39 having at least 60% sequence identity thereto.

11. A polynucleotide encoding a polypeptide according to claim 10.

12. The polynucleotide of claim 11, wherein the polynucleotide comprises any of SEQ ID NOS: 2 or 4-7.

13. A method of making the phospholipid bilayer or micelle according to claim 1, comprising
    a) providing a protein-polymer surfactant conjugate comprising an anchor protein conjugated to a surfactant; and
    b) contacting a phospholipid bilayer or micelle with the protein-polymer surfactant conjugate to embed the protein-polymer surfactant conjugate within the phospholipid bilayer or micelle,
    wherein the anchor protein is a cationised protein or an anionised protein and is a protein which does not comprise a —$CH_2C(O)NCH_3(CH_2)_3N(CH_3)_2H^+$ linker covalently bonded to an amino acid side chain.

14. The method of claim 13 wherein the anchor protein is a supercharged protein obtained by a method comprising expression of a recombinant DNA sequence encoding the supercharged protein.

15. The method of claim 14 wherein the recombinant DNA sequence further encodes a secondary molecule, such that the recombinant DNA sequence encodes a fusion protein comprising the supercharged protein and the secondary molecule, and wherein the secondary molecule comprises one or more of CshA, a portion of CshA comprising the fibronectin-binging portion of CshA (SEQ ID NO: 19), a functional variant having at least 90% sequence identity to SEQ ID NO: 19, OpdA (SEQ ID NO: 10 or SEQ ID NO: 39), thrombin, prothrombin, P1GF-2 (SEQ ID NO: 22), a portion of PIGF-2$_{(123-144)}$ (SEQ ID NO: 21), a functional variant of P1GF-2 having at least 90% sequence identity to SEQ ID NO: 21, a SpyCatcher polypeptide (SEQ ID NO: 23) or a SpyTag polypeptide (SEQ ID NO: 24), or comprises a functional variant of any of these having at least about 60% sequence identity to the non-variant sequence (SEQ ID NOS: 10, 19, 21-24, or 39).

16. The method of claim 13, wherein the anchor protein is an enzyme.

17. A method of labelling a cell with a protein label, comprising contacting a cell with a phospholipid bilayer produced by a method comprising:
    a) providing a protein-polymer surfactant conjugate comprising an anchor protein conjugated to the surfactant; and
    b) contacting a phospholipid bilayer with the protein-polymer surfactant conjugate to embed the protein-polymer surfactant conjugate within the phospholipid bilayer,
    wherein the anchor protein is a cationised protein or an anionised protein and is a protein which does not comprise a —$CH_2C(O)NCH_3(CH_2)_3N(CH_3)_2H^+$ linker covalently bonded to an amino acid side chain, and wherein the phospholipid bilayer forms the external membrane of the cell and the protein-polymer surfactant conjugate comprises the protein label.

18. The method of claim 17, wherein the anchor protein is an enzyme.

19. A method of promoting tissue growth and/or healing in a subject in need thereof, comprising introducing the cell of claim 5 to a site where tissue is desired to grow and/or heal in the subject, wherein the anchor protein is a protein known to promote growth and/or healing of the tissue, or wherein the protein-polymer surfactant conjugate comprises a secondary molecule which is known to promote growth and/or healing of the tissue.

20. A method of targeting a cell to a tissue in a subject in need thereof, comprising contacting a tissue with the cell of claim 5, wherein the protein-polymer surfactant conjugate comprises a protein that specifically targets the tissue.

21. A method of treating myocardial infarction, cardiomyopathy and/or myocarditis in a human or animal subject in need thereof, comprising administering the cell of claim 5 to the human or animal subject, wherein the protein-polymer surfactant conjugate comprises a protein that specifically targets cardiac tissue.

22. A method of delivering a protein to the interior of a cell, comprising contacting the cell with a phospholipid bilayer or micelle comprising at least one embedded protein-polymer surfactant conjugate comprising an anchor protein conjugated to a surfactant, wherein the anchor protein is a cationised protein or an anionised protein, wherein the at least one protein-polymer surfactant conjugate is embedded within the phospholipid bilayer or micelle, and wherein the anchor protein is a protein which does not comprise a —$CH_2C(O)NCH_3(CH_2)_3N(CH_3)_2H^+$ linker covalently bonded to an amino acid side chain, and wherein the protein-polymer surfactant conjugate comprises a molecule which promotes or inhibits the speed/rate of endocytosis.

23. The method of claim 22, wherein the anchor protein is an enzyme.

24. A method of decontaminating a sample comprising a poison, comprising contacting the sample with a phospholipid bilayer or micelle comprising at least one embedded protein-polymer surfactant conjugate comprising an anchor protein conjugated to a surfactant, wherein the anchor protein is a cationised or an anionised protein, wherein the at least one protein-polymer surfactant conjugate is embedded within the phospholipid bilayer or micelle, wherein the anchor protein is a protein which does not comprise a —$CH_2C(O)NCH_3(CH_2)_3N(CH_3)_2H^+$ linker covalently bonded to an amino acid side chain, and wherein the anchor protein is an enzyme which can neutralise the poison or is linked to a secondary molecule which can bind to or neutralise the poison.

25. The method of claim 24 wherein the sample is a surface, land, a soil sample, or a fabric, wherein the anchor protein is an enzyme which can neutralize the poison, and wherein the enzyme is OpdA or a functional variant or portion thereof capable of degrading an organophosphorus compound.

26. The method of claim 24, wherein the sample is a surface, land, a soil sample, or a fabric, wherein the anchor protein is linked to a secondary molecule which can bind to or neutralise the poison, and wherein the secondary molecule is OpdA SEQ ID NO: 39) or a functional variant or portion thereof capable of degrading an organophosphorus compound.

\* \* \* \* \*